United States Patent
Abo et al.

(10) Patent No.: US 6,815,190 B1
(45) Date of Patent: Nov. 9, 2004

(54) CUTINASE VARIANTS

(75) Inventors: Masanobu Abo, Chiba-ken (JP); Shiro Fukuyama, Chiba (JP); Allan Svendsen, Hørsholm (DK); Tomoko Matsui, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/857,068

(22) PCT Filed: Dec. 3, 1999

(86) PCT No.: PCT/DK99/00678

§ 371 (c)(1),
(2), (4) Date: May 31, 2001

(87) PCT Pub. No.: WO00/34450

PCT Pub. Date: Jun. 15, 2000

Related U.S. Application Data

(60) Provisional application No. 60/124,671, filed on Mar. 16, 1999, and provisional application No. 60/115,591, filed on Dec. 9, 1998.

(30) Foreign Application Priority Data

Apr. 12, 1998 (DK) .......................................... 1998 01604
Mar. 9, 1999 (DK) ........................................ 1999 00330

(51) Int. Cl.⁷ .......................... C12N 9/20; C12N 15/00; C12N 15/09; C12N 15/63; C12N 15/70; C12N 15/74; C12N 5/00; C12N 5/06; C12N 15/85; C12N 1/20; C12P 23/00; C12P 1/00; C12Q 1/64; C07H 21/04; C11D 3/00

(52) U.S. Cl. .................. 435/198; 435/71.1; 435/320.1; 435/252.33; 435/325; 435/41; 435/9; 435/455; 435/471; 536/23.2; 510/300

(58) Field of Search ............................... 435/198, 71.1, 435/320.1, 252.33, 325, 9, 455, 471, 41, 252.3; 536/23.2; 510/300

(56) References Cited

U.S. PATENT DOCUMENTS 5,827,719 A * 10/1998 Sandal ........................ 435/198
6,254,645 B1 * 7/2001 Kellis, Jr. ...................... 8/401

FOREIGN PATENT DOCUMENTS

WO     WO 94/14964    * 7/1994

OTHER PUBLICATIONS

Nicolas,A. and Cambillau,C. (1995) Fusarium Solani Cutinase Mutant With Thr 45 Replaced By Ala (gi|1827561|pdb|1XZG| [1827561]) and Fusarium Solani Cutinase Mutant With Thr 119 Replaced By His (gi|1827559|pdb|1XZI| [1827559]).*
Longhi,S. and Cambillau,C. (1995) Fusarium Solani Cutinase Mutant With Thr 38 Replaced By Phe gi|1827558|pdb|pdb|1XZJ|, Cutinase, R196e Mutant. (gi|1633261|pdb|1CUH| [1633261]), and Cutinase, A199c Mutant (gi|1633258|pdb|1CUU| [1633258]).*
WF Fett, HC Gerard, RA Moreau, SF Osman and LE Jones Screening of Nonfilamentous Bacteria for Production of Cutin–Degrading Enzymes Appl. Environ. Microbiol., Jul. 1992, 2123–2130, vol. 58, No. 7 (Abstract).*
Alignment of SEQ ID No.: 2 from 08/827,997 with Accession# Q99174 by BLOSUM62.*
Ausbel, FM (1995) Enzymatic manipulation of DNA and RNA In: Current Protocols in Molecular Biology Unit 3.16.*

* cited by examiner

Primary Examiner—Rebecca E. Prouty
Assistant Examiner—S Swope
(74) Attorney, Agent, or Firm—Elias Lambiris; Jason Garbell

(57) ABSTRACT

The present invention relates to cutinase variants having improved thermostability. The variants have one or more amino acid substitutions within the vicinity of the N-terminal amino acid.

27 Claims, 34 Drawing Sheets

Fig. 1

3D structure of cutinase from *Humicola insolens*

| ATOM | 1 | N | GLY | A | 3 | 24.424 | -7.935 | 18.390 | 1.00 | 46.73 |
|------|---|---|-----|---|---|--------|--------|--------|------|-------|
| ATOM | 2 | CA | GLY | A | 3 | 23.848 | -8.994 | 17.546 | 1.00 | 42.29 |
| ATOM | 3 | C | GLY | A | 3 | 24.396 | -10.112 | 16.727 | 1.00 | 37.35 |
| ATOM | 4 | O | GLY | A | 3 | 25.347 | -10.913 | 16.728 | 1.00 | 35.38 |
| ATOM | 5 | N | ALA | A | 4 | 23.664 | -10.625 | 15.797 | 1.00 | 34.53 |
| ATOM | 6 | CA | ALA | A | 4 | 23.051 | -10.874 | 14.555 | 1.00 | 30.95 |
| ATOM | 7 | C | ALA | A | 4 | 21.574 | -11.246 | 14.920 | 1.00 | 28.33 |
| ATOM | 8 | O | ALA | A | 4 | 20.677 | -10.499 | 14.446 | 1.00 | 22.94 |
| ATOM | 9 | CB | ALA | A | 4 | 23.574 | -11.780 | 13.556 | 1.00 | 26.92 |
| ATOM | 10 | N | ILE | A | 5 | 21.583 | -12.058 | 16.043 | 1.00 | 26.48 |
| ATOM | 11 | CA | ILE | A | 5 | 20.281 | -12.289 | 16.637 | 1.00 | 25.65 |
| ATOM | 12 | C | ILE | A | 5 | 20.316 | -12.151 | 18.118 | 1.00 | 22.40 |
| ATOM | 13 | O | ILE | A | 5 | 21.060 | -12.888 | 18.717 | 1.00 | 24.74 |
| ATOM | 14 | CB | ILE | A | 5 | 19.724 | -13.683 | 16.524 | 1.00 | 26.04 |
| ATOM | 15 | CG1 | ILE | A | 5 | 19.852 | -13.927 | 15.050 | 1.00 | 29.85 |
| ATOM | 16 | CG2 | ILE | A | 5 | 18.374 | -13.558 | 17.159 | 1.00 | 20.48 |
| ATOM | 17 | CD1 | ILE | A | 5 | 19.066 | -15.133 | 14.709 | 1.00 | 27.96 |
| ATOM | 18 | N | GLU | A | 6 | 19.461 | -11.377 | 18.668 | 1.00 | 20.52 |
| ATOM | 19 | CA | GLU | A | 6 | 19.207 | -11.015 | 20.040 | 1.00 | 17.94 |
| ATOM | 20 | C | GLU | A | 6 | 17.711 | -11.027 | 20.432 | 1.00 | 17.76 |
| ATOM | 21 | O | GLU | A | 6 | 16.931 | -10.165 | 19.990 | 1.00 | 17.60 |
| ATOM | 22 | CB | GLU | A | 6 | 19.809 | -9.614 | 20.199 | 1.00 | 14.22 |
| ATOM | 23 | CG | GLU | A | 6 | 21.232 | -9.374 | 20.385 | 1.00 | 16.71 |
| ATOM | 24 | CD | GLU | A | 6 | 22.148 | -10.387 | 21.030 | 1.00 | 34.47 |
| ATOM | 25 | OE1 | GLU | A | 6 | 21.634 | -11.347 | 21.693 | 1.00 | 49.57 |
| ATOM | 26 | OE2 | GLU | A | 6 | 23.410 | -10.310 | 20.975 | 1.00 | 37.43 |
| ATOM | 27 | N | ASN | A | 7 | 17.375 | -11.895 | 21.333 | 1.00 | 21.67 |
| ATOM | 28 | CA | ASN | A | 7 | 16.070 | -11.854 | 21.846 | 1.00 | 24.04 |
| ATOM | 29 | C | ASN | A | 7 | 15.927 | -11.488 | 23.238 | 1.00 | 22.08 |
| ATOM | 30 | O | ASN | A | 7 | 15.098 | -12.179 | 23.820 | 1.00 | 24.00 |
| ATOM | 31 | CB | ASN | A | 7 | 15.468 | -13.307 | 21.820 | 1.00 | 25.06 |
| ATOM | 32 | CG | ASN | A | 7 | 15.039 | -13.160 | 20.341 | 1.00 | 38.52 |
| ATOM | 33 | OD1 | ASN | A | 7 | 15.519 | -14.147 | 19.759 | 1.00 | 48.45 |
| ATOM | 34 | ND2 | ASN | A | 7 | 14.318 | -12.081 | 19.968 | 1.00 | 36.89 |
| ATOM | 35 | N | GLY | A | 8 | 16.671 | -10.813 | 23.926 | 1.00 | 23.56 |
| ATOM | 36 | CA | GLY | A | 8 | 16.654 | -10.628 | 25.363 | 1.00 | 23.69 |
| ATOM | 37 | C | GLY | A | 8 | 15.366 | -10.247 | 25.984 | 1.00 | 22.72 |
| ATOM | 38 | O | GLY | A | 8 | 14.967 | -10.939 | 26.867 | 1.00 | 32.25 |
| ATOM | 39 | N | LEU | A | 9 | 14.785 | -9.144 | 25.755 | 1.00 | 23.61 |
| ATOM | 40 | CA | LEU | A | 9 | 13.470 | -8.753 | 26.033 | 1.00 | 23.73 |
| ATOM | 41 | C | LEU | A | 9 | 12.559 | -9.961 | 25.782 | 1.00 | 25.93 |
| ATOM | 42 | O | LEU | A | 9 | 11.494 | -10.054 | 26.480 | 1.00 | 30.47 |
| ATOM | 43 | CB | LEU | A | 9 | 12.971 | -7.621 | 25.105 | 1.00 | 5.84 |
| ATOM | 44 | CG | LEU | A | 9 | 11.556 | -7.227 | 25.470 | 1.00 | 23.25 |
| ATOM | 45 | CD1 | LEU | A | 9 | 11.422 | -6.765 | 26.968 | 1.00 | 20.21 |
| ATOM | 46 | CD2 | LEU | A | 9 | 11.009 | -6.071 | 24.714 | 1.00 | 17.64 |
| ATOM | 47 | N | GLU | A | 10 | 12.775 | -10.786 | 24.773 | 1.00 | 29.56 |

| | | | | | | | | | |
|---|---|---|---|---|---|---|---|---|---|
| ATOM | 48 | CA | GLU | A | 10 | 11.635 | -11.681 | 24.484 | 1.00 33.93 |
| ATOM | 49 | C | GLU | A | 10 | 11.640 | -12.872 | 25.412 | 1.00 32.18 |
| ATOM | 50 | O | GLU | A | 10 | 10.600 | -13.159 | 25.996 | 1.00 36.67 |
| ATOM | 51 | CB | GLU | A | 10 | 11.513 | -11.996 | 23.012 | 1.00 40.97 |
| ATOM | 52 | CG | GLU | A | 10 | 10.054 | -12.303 | 22.745 | 1.00 51.96 |
| ATOM | 53 | CD | GLU | A | 10 | 9.570 | -11.711 | 21.437 | 1.00 54.08 |
| ATOM | 54 | OE1 | GLU | A | 10 | 10.488 | -11.440 | 20.635 | 1.00 48.22 |
| ATOM | 55 | OE2 | GLU | A | 10 | 8.323 | -11.643 | 21.471 | 1.00 52.39 |
| ATOM | 56 | N | SER | A | 11 | 12.822 | -13.334 | 25.688 | 1.00 29.58 |
| ATOM | 57 | CA | SER | A | 11 | 12.993 | -14.455 | 26.645 | 1.00 35.25 |
| ATOM | 58 | C | SER | A | 11 | 13.403 | -14.012 | 28.047 | 1.00 39.86 |
| ATOM | 59 | O | SER | A | 11 | 13.688 | -14.790 | 28.919 | 1.00 43.72 |
| ATOM | 60 | CB | SER | A | 11 | 14.053 | -15.364 | 25.983 | 1.00 33.73 |
| ATOM | 61 | OG | SER | A | 11 | 15.275 | -14.620 | 25.928 | 1.00 46.98 |
| ATOM | 62 | N | GLY | A | 12 | 13.467 | -12.802 | 28.456 | 1.00 41.40 |
| ATOM | 63 | CA | GLY | A | 12 | 13.841 | -12.332 | 29.752 | 1.00 45.34 |
| ATOM | 64 | C | GLY | A | 12 | 12.673 | -12.562 | 30.694 | 1.00 47.62 |
| ATOM | 65 | O | GLY | A | 12 | 11.485 | -12.335 | 30.335 | 1.00 50.76 |
| ATOM | 66 | N | SER | A | 13 | 12.969 | -12.900 | 31.936 | 1.00 48.09 |
| ATOM | 67 | CA | SER | A | 13 | 11.974 | -13.158 | 32.995 | 1.00 45.26 |
| ATOM | 68 | C | SER | A | 13 | 11.509 | -11.933 | 33.772 | 1.00 39.53 |
| ATOM | 69 | O | SER | A | 13 | 12.563 | -11.204 | 33.992 | 1.00 36.30 |
| ATOM | 70 | CB | SER | A | 13 | 12.708 | -14.006 | 34.101 | 1.00 51.20 |
| ATOM | 71 | OG | SER | A | 13 | 12.006 | -13.947 | 35.338 | 1.00 57.14 |
| ATOM | 72 | N | ALA | A | 14 | 10.256 | -11.785 | 34.214 | 1.00 35.22 |
| ATOM | 73 | CA | ALA | A | 14 | 10.068 | -10.530 | 34.964 | 1.00 34.78 |
| ATOM | 74 | C | ALA | A | 14 | 10.574 | -10.620 | 36.417 | 1.00 37.51 |
| ATOM | 75 | O | ALA | A | 14 | 10.809 | -9.584 | 37.113 | 1.00 38.41 |
| ATOM | 76 | CB | ALA | A | 14 | 8.714 | -9.915 | 34.903 | 1.00 32.71 |
| ATOM | 77 | N | ASN | A | 15 | 11.039 | -11.834 | 36.737 | 1.00 38.85 |
| ATOM | 78 | CA | ASN | A | 15 | 11.715 | -12.086 | 37.963 | 1.00 43.49 |
| ATOM | 79 | C | ASN | A | 15 | 13.073 | -11.411 | 37.953 | 1.00 46.45 |
| ATOM | 80 | O | ASN | A | 15 | 13.453 | -11.022 | 39.022 | 1.00 52.50 |
| ATOM | 81 | CB | ASN | A | 15 | 12.088 | -13.533 | 38.207 | 1.00 53.08 |
| ATOM | 82 | CG | ASN | A | 15 | 10.772 | -14.226 | 38.553 | 1.00 71.86 |
| ATOM | 83 | OD1 | ASN | A | 15 | 9.837 | -13.535 | 38.998 | 1.00 71.73 |
| ATOM | 84 | ND2 | ASN | A | 15 | 10.866 | -15.523 | 38.267 | 1.00 77.71 |
| ATOM | 85 | N | ALA | A | 16 | 13.712 | -11.305 | 36.812 | 1.00 46.73 |
| ATOM | 86 | CA | ALA | A | 16 | 14.915 | -10.470 | 36.743 | 1.00 41.22 |
| ATOM | 87 | C | ALA | A | 16 | 15.031 | -9.286 | 35.798 | 1.00 36.70 |
| ATOM | 88 | O | ALA | A | 16 | 16.027 | -9.254 | 35.075 | 1.00 37.67 |
| ATOM | 89 | CB | ALA | A | 16 | 15.903 | -11.545 | 36.301 | 1.00 41.80 |
| ATOM | 90 | N | CYS | A | 17 | 14.300 | -8.227 | 35.843 | 1.00 30.62 |
| ATOM | 91 | CA | CYS | A | 17 | 14.614 | -7.093 | 34.997 | 1.00 31.78 |
| ATOM | 92 | C | CYS | A | 17 | 16.024 | -6.579 | 35.149 | 1.00 32.94 |
| ATOM | 93 | O | CYS | A | 17 | 16.744 | -6.850 | 36.113 | 1.00 39.10 |
| ATOM | 94 | CB | CYS | A | 17 | 13.679 | -5.881 | 35.138 | 1.00 28.00 |
| ATOM | 95 | SG | CYS | A | 17 | 12.048 | -6.583 | 34.858 | 1.00 24.72 |

| | | | | | | | | | |
|---|---|---|---|---|---|---|---|---|---|
| ATOM | 96 | N | PRO | A | 18 | 16.529 | -5.910 | 34.092 | 1.00 30.49 |
| ATOM | 97 | CA | PRO | A | 18 | 17.994 | -5.626 | 33.971 | 1.00 22.04 |
| ATOM | 98 | C | PRO | A | 18 | 18.178 | -4.138 | 34.241 | 1.00 20.15 |
| ATOM | 99 | O | PRO | A | 18 | 17.085 | -3.459 | 34.370 | 1.00 17.83 |
| ATOM | 100 | CB | PRO | A | 18 | 18.353 | -6.003 | 32.559 | 1.00 19.20 |
| ATOM | 101 | CG | PRO | A | 18 | 17.044 | -6.595 | 32.101 | 1.00 20.16 |
| ATOM | 102 | CD | PRO | A | 18 | 15.903 | -5.936 | 32.792 | 1.00 24.35 |
| ATOM | 103 | N | ASP | A | 19 | 19.428 | -3.652 | 34.011 | 1.00 14.85 |
| ATOM | 104 | CA | ASP | A | 19 | 19.451 | -2.168 | 34.226 | 1.00 16.59 |
| ATOM | 105 | C | ASP | A | 19 | 18.739 | -1.367 | 33.156 | 1.00 20.42 |
| ATOM | 106 | O | ASP | A | 19 | 18.311 | -0.242 | 33.430 | 1.00 23.84 |
| ATOM | 107 | CB | ASP | A | 19 | 20.896 | -1.818 | 34.485 | 1.00 27.25 |
| ATOM | 108 | CG | ASP | A | 19 | 21.433 | -2.389 | 35.793 | 1.00 42.30 |
| ATOM | 109 | OD1 | ASP | A | 19 | 21.162 | -3.549 | 36.297 | 1.00 53.52 |
| ATOM | 110 | OD2 | ASP | A | 19 | 22.251 | -1.719 | 36.543 | 1.00 54.02 |
| ATOM | 111 | N | ALA | A | 20 | 18.646 | -1.780 | 31.895 | 1.00 20.18 |
| ATOM | 112 | CA | ALA | A | 20 | 18.066 | -1.036 | 30.809 | 1.00 17.43 |
| ATOM | 113 | C | ALA | A | 20 | 17.713 | -2.087 | 29.703 | 1.00 16.06 |
| ATOM | 114 | O | ALA | A | 20 | 18.334 | -3.172 | 29.860 | 1.00 9.45 |
| ATOM | 115 | CB | ALA | A | 20 | 18.975 | -0.048 | 30.100 | 1.00 12.07 |
| ATOM | 116 | N | ILE | A | 21 | 16.814 | -1.602 | 28.829 | 1.00 8.47 |
| ATOM | 117 | CA | ILE | A | 21 | 16.657 | -2.583 | 27.753 | 1.00 9.23 |
| ATOM | 118 | C | ILE | A | 21 | 16.952 | -1.745 | 26.486 | 1.00 14.77 |
| ATOM | 119 | O | ILE | A | 21 | 16.681 | -0.473 | 26.403 | 1.00 12.01 |
| ATOM | 120 | CB | ILE | A | 21 | 15.208 | -2.984 | 27.837 | 1.00 16.28 |
| ATOM | 121 | CG1 | ILE | A | 21 | 14.851 | -3.898 | 28.956 | 1.00 15.55 |
| ATOM | 122 | CG2 | ILE | A | 21 | 14.689 | -3.671 | 26.514 | 1.00 13.71 |
| ATOM | 123 | CD1 | ILE | A | 21 | 13.401 | -3.879 | 29.372 | 1.00 6.12 |
| ATOM | 124 | N | LEU | A | 22 | 17.432 | -2.451 | 25.391 | 1.00 12.24 |
| ATOM | 125 | CA | LEU | A | 22 | 17.665 | -1.774 | 24.087 | 1.00 11.27 |
| ATOM | 126 | C | LEU | A | 22 | 16.849 | -2.517 | 23.038 | 1.00 14.60 |
| ATOM | 127 | O | LEU | A | 22 | 16.908 | -3.781 | 22.850 | 1.00 9.78 |
| ATOM | 128 | CB | LEU | A | 22 | 19.087 | -1.865 | 23.693 | 1.00 10.96 |
| ATOM | 129 | CG | LEU | A | 22 | 19.493 | -1.543 | 22.257 | 1.00 10.32 |
| ATOM | 130 | CD1 | LEU | A | 22 | 19.311 | -0.081 | 21.900 | 1.00 4.72 |
| ATOM | 131 | CD2 | LEU | A | 22 | 20.990 | -1.842 | 22.156 | 1.00 7.42 |
| ATOM | 132 | N | ILE | A | 23 | 16.038 | -1.815 | 22.242 | 1.00 15.13 |
| ATOM | 133 | CA | ILE | A | 23 | 15.298 | -2.459 | 21.115 | 1.00 18.06 |
| ATOM | 134 | C | ILE | A | 23 | 15.916 | -1.771 | 19.901 | 1.00 17.42 |
| ATOM | 135 | O | ILE | A | 23 | 16.117 | -0.519 | 19.795 | 1.00 19.31 |
| ATOM | 136 | CB | ILE | A | 23 | 13.820 | -2.194 | 21.392 | 1.00 18.16 |
| ATOM | 137 | CG1 | ILE | A | 23 | 13.208 | -3.076 | 22.447 | 1.00 14.23 |
| ATOM | 138 | CG2 | ILE | A | 23 | 12.787 | -2.167 | 20.247 | 1.00 13.19 |
| ATOM | 139 | CD1 | ILE | A | 23 | 12.142 | -2.065 | 22.976 | 1.00 20.41 |
| ATOM | 140 | N | PHE | A | 24 | 16.218 | -2.548 | 18.940 | 1.00 14.59 |
| ATOM | 141 | CA | PHE | A | 24 | 16.859 | -2.159 | 17.671 | 1.00 11.72 |
| ATOM | 142 | C | PHE | A | 24 | 16.347 | -2.719 | 16.353 | 1.00 7.25 |
| ATOM | 143 | O | PHE | A | 24 | 16.095 | -3.998 | 16.161 | 1.00 3.47 |

| ATOM | 144 | CB  | PHE | A | 24 | 18.195 | -2.855 | 17.658 | 1.00 | 12.61 |
| ATOM | 145 | CG  | PHE | A | 24 | 19.015 | -2.150 | 16.716 | 1.00 | 10.72 |
| ATOM | 146 | CD1 | PHE | A | 24 | 19.457 | -0.844 | 16.913 | 1.00 | 13.08 |
| ATOM | 147 | CD2 | PHE | A | 24 | 19.325 | -2.852 | 15.558 | 1.00 | 6.61 |
| ATOM | 148 | CE1 | PHE | A | 24 | 20.232 | -0.187 | 15.983 | 1.00 | 4.86 |
| ATOM | 149 | CE2 | PHE | A | 24 | 20.061 | -2.218 | 14.545 | 1.00 | 7.61 |
| ATOM | 150 | CZ  | PHE | A | 24 | 20.550 | -0.823 | 14.804 | 1.00 | 8.78 |
| ATOM | 151 | N   | ALA | A | 25 | 16.037 | -1.700 | 15.449 | 1.00 | 6.32 |
| ATOM | 152 | CA  | ALA | A | 25 | 15.662 | -2.158 | 14.068 | 1.00 | 7.18 |
| ATOM | 153 | C   | ALA | A | 25 | 16.851 | -1.976 | 13.055 | 1.00 | 8.59 |
| ATOM | 154 | O   | ALA | A | 25 | 17.518 | -1.000 | 13.133 | 1.00 | 5.95 |
| ATOM | 155 | CB  | ALA | A | 25 | 14.488 | -1.402 | 13.562 | 1.00 | 8.27 |
| ATOM | 156 | N   | ARG | A | 26 | 17.174 | -3.032 | 12.325 | 1.00 | 8.84 |
| ATOM | 157 | CA  | ARG | A | 26 | 18.134 | -3.278 | 11.277 | 1.00 | 4.04 |
| ATOM | 158 | C   | ARG | A | 26 | 17.691 | -2.694 | 9.894  | 1.00 | 7.67 |
| ATOM | 159 | O   | ARG | A | 26 | 16.527 | -2.361 | 9.525  | 1.00 | 9.36 |
| ATOM | 160 | CB  | ARG | A | 26 | 18.581 | -4.659 | 10.756 | 1.00 | 6.06 |
| ATOM | 161 | CG  | ARG | A | 26 | 17.705 | -5.741 | 10.439 | 1.00 | 5.08 |
| ATOM | 162 | CD  | ARG | A | 26 | 18.069 | -7.224 | 10.382 | 1.00 | 6.73 |
| ATOM | 163 | NE  | ARG | A | 26 | 17.000 | -8.053 | 9.708  | 1.00 | 9.04 |
| ATOM | 164 | CZ  | ARG | A | 26 | 15.724 | -8.206 | 9.912  | 1.00 | 7.06 |
| ATOM | 165 | NH1 | ARG | A | 26 | 15.085 | -7.535 | 10.895 | 1.00 | 22.93 |
| ATOM | 166 | NH2 | ARG | A | 26 | 14.809 | -8.825 | 9.346  | 1.00 | 7.89 |
| ATOM | 167 | N   | GLY | A | 27 | 18.761 | -2.539 | 9.092  | 1.00 | 7.71 |
| ATOM | 168 | CA  | GLY | A | 27 | 18.537 | -1.888 | 7.782  | 1.00 | 5.34 |
| ATOM | 169 | C   | GLY | A | 27 | 18.063 | -2.896 | 6.862  | 1.00 | 4.70 |
| ATOM | 170 | O   | GLY | A | 27 | 18.155 | -4.139 | 7.075  | 1.00 | 13.14 |
| ATOM | 171 | N   | SER | A | 28 | 17.562 | -2.612 | 5.765  | 1.00 | 11.82 |
| ATOM | 172 | CA  | SER | A | 28 | 17.108 | -3.325 | 4.615  | 1.00 | 14.72 |
| ATOM | 173 | C   | SER | A | 28 | 18.214 | -4.327 | 4.142  | 1.00 | 7.74 |
| ATOM | 174 | O   | SER | A | 28 | 19.286 | -3.973 | 4.083  | 1.00 | 6.71 |
| ATOM | 175 | CB  | SER | A | 28 | 16.460 | -2.352 | 3.538  | 1.00 | 6.38 |
| ATOM | 176 | OG  | SER | A | 28 | 16.819 | -0.978 | 3.833  | 1.00 | 28.10 |
| ATOM | 177 | N   | THR | A | 29 | 17.942 | -5.634 | 4.241  | 1.00 | 4.79 |
| ATOM | 178 | CA  | THR | A | 29 | 18.562 | -6.763 | 3.914  | 1.00 | 8.71 |
| ATOM | 179 | C   | THR | A | 29 | 19.500 | -7.271 | 4.985  | 1.00 | 14.00 |
| ATOM | 180 | O   | THR | A | 29 | 20.162 | -8.326 | 4.713  | 1.00 | 17.68 |
| ATOM | 181 | CB  | THR | A | 29 | 19.454 | -6.680 | 2.617  | 1.00 | 14.90 |
| ATOM | 182 | OG1 | THR | A | 29 | 20.736 | -6.066 | 2.595  | 1.00 | 14.00 |
| ATOM | 183 | CG2 | THR | A | 29 | 18.785 | -5.888 | 1.561  | 1.00 | 15.59 |
| ATOM | 184 | N   | GLU | A | 30 | 19.740 | -6.599 | 6.105  | 1.00 | 14.52 |
| ATOM | 185 | CA  | GLU | A | 30 | 20.677 | -7.266 | 7.056  | 1.00 | 14.10 |
| ATOM | 186 | C   | GLU | A | 30 | 20.092 | -8.513 | 7.647  | 1.00 | 13.07 |
| ATOM | 187 | O   | GLU | A | 30 | 18.916 | -8.726 | 7.705  | 1.00 | 19.98 |
| ATOM | 188 | CB  | GLU | A | 30 | 21.228 | -6.371 | 8.072  | 1.00 | 15.45 |
| ATOM | 189 | CG  | GLU | A | 30 | 21.166 | -4.945 | 7.709  | 1.00 | 8.37 |
| ATOM | 190 | CD  | GLU | A | 30 | 22.073 | -4.143 | 8.637  | 1.00 | 23.08 |
| ATOM | 191 | OE1 | GLU | A | 30 | 21.395 | -3.328 | 9.284  | 1.00 | 19.26 |

| | | | | | | | | | | |
|---|---|---|---|---|---|---|---|---|---|---|
| ATOM | 192 | OE2 | GLU | A | 30 | 23.317 | -4.327 | 8.712 | 1.00 | 19.71 |
| ATOM | 193 | N | PRO | A | 31 | 20.875 | -9.479 | 7.918 | 1.00 | 13.09 |
| ATOM | 194 | CA | PRO | A | 31 | 20.477 | -10.818 | 8.402 | 1.00 | 14.56 |
| ATOM | 195 | C | PRO | A | 31 | 20.167 | -10.698 | 9.895 | 1.00 | 18.27 |
| ATOM | 196 | O | PRO | A | 31 | 20.148 | -9.636 | 10.392 | 1.00 | 20.45 |
| ATOM | 197 | CB | PRO | A | 31 | 21.690 | -11.692 | 8.215 | 1.00 | 10.95 |
| ATOM | 198 | CG | PRO | A | 31 | 22.790 | -10.664 | 8.455 | 1.00 | 11.24 |
| ATOM | 199 | CD | PRO | A | 31 | 22.350 | -9.316 | 7.864 | 1.00 | 13.71 |
| ATOM | 200 | N | GLY | A | 32 | 19.612 | -11.689 | 10.472 | 1.00 | 18.99 |
| ATOM | 201 | CA | GLY | A | 32 | 19.205 | -11.774 | 11.816 | 1.00 | 13.53 |
| ATOM | 202 | C | GLY | A | 32 | 18.133 | -10.808 | 12.188 | 1.00 | 16.62 |
| ATOM | 203 | O | GLY | A | 32 | 17.345 | -10.294 | 11.411 | 1.00 | 17.01 |
| ATOM | 204 | N | ASN | A | 33 | 18.055 | -10.528 | 13.468 | 1.00 | 16.15 |
| ATOM | 205 | CA | ASN | A | 33 | 17.290 | -9.346 | 13.823 | 1.00 | 14.74 |
| ATOM | 206 | C | ASN | A | 33 | 18.294 | -8.273 | 14.230 | 1.00 | 15.46 |
| ATOM | 207 | O | ASN | A | 33 | 17.774 | -7.184 | 14.575 | 1.00 | 15.90 |
| ATOM | 208 | CB | ASN | A | 33 | 16.241 | -9.663 | 14.867 | 1.00 | 17.42 |
| ATOM | 209 | CG | ASN | A | 33 | 16.827 | -10.201 | 16.127 | 1.00 | 17.97 |
| ATOM | 210 | OD1 | ASN | A | 33 | 16.112 | -10.395 | 17.089 | 1.00 | 19.05 |
| ATOM | 211 | ND2 | ASN | A | 33 | 18.074 | -10.460 | 16.112 | 1.00 | 13.29 |
| ATOM | 212 | N | MET | A | 34 | 19.633 | -8.378 | 14.282 | 1.00 | 14.22 |
| ATOM | 213 | CA | MET | A | 34 | 20.282 | -7.171 | 14.751 | 1.00 | 12.97 |
| ATOM | 214 | C | MET | A | 34 | 21.142 | -6.663 | 13.611 | 1.00 | 19.02 |
| ATOM | 215 | O | MET | A | 34 | 21.654 | -5.512 | 13.713 | 1.00 | 26.04 |
| ATOM | 216 | CB | MET | A | 34 | 21.202 | -7.329 | 15.859 | 1.00 | 13.39 |
| ATOM | 217 | CG | MET | A | 34 | 20.579 | -7.713 | 17.163 | 1.00 | 9.02 |
| ATOM | 218 | SD | MET | A | 34 | 20.175 | -6.316 | 18.069 | 1.00 | 9.13 |
| ATOM | 219 | CE | MET | A | 34 | 21.481 | -5.121 | 18.095 | 1.00 | 4.11 |
| ATOM | 220 | N | GLY | A | 35 | 21.259 | -7.446 | 12.550 | 1.00 | 19.99 |
| ATOM | 221 | CA | GLY | A | 35 | 22.071 | -7.135 | 11.418 | 1.00 | 14.30 |
| ATOM | 222 | C | GLY | A | 35 | 23.511 | -7.340 | 11.764 | 1.00 | 17.58 |
| ATOM | 223 | O | GLY | A | 35 | 23.965 | -7.724 | 12.842 | 1.00 | 12.78 |
| ATOM | 224 | N | ILE | A | 36 | 24.450 | -6.839 | 10.950 | 1.00 | 20.63 |
| ATOM | 225 | CA | ILE | A | 36 | 25.833 | -7.029 | 11.277 | 1.00 | 17.71 |
| ATOM | 226 | C | ILE | A | 36 | 26.609 | -5.714 | 11.280 | 1.00 | 16.15 |
| ATOM | 227 | O | ILE | A | 36 | 27.865 | -5.618 | 11.662 | 1.00 | 20.30 |
| ATOM | 228 | CB | ILE | A | 36 | 26.412 | -8.070 | 10.327 | 1.00 | 30.19 |
| ATOM | 229 | CG1 | ILE | A | 36 | 26.088 | -7.448 | 8.959 | 1.00 | 31.16 |
| ATOM | 230 | CG2 | ILE | A | 36 | 25.944 | -9.490 | 10.543 | 1.00 | 15.68 |
| ATOM | 231 | CD1 | ILE | A | 36 | 26.922 | -8.149 | 7.958 | 1.00 | 34.10 |
| ATOM | 232 | N | THR | A | 37 | 25.905 | -4.589 | 11.040 | 1.00 | 13.00 |
| ATOM | 233 | CA | THR | A | 37 | 26.825 | -3.396 | 11.141 | 1.00 | 9.67 |
| ATOM | 234 | C | THR | A | 37 | 26.587 | -2.513 | 12.350 | 1.00 | 15.44 |
| ATOM | 235 | O | THR | A | 37 | 27.040 | -3.055 | 13.410 | 1.00 | 20.20 |
| ATOM | 236 | CB | THR | A | 37 | 26.592 | -2.679 | 9.818 | 1.00 | 14.13 |
| ATOM | 237 | OG1 | THR | A | 37 | 25.241 | -2.212 | 9.503 | 1.00 | 22.62 |
| ATOM | 238 | CG2 | THR | A | 37 | 26.949 | -3.739 | 8.800 | 1.00 | 2.29 |
| ATOM | 239 | N | VAL | A | 38 | 25.733 | -1.493 | 12.249 | 1.00 | 11.92 |

| | | | | | | | | | |
|---|---|---|---|---|---|---|---|---|---|
| ATOM | 240 | CA | VAL | A | 38 | 25.237 | -0.800 | 13.411 | 1.00 15.22 |
| ATOM | 241 | C | VAL | A | 38 | 24.588 | -1.455 | 14.612 | 1.00 14.68 |
| ATOM | 242 | O | VAL | A | 38 | 24.906 | -1.185 | 15.733 | 1.00 15.89 |
| ATOM | 243 | CB | VAL | A | 38 | 24.124 | 0.180 | 12.855 | 1.00 14.13 |
| ATOM | 244 | CG1 | VAL | A | 38 | 23.663 | 0.897 | 14.167 | 1.00 13.55 |
| ATOM | 245 | CG2 | VAL | A | 38 | 24.570 | 1.025 | 11.670 | 1.00 6.75 |
| ATOM | 246 | N | GLY | A | 39 | 23.745 | -2.410 | 14.677 | 1.00 14.24 |
| ATOM | 247 | CA | GLY | A | 39 | 23.135 | -3.151 | 15.746 | 1.00 11.03 |
| ATOM | 248 | C | GLY | A | 39 | 24.096 | -3.586 | 16.791 | 1.00 13.34 |
| ATOM | 249 | O | GLY | A | 39 | 24.131 | -3.181 | 17.934 | 1.00 15.13 |
| ATOM | 250 | N | PRO | A | 40 | 25.067 | -4.340 | 16.352 | 1.00 14.70 |
| ATOM | 251 | CA | PRO | A | 40 | 26.094 | -5.025 | 17.171 | 1.00 13.44 |
| ATOM | 252 | C | PRO | A | 40 | 27.010 | -3.909 | 17.589 | 1.00 11.81 |
| ATOM | 253 | O | PRO | A | 40 | 27.346 | -3.871 | 18.764 | 1.00 12.79 |
| ATOM | 254 | CB | PRO | A | 40 | 26.723 | -6.111 | 16.279 | 1.00 8.43 |
| ATOM | 255 | CG | PRO | A | 40 | 25.873 | -6.243 | 14.950 | 1.00 4.84 |
| ATOM | 256 | CD | PRO | A | 40 | 25.198 | -4.902 | 14.995 | 1.00 12.36 |
| ATOM | 257 | N | ALA | A | 41 | 27.226 | -2.979 | 16.695 | 1.00 7.41 |
| ATOM | 258 | CA | ALA | A | 41 | 28.066 | -1.962 | 17.278 | 1.00 11.03 |
| ATOM | 259 | C | ALA | A | 41 | 27.378 | -1.206 | 18.439 | 1.00 14.87 |
| ATOM | 260 | O | ALA | A | 41 | 28.028 | -0.503 | 19.274 | 1.00 14.26 |
| ATOM | 261 | CB | ALA | A | 41 | 28.579 | -0.905 | 16.313 | 1.00 7.17 |
| ATOM | 262 | N | LEU | A | 42 | 26.135 | -0.811 | 18.237 | 1.00 11.87 |
| ATOM | 263 | CA | LEU | A | 42 | 25.487 | -0.048 | 19.300 | 1.00 12.36 |
| ATOM | 264 | C | LEU | A | 42 | 25.337 | -0.856 | 20.624 | 1.00 11.94 |
| ATOM | 265 | O | LEU | A | 42 | 25.423 | -0.397 | 21.730 | 1.00 8.33 |
| ATOM | 266 | CB | LEU | A | 42 | 24.036 | 0.168 | 18.811 | 1.00 13.24 |
| ATOM | 267 | CG | LEU | A | 42 | 23.272 | 1.160 | 19.676 | 1.00 6.90 |
| ATOM | 268 | CD1 | LEU | A | 42 | 24.108 | 2.419 | 19.962 | 1.00 6.62 |
| ATOM | 269 | CD2 | LEU | A | 42 | 21.991 | 1.580 | 18.943 | 1.00 7.11 |
| ATOM | 270 | N | ALA | A | 43 | 24.905 | -2.095 | 20.482 | 1.00 10.88 |
| ATOM | 271 | CA | ALA | A | 43 | 24.761 | -3.027 | 21.553 | 1.00 12.37 |
| ATOM | 272 | C | ALA | A | 43 | 26.106 | -3.136 | 22.252 | 1.00 15.45 |
| ATOM | 273 | O | ALA | A | 43 | 25.958 | -2.743 | 23.433 | 1.00 20.80 |
| ATOM | 274 | CB | ALA | A | 43 | 24.148 | -4.324 | 21.002 | 1.00 9.60 |
| ATOM | 275 | N | ASN | A | 44 | 27.263 | -3.440 | 21.636 | 1.00 16.91 |
| ATOM | 276 | CA | ASN | A | 44 | 28.454 | -3.434 | 22.439 | 1.00 20.33 |
| ATOM | 277 | C | ASN | A | 44 | 28.717 | -2.044 | 23.113 | 1.00 17.66 |
| ATOM | 278 | O | ASN | A | 44 | 29.019 | -1.991 | 24.301 | 1.00 17.06 |
| ATOM | 279 | CB | ASN | A | 44 | 29.756 | -3.695 | 21.625 | 1.00 35.48 |
| ATOM | 280 | CG | ASN | A | 44 | 29.564 | -5.115 | 21.138 | 1.00 58.23 |
| ATOM | 281 | OD1 | ASN | A | 44 | 30.013 | -5.403 | 20.034 | 1.00 79.77 |
| ATOM | 282 | ND2 | ASN | A | 44 | 28.908 | -5.945 | 21.921 | 1.00 70.10 |
| ATOM | 283 | N | GLY | A | 45 | 28.682 | -0.988 | 22.297 | 1.00 14.39 |
| ATOM | 284 | CA | GLY | A | 45 | 29.015 | 0.221 | 22.976 | 1.00 11.65 |
| ATOM | 285 | C | GLY | A | 45 | 28.175 | 0.255 | 24.234 | 1.00 14.30 |
| ATOM | 286 | O | GLY | A | 45 | 28.529 | 0.582 | 25.385 | 1.00 10.77 |
| ATOM | 287 | N | LEU | A | 46 | 26.861 | 0.099 | 24.065 | 1.00 16.88 |

| | | | | | | | | | |
|---|---|---|---|---|---|---|---|---|---|
| ATOM | 288 | CA | LEU | A | 46 | 25.968 | 0.248 | 25.207 | 1.00 16.29 |
| ATOM | 289 | C | LEU | A | 46 | 26.395 | -0.651 | 26.346 | 1.00 13.48 |
| ATOM | 290 | O | LEU | A | 46 | 26.579 | -0.325 | 27.462 | 1.00 7.75 |
| ATOM | 291 | CB | LEU | A | 46 | 24.608 | -0.243 | 24.847 | 1.00 19.46 |
| ATOM | 292 | CG | LEU | A | 46 | 23.642 | 0.551 | 25.664 | 1.00 13.97 |
| ATOM | 293 | CD1 | LEU | A | 46 | 24.089 | 1.994 | 25.563 | 1.00 13.99 |
| ATOM | 294 | CD2 | LEU | A | 46 | 22.275 | 0.465 | 25.038 | 1.00 32.18 |
| ATOM | 295 | N | GLU | A | 47 | 26.523 | -1.890 | 25.882 | 1.00 15.90 |
| ATOM | 296 | CA | GLU | A | 47 | 26.910 | -2.886 | 26.909 | 1.00 24.03 |
| ATOM | 297 | C | GLU | A | 47 | 28.140 | -2.500 | 27.702 | 1.00 24.14 |
| ATOM | 298 | O | GLU | A | 47 | 28.722 | -3.203 | 28.500 | 1.00 27.24 |
| ATOM | 299 | CB | GLU | A | 47 | 27.147 | -4.206 | 26.204 | 1.00 33.33 |
| ATOM | 300 | CG | GLU | A | 47 | 27.386 | -5.254 | 27.245 | 1.00 51.29 |
| ATOM | 301 | CD | GLU | A | 47 | 27.661 | -6.560 | 26.524 | 1.00 68.40 |
| ATOM | 302 | OE1 | GLU | A | 47 | 26.741 | -7.007 | 25.777 | 1.00 66.37 |
| ATOM | 303 | OE2 | GLU | A | 47 | 28.856 | -6.921 | 26.830 | 1.00 78.70 |
| ATOM | 304 | N | SER | A | 48 | 28.992 | -1.626 | 27.215 | 1.00 27.50 |
| ATOM | 305 | CA | SER | A | 48 | 30.331 | -1.518 | 27.789 | 1.00 25.23 |
| ATOM | 306 | C | SER | A | 48 | 30.108 | -0.555 | 28.926 | 1.00 26.91 |
| ATOM | 307 | O | SER | A | 48 | 31.124 | -0.058 | 29.462 | 1.00 33.39 |
| ATOM | 308 | CB | SER | A | 48 | 31.116 | -0.990 | 26.621 | 1.00 21.90 |
| ATOM | 309 | OG | SER | A | 48 | 31.294 | 0.422 | 26.483 | 1.00 27.87 |
| ATOM | 310 | N | HIS | A | 49 | 28.826 | -0.101 | 28.995 | 1.00 25.04 |
| ATOM | 311 | CA | HIS | A | 49 | 28.542 | 0.955 | 29.956 | 1.00 19.72 |
| ATOM | 312 | C | HIS | A | 49 | 27.480 | 0.461 | 30.950 | 1.00 22.55 |
| ATOM | 313 | O | HIS | A | 49 | 27.186 | 1.089 | 31.898 | 1.00 27.93 |
| ATOM | 314 | CB | HIS | A | 49 | 28.094 | 2.197 | 29.463 | 1.00 16.13 |
| ATOM | 315 | CG | HIS | A | 49 | 28.806 | 3.036 | 28.520 | 1.00 39.79 |
| ATOM | 316 | ND1 | HIS | A | 49 | 29.564 | 4.058 | 28.953 | 1.00 45.66 |
| ATOM | 317 | CD2 | HIS | A | 49 | 28.776 | 3.070 | 27.197 | 1.00 46.91 |
| ATOM | 318 | CE1 | HIS | A | 49 | 30.028 | 4.750 | 27.979 | 1.00 45.87 |
| ATOM | 319 | NE2 | HIS | A | 49 | 29.544 | 4.139 | 26.934 | 1.00 50.84 |
| ATOM | 320 | N | ILE | A | 50 | 27.009 | -0.703 | 30.715 | 1.00 18.34 |
| ATOM | 321 | CA | ILE | A | 50 | 25.874 | -1.129 | 31.415 | 1.00 19.89 |
| ATOM | 322 | C | ILE | A | 50 | 25.917 | -2.629 | 31.146 | 1.00 26.29 |
| ATOM | 323 | O | ILE | A | 50 | 25.322 | -3.023 | 30.168 | 1.00 25.33 |
| ATOM | 324 | CB | ILE | A | 50 | 24.527 | -0.535 | 31.008 | 1.00 10.50 |
| ATOM | 325 | CG1 | ILE | A | 50 | 24.340 | 0.906 | 31.292 | 1.00 4.97 |
| ATOM | 326 | CG2 | ILE | A | 50 | 23.466 | -1.298 | 31.697 | 1.00 12.96 |
| ATOM | 327 | CD1 | ILE | A | 50 | 23.413 | 1.845 | 30.602 | 1.00 16.65 |
| ATOM | 328 | N | ARG | A | 51 | 26.707 | -3.256 | 32.066 | 1.00 31.77 |
| ATOM | 329 | CA | ARG | A | 51 | 26.887 | -4.714 | 32.107 | 1.00 29.06 |
| ATOM | 330 | C | ARG | A | 51 | 25.457 | -5.331 | 32.170 | 1.00 32.68 |
| ATOM | 331 | O | ARG | A | 51 | 25.396 | -6.363 | 31.512 | 1.00 37.16 |
| ATOM | 332 | N | ASN | A | 52 | 24.380 | -4.817 | 32.788 | 1.00 28.48 |
| ATOM | 333 | CA | ASN | A | 52 | 23.284 | -5.767 | 32.832 | 1.00 26.39 |
| ATOM | 334 | C | ASN | A | 52 | 22.176 | -5.178 | 31.993 | 1.00 27.75 |
| ATOM | 335 | O | ASN | A | 52 | 21.333 | -4.488 | 32.636 | 1.00 26.68 |

| | | | | | | | | | |
|---|---|---|---|---|---|---|---|---|---|
| ATOM | 336 | CB | ASN | A | 52 | 22.750 | -5.884 | 34.232 | 1.00 34.86 |
| ATOM | 337 | CG | ASN | A | 52 | 21.637 | -6.879 | 34.271 | 1.00 39.54 |
| ATOM | 338 | OD1 | ASN | A | 52 | 20.781 | -6.541 | 35.095 | 1.00 54.31 |
| ATOM | 339 | ND2 | ASN | A | 52 | 21.611 | -7.954 | 33.503 | 1.00 48.82 |
| ATOM | 340 | N | ILE | A | 53 | 22.127 | -5.699 | 30.800 | 1.00 24.42 |
| ATOM | 341 | CA | ILE | A | 53 | 21.261 | -5.092 | 29.772 | 1.00 20.15 |
| ATOM | 342 | C | ILE | A | 53 | 20.585 | -6.151 | 28.912 | 1.00 17.63 |
| ATOM | 343 | O | ILE | A | 53 | 21.020 | -7.349 | 28.917 | 1.00 18.01 |
| ATOM | 344 | CB | ILE | A | 53 | 22.245 | -4.297 | 28.880 | 1.00 14.09 |
| ATOM | 345 | CG1 | ILE | A | 53 | 21.682 | -3.257 | 27.936 | 1.00 22.91 |
| ATOM | 346 | CG2 | ILE | A | 53 | 22.907 | -5.321 | 27.946 | 1.00 16.37 |
| ATOM | 347 | CD1 | ILE | A | 53 | 22.877 | -2.315 | 27.622 | 1.00 38.17 |
| ATOM | 348 | N | TRP | A | 54 | 19.447 | -5.880 | 28.383 | 1.00 15.19 |
| ATOM | 349 | CA | TRP | A | 54 | 18.804 | -6.889 | 27.567 | 1.00 17.96 |
| ATOM | 350 | C | TRP | A | 54 | 18.803 | -6.230 | 26.151 | 1.00 19.82 |
| ATOM | 351 | O | TRP | A | 54 | 18.340 | -5.059 | 25.985 | 1.00 18.37 |
| ATOM | 352 | CB | TRP | A | 54 | 17.364 | -7.046 | 27.998 | 1.00 23.18 |
| ATOM | 353 | CG | TRP | A | 54 | 16.949 | -7.932 | 29.100 | 1.00 24.57 |
| ATOM | 354 | CD1 | TRP | A | 54 | 17.757 | -8.727 | 29.895 | 1.00 24.46 |
| ATOM | 355 | CD2 | TRP | A | 54 | 15.595 | -8.164 | 29.603 | 1.00 30.21 |
| ATOM | 356 | NE1 | TRP | A | 54 | 17.004 | -9.372 | 30.858 | 1.00 25.87 |
| ATOM | 357 | CE2 | TRP | A | 54 | 15.692 | -9.039 | 30.700 | 1.00 24.92 |
| ATOM | 358 | CE3 | TRP | A | 54 | 14.358 | -7.633 | 29.243 | 1.00 36.26 |
| ATOM | 359 | CZ2 | TRP | A | 54 | 14.611 | -9.442 | 31.432 | 1.00 19.75 |
| ATOM | 360 | CZ3 | TRP | A | 54 | 13.316 | -8.042 | 30.009 | 1.00 32.94 |
| ATOM | 361 | CH2 | TRP | A | 54 | 13.451 | -8.916 | 31.068 | 1.00 23.02 |
| ATOM | 362 | N | ILE | A | 55 | 19.063 | -7.152 | 25.204 | 1.00 15.21 |
| ATOM | 363 | CA | ILE | A | 55 | 19.178 | -6.655 | 23.838 | 1.00 12.41 |
| ATOM | 364 | C | ILE | A | 55 | 18.091 | -7.215 | 22.962 | 1.00 11.40 |
| ATOM | 365 | O | ILE | A | 55 | 17.955 | -8.378 | 22.680 | 1.00 7.34 |
| ATOM | 366 | CB | ILE | A | 55 | 20.546 | -6.962 | 23.201 | 1.00 16.44 |
| ATOM | 367 | CG1 | ILE | A | 55 | 21.939 | -6.409 | 23.702 | 1.00 8.75 |
| ATOM | 368 | CG2 | ILE | A | 55 | 20.384 | -6.460 | 21.750 | 1.00 21.77 |
| ATOM | 369 | CD1 | ILE | A | 55 | 21.767 | -5.582 | 24.863 | 1.00 16.23 |
| ATOM | 370 | N | GLN | A | 56 | 17.226 | -6.412 | 22.390 | 1.00 9.67 |
| ATOM | 371 | CA | GLN | A | 56 | 16.161 | -7.016 | 21.619 | 1.00 10.90 |
| ATOM | 372 | C | GLN | A | 56 | 16.432 | -6.621 | 20.143 | 1.00 13.08 |
| ATOM | 373 | O | GLN | A | 56 | 16.402 | -5.393 | 19.953 | 1.00 10.32 |
| ATOM | 374 | CB | GLN | A | 56 | 14.786 | -6.542 | 22.014 | 1.00 11.49 |
| ATOM | 375 | CG | GLN | A | 56 | 13.653 | -7.256 | 21.316 | 1.00 23.47 |
| ATOM | 376 | CD | GLN | A | 56 | 13.789 | -8.741 | 21.351 | 1.00 24.88 |
| ATOM | 377 | OE1 | GLN | A | 56 | 13.610 | -9.379 | 20.324 | 1.00 9.56 |
| ATOM | 378 | NE2 | GLN | A | 56 | 14.119 | -9.221 | 22.544 | 1.00 17.94 |
| ATOM | 379 | N | GLY | A | 57 | 16.288 | -7.645 | 19.216 | 1.00 6.84 |
| ATOM | 380 | CA | GLY | A | 57 | 16.174 | -7.019 | 17.841 | 1.00 16.15 |
| ATOM | 381 | C | GLY | A | 57 | 14.740 | -7.085 | 17.267 | 1.00 13.72 |
| ATOM | 382 | O | GLY | A | 57 | 14.124 | -8.016 | 17.752 | 1.00 12.70 |
| ATOM | 383 | N | VAL | A | 58 | 14.068 | -6.264 | 16.525 | 1.00 12.73 |

```
ATOM    384  CA   VAL A  58      12.739  -6.308  16.070  1.00 11.16
ATOM    385  C    VAL A  58      12.715  -7.246  14.893  1.00 14.85
ATOM    386  O    VAL A  58      13.234  -6.891  13.849  1.00 18.64
ATOM    387  CB   VAL A  58      12.262  -4.984  15.352  1.00  6.54
ATOM    388  CG1  VAL A  58      10.894  -4.974  14.731  1.00  5.89
ATOM    389  CG2  VAL A  58      12.650  -3.840  16.331  1.00  5.86
ATOM    390  N    GLY A  59      12.209  -8.465  15.008  1.00 21.96
ATOM    391  CA   GLY A  59      12.120  -9.385  13.874  1.00 17.81
ATOM    392  C    GLY A  59      10.645  -9.561  13.550  1.00 23.35
ATOM    393  O    GLY A  59       9.919  -8.579  13.249  1.00 27.99
ATOM    394  N    GLY A  60      10.166 -10.805  13.623  1.00 18.75
ATOM    395  CA   GLY A  60       8.841 -11.142  13.285  1.00 11.46
ATOM    396  C    GLY A  60       8.550 -10.833  11.851  1.00 14.56
ATOM    397  O    GLY A  60       9.160 -11.439  11.003  1.00 16.32
ATOM    398  N    PRO A  61       7.505 -10.103  11.612  1.00 12.10
ATOM    399  CA   PRO A  61       7.123  -9.774  10.250  1.00 14.70
ATOM    400  C    PRO A  61       8.230  -8.941   9.570  1.00 22.17
ATOM    401  O    PRO A  61       8.143  -8.758   8.344  1.00 25.74
ATOM    402  CB   PRO A  61       5.911  -8.860  10.332  1.00 14.30
ATOM    403  CG   PRO A  61       5.880  -8.514  11.784  1.00 13.62
ATOM    404  CD   PRO A  61       6.723  -9.417  12.576  1.00 12.29
ATOM    405  N    TYR A  62       9.162  -8.257  10.292  1.00 21.56
ATOM    406  CA   TYR A  62       9.973  -7.242   9.674  1.00 17.07
ATOM    407  C    TYR A  62      11.133  -7.907   9.047  1.00 18.73
ATOM    408  O    TYR A  62      12.132  -8.213   9.691  1.00 22.39
ATOM    409  CB   TYR A  62      10.504  -6.401  10.803  1.00 17.51
ATOM    410  CG   TYR A  62      11.461  -5.421  10.236  1.00 15.23
ATOM    411  CD1  TYR A  62      11.343  -4.920   9.032  1.00 17.79
ATOM    412  CD2  TYR A  62      12.465  -4.971  10.969  1.00 19.09
ATOM    413  CE1  TYR A  62      12.206  -3.997   8.506  1.00 19.28
ATOM    414  CE2  TYR A  62      13.438  -4.101  10.490  1.00 25.40
ATOM    415  CZ   TYR A  62      13.327  -3.571   9.186  1.00 20.95
ATOM    416  OH   TYR A  62      14.320  -2.649   8.791  1.00 14.70
ATOM    417  N    ASP A  63      10.998  -8.419   7.816  1.00 19.47
ATOM    418  CA   ASP A  63      12.137  -9.011   7.081  1.00 17.52
ATOM    419  C    ASP A  63      13.027  -7.973   6.453  1.00 17.97
ATOM    420  O    ASP A  63      13.628  -8.442   5.512  1.00 14.94
ATOM    421  CB   ASP A  63      11.474  -9.873   6.015  1.00 17.16
ATOM    422  CG   ASP A  63      10.563  -9.136   5.096  1.00 27.75
ATOM    423  OD1  ASP A  63      10.049  -8.030   5.281  1.00 34.11
ATOM    424  OD2  ASP A  63      10.300  -9.635   4.002  1.00 44.13
ATOM    425  N    ALA A  64      13.089  -6.685   6.584  1.00 15.36
ATOM    426  CA   ALA A  64      14.054  -5.725   6.098  1.00 17.14
ATOM    427  C    ALA A  64      14.118  -5.780   4.589  1.00 21.10
ATOM    428  O    ALA A  64      15.193  -5.861   3.968  1.00 23.12
ATOM    429  CB   ALA A  64      15.458  -5.861   6.646  1.00 20.45
ATOM    430  N    ALA A  65      12.946  -6.009   4.006  1.00 22.21
ATOM    431  CA   ALA A  65      12.817  -6.072   2.565  1.00 21.81
```

| | | | | | | | | |
|---|---|---|---|---|---|---|---|---|
| ATOM | 432 | C | ALA | A | 65 | 13.143 | -4.857 | 1.745 | 1.00 | 21.76 |
| ATOM | 433 | O | ALA | A | 65 | 12.855 | -3.801 | 2.229 | 1.00 | 23.60 |
| ATOM | 434 | CB | ALA | A | 65 | 11.384 | -6.390 | 2.364 | 1.00 | 17.31 |
| ATOM | 435 | N | LEU | A | 66 | 13.401 | -4.866 | 0.402 | 1.00 | 21.48 |
| ATOM | 436 | CA | LEU | A | 66 | 13.763 | -3.581 | -0.216 | 1.00 | 13.20 |
| ATOM | 437 | C | LEU | A | 66 | 12.469 | -2.913 | -0.452 | 1.00 | 13.90 |
| ATOM | 438 | O | LEU | A | 66 | 12.548 | -1.767 | -0.197 | 1.00 | 11.85 |
| ATOM | 439 | CB | LEU | A | 66 | 14.593 | -3.602 | -1.470 | 1.00 | 3.92 |
| ATOM | 440 | CG | LEU | A | 66 | 15.891 | -4.308 | -1.191 | 1.00 | 9.05 |
| ATOM | 441 | CD1 | LEU | A | 66 | 16.509 | -4.725 | -2.438 | 1.00 | 12.78 |
| ATOM | 442 | CD2 | LEU | A | 66 | 16.569 | -3.119 | -0.580 | 1.00 | 13.44 |
| ATOM | 443 | N | ALA | A | 67 | 11.413 | -3.625 | -0.801 | 1.00 | 14.94 |
| ATOM | 444 | CA | ALA | A | 67 | 10.253 | -2.759 | -1.277 | 1.00 | 12.42 |
| ATOM | 445 | C | ALA | A | 67 | 9.626 | -1.879 | -0.224 | 1.00 | 14.21 |
| ATOM | 446 | O | ALA | A | 67 | 9.218 | -0.818 | -0.643 | 1.00 | 14.29 |
| ATOM | 447 | CB | ALA | A | 67 | 9.089 | -3.588 | -1.781 | 1.00 | 3.90 |
| ATOM | 448 | N | THR | A | 68 | 9.494 | -2.409 | 1.006 | 1.00 | 12.11 |
| ATOM | 449 | CA | THR | A | 68 | 8.780 | -1.647 | 1.997 | 1.00 | 11.77 |
| ATOM | 450 | C | THR | A | 68 | 9.242 | -0.214 | 2.219 | 1.00 | 13.05 |
| ATOM | 451 | O | THR | A | 68 | 8.597 | 0.683 | 2.766 | 1.00 | 11.13 |
| ATOM | 452 | CB | THR | A | 68 | 8.892 | -2.488 | 3.241 | 1.00 | 13.93 |
| ATOM | 453 | OG1 | THR | A | 68 | 10.145 | -3.150 | 3.224 | 1.00 | 27.44 |
| ATOM | 454 | CG2 | THR | A | 68 | 7.783 | -3.459 | 3.087 | 1.00 | 13.39 |
| ATOM | 455 | N | ASN | A | 69 | 10.450 | -0.057 | 1.808 | 1.00 | 7.59 |
| ATOM | 456 | CA | ASN | A | 69 | 11.020 | 1.236 | 1.791 | 1.00 | 8.76 |
| ATOM | 457 | C | ASN | A | 69 | 10.095 | 2.165 | 1.047 | 1.00 | 10.28 |
| ATOM | 458 | O | ASN | A | 69 | 9.950 | 3.345 | 1.305 | 1.00 | 5.30 |
| ATOM | 459 | CB | ASN | A | 69 | 12.461 | 1.251 | 1.231 | 1.00 | 5.54 |
| ATOM | 460 | CG | ASN | A | 69 | 13.374 | 1.207 | 2.398 | 1.00 | 15.08 |
| ATOM | 461 | OD1 | ASN | A | 69 | 13.307 | 2.124 | 3.275 | 1.00 | 31.90 |
| ATOM | 462 | ND2 | ASN | A | 69 | 14.048 | 0.099 | 2.360 | 1.00 | 4.51 |
| ATOM | 463 | N | PHE | A | 70 | 9.390 | 1.656 | 0.079 | 1.00 | 19.09 |
| ATOM | 464 | CA | PHE | A | 70 | 8.552 | 2.619 | -0.631 | 1.00 | 21.80 |
| ATOM | 465 | C | PHE | A | 70 | 7.157 | 2.836 | -0.123 | 1.00 | 23.36 |
| ATOM | 466 | O | PHE | A | 70 | 6.509 | 3.717 | -0.724 | 1.00 | 25.74 |
| ATOM | 467 | CB | PHE | A | 70 | 8.547 | 2.386 | -2.082 | 1.00 | 17.38 |
| ATOM | 468 | CG | PHE | A | 70 | 9.870 | 2.360 | -2.770 | 1.00 | 15.72 |
| ATOM | 469 | CD1 | PHE | A | 70 | 10.080 | 3.430 | -3.576 | 1.00 | 5.15 |
| ATOM | 470 | CD2 | PHE | A | 70 | 10.702 | 1.245 | -2.497 | 1.00 | 7.61 |
| ATOM | 471 | CE1 | PHE | A | 70 | 11.268 | 3.330 | -4.191 | 1.00 | 16.05 |
| ATOM | 472 | CE2 | PHE | A | 70 | 11.913 | 1.267 | -3.168 | 1.00 | 22.23 |
| ATOM | 473 | CZ | PHE | A | 70 | 12.199 | 2.314 | -4.016 | 1.00 | 9.57 |
| ATOM | 474 | N | LEU | A | 71 | 6.765 | 2.246 | 1.034 | 1.00 | 25.53 |
| ATOM | 475 | CA | LEU | A | 71 | 5.506 | 2.725 | 1.599 | 1.00 | 24.24 |
| ATOM | 476 | C | LEU | A | 71 | 5.649 | 4.037 | 2.343 | 1.00 | 27.91 |
| ATOM | 477 | O | LEU | A | 71 | 6.694 | 4.521 | 2.750 | 1.00 | 28.86 |
| ATOM | 478 | CB | LEU | A | 71 | 5.150 | 1.635 | 2.535 | 1.00 | 19.99 |
| ATOM | 479 | CG | LEU | A | 71 | 5.003 | 0.342 | 1.873 | 1.00 | 16.09 |

```
ATOM    480  CD1 LEU A  71       4.879  -0.764   2.885  1.00  18.12
ATOM    481  CD2 LEU A  71       3.786   0.546   1.000  1.00  18.24
ATOM    482  N   PRO A  72       4.535   4.663   2.529  1.00  33.01
ATOM    483  CA  PRO A  72       4.389   5.888   3.311  1.00  34.96
ATOM    484  C   PRO A  72       4.865   5.590   4.778  1.00  32.90
ATOM    485  O   PRO A  72       4.619   4.512   5.331  1.00  28.55
ATOM    486  CB  PRO A  72       2.983   6.453   3.095  1.00  32.98
ATOM    487  CG  PRO A  72       2.224   5.189   2.827  1.00  30.36
ATOM    488  CD  PRO A  72       3.188   4.093   2.380  1.00  33.56
ATOM    489  N   ARG A  73       5.601   6.610   5.221  1.00  27.54
ATOM    490  CA  ARG A  73       6.325   6.547   6.408  1.00  25.42
ATOM    491  C   ARG A  73       7.613   5.755   6.321  1.00  21.78
ATOM    492  O   ARG A  73       8.360   5.950   7.304  1.00  29.61
ATOM    493  CB  ARG A  73       5.469   5.978   7.549  1.00  24.29
ATOM    494  CG  ARG A  73       4.575   6.998   8.155  1.00  23.47
ATOM    495  CD  ARG A  73       3.818   6.793   9.360  1.00  29.73
ATOM    496  NE  ARG A  73       3.222   5.460   9.392  1.00  36.30
ATOM    497  CZ  ARG A  73       2.891   5.312  10.713  1.00  42.26
ATOM    498  NH1 ARG A  73       3.145   6.288  11.555  1.00  26.57
ATOM    499  NH2 ARG A  73       2.320   4.144  10.883  1.00  39.03
ATOM    500  N   GLY A  74       7.868   4.909   5.326  1.00   8.42
ATOM    501  CA  GLY A  74       9.120   4.291   5.332  1.00   5.06
ATOM    502  C   GLY A  74       9.243   2.858   5.508  1.00  12.74
ATOM    503  O   GLY A  74      10.256   2.286   5.317  1.00  16.46
ATOM    504  N   THR A  75       8.145   2.321   5.906  1.00  12.82
ATOM    505  CA  THR A  75       8.036   0.869   6.008  1.00  11.14
ATOM    506  C   THR A  75       6.625   0.428   6.134  1.00  10.64
ATOM    507  O   THR A  75       5.757   1.231   5.949  1.00   9.36
ATOM    508  CB  THR A  75       8.843   0.398   7.219  1.00   6.97
ATOM    509  OG1 THR A  75       8.938  -0.950   7.125  1.00   5.64
ATOM    510  CG2 THR A  75       8.108   0.865   8.603  1.00   6.30
ATOM    511  N   SER A  76       6.409  -0.858   6.259  1.00  10.07
ATOM    512  CA  SER A  76       5.061  -1.384   6.354  1.00  13.33
ATOM    513  C   SER A  76       4.405  -1.163   7.747  1.00  21.87
ATOM    514  O   SER A  76       5.228  -1.102   8.679  1.00  24.22
ATOM    515  CB  SER A  76       5.030  -2.832   6.083  1.00   4.81
ATOM    516  OG  SER A  76       5.327  -3.664   7.107  1.00  16.98
ATOM    517  N   GLN A  77       3.082  -1.100   7.911  1.00  24.90
ATOM    518  CA  GLN A  77       2.454  -1.020   9.166  1.00  23.85
ATOM    519  C   GLN A  77       2.643  -2.236  10.015  1.00  19.58
ATOM    520  O   GLN A  77       2.908  -2.140  11.203  1.00  15.15
ATOM    521  CB  GLN A  77       0.983  -0.703   9.217  1.00  32.64
ATOM    522  CG  GLN A  77       0.567  -0.580  10.642  1.00  49.56
ATOM    523  CD  GLN A  77       0.689   0.785  11.194  1.00  65.91
ATOM    524  OE1 GLN A  77       0.956   0.869  12.356  1.00  66.06
ATOM    525  NE2 GLN A  77       0.481   1.750  10.350  1.00  68.91
ATOM    526  N   ALA A  78       2.754  -3.376   9.402  1.00  15.90
ATOM    527  CA  ALA A  78       3.071  -4.577  10.073  1.00  19.47
```

```
ATOM   528  C   ALA A  78       4.381  -4.332  10.819  1.00 24.48
ATOM   529  O   ALA A  78       4.389  -4.729  11.983  1.00 26.91
ATOM   530  CB  ALA A  78       3.390  -5.808   9.336  1.00 17.23
ATOM   531  N   ASN A  79       5.350  -3.863  10.093  1.00 21.58
ATOM   532  CA  ASN A  79       6.602  -3.576  10.774  1.00 20.62
ATOM   533  C   ASN A  79       6.480  -2.673  11.969  1.00 20.93
ATOM   534  O   ASN A  79       6.975  -2.944  13.053  1.00 15.52
ATOM   535  CB  ASN A  79       7.474  -3.069   9.670  1.00 24.79
ATOM   536  CG  ASN A  79       7.933  -4.238   8.824  1.00 28.76
ATOM   537  OD1 ASN A  79       7.867  -5.439   9.091  1.00 25.30
ATOM   538  ND2 ASN A  79       8.488  -3.891   7.660  1.00 24.90
ATOM   539  N   ILE A  80       5.731  -1.611  11.936  1.00 15.93
ATOM   540  CA  ILE A  80       5.586  -0.574  12.924  1.00 17.00
ATOM   541  C   ILE A  80       4.925  -1.187  14.118  1.00 20.63
ATOM   542  O   ILE A  80       5.234  -0.939  15.264  1.00 18.79
ATOM   543  CB  ILE A  80       4.756   0.629  12.436  1.00 11.98
ATOM   544  CG1 ILE A  80       5.627   1.124  11.297  1.00  9.50
ATOM   545  CG2 ILE A  80       4.379   1.728  13.354  1.00 16.27
ATOM   546  CD1 ILE A  80       5.007   2.071  10.424  1.00  8.15
ATOM   547  N   ASP A  81       4.017  -2.019  13.708  1.00 19.21
ATOM   548  CA  ASP A  81       3.304  -2.778  14.728  1.00 15.15
ATOM   549  C   ASP A  81       4.147  -3.711  15.510  1.00 15.77
ATOM   550  O   ASP A  81       4.084  -3.697  16.695  1.00 15.82
ATOM   551  CB  ASP A  81       2.291  -3.438  13.868  1.00 26.36
ATOM   552  CG  ASP A  81       1.065  -2.530  13.790  1.00 23.71
ATOM   553  OD1 ASP A  81       1.105  -1.355  14.226  1.00 14.33
ATOM   554  OD2 ASP A  81       0.061  -3.125  13.222  1.00 33.05
ATOM   555  N   GLU A  82       5.148  -4.447  15.096  1.00 16.07
ATOM   556  CA  GLU A  82       5.984  -5.318  15.882  1.00 14.77
ATOM   557  C   GLU A  82       6.839  -4.355  16.667  1.00 19.33
ATOM   558  O   GLU A  82       7.315  -4.708  17.752  1.00 23.58
ATOM   559  CB  GLU A  82       6.998  -6.031  15.064  1.00 13.20
ATOM   560  CG  GLU A  82       7.792  -7.239  15.476  1.00 23.09
ATOM   561  CD  GLU A  82       6.767  -8.114  16.185  1.00 29.68
ATOM   562  OE1 GLU A  82       5.666  -7.670  16.403  1.00 26.63
ATOM   563  OE2 GLU A  82       7.273  -9.181  16.411  1.00 33.08
ATOM   564  N   GLY A  83       7.228  -3.227  16.199  1.00 16.79
ATOM   565  CA  GLY A  83       8.033  -2.428  17.140  1.00 17.32
ATOM   566  C   GLY A  83       7.238  -2.018  18.366  1.00 17.54
ATOM   567  O   GLY A  83       7.561  -2.103  19.528  1.00 15.06
ATOM   568  N   LYS A  84       6.093  -1.408  18.114  1.00 18.72
ATOM   569  CA  LYS A  84       5.050  -1.146  19.096  1.00 16.90
ATOM   570  C   LYS A  84       4.893  -2.337  20.057  1.00 17.74
ATOM   571  O   LYS A  84       4.962  -2.265  21.295  1.00 14.31
ATOM   572  CB  LYS A  84       3.799  -0.872  18.307  1.00 14.62
ATOM   573  CG  LYS A  84       3.535   0.565  18.291  1.00 19.30
ATOM   574  CD  LYS A  84       2.787   1.013  17.044  1.00 34.24
ATOM   575  CE  LYS A  84       1.568   1.902  17.337  1.00 37.70
```

| | | | | | | | | | |
|---|---|---|---|---|---|---|---|---|---|
| ATOM | 576 | NZ | LYS | A | 84 | 0.346 | 1.226 | 16.827 | 1.00 48.42 |
| ATOM | 577 | N | ARG | A | 85 | 4.617 | -3.506 | 19.519 | 1.00 18.50 |
| ATOM | 578 | CA | ARG | A | 85 | 4.583 | -4.705 | 20.280 | 1.00 19.04 |
| ATOM | 579 | C | ARG | A | 85 | 5.677 | -4.733 | 21.308 | 1.00 19.63 |
| ATOM | 580 | O | ARG | A | 85 | 5.442 | -5.192 | 22.383 | 1.00 19.24 |
| ATOM | 581 | CB | ARG | A | 85 | 4.740 | -5.979 | 19.464 | 1.00 14.74 |
| ATOM | 582 | CG | ARG | A | 85 | 3.843 | -7.094 | 19.887 | 1.00 8.85 |
| ATOM | 583 | CD | ARG | A | 85 | 4.146 | -8.554 | 19.705 | 1.00 7.20 |
| ATOM | 584 | NE | ARG | A | 85 | 5.483 | -8.898 | 19.194 | 1.00 20.30 |
| ATOM | 585 | CZ | ARG | A | 85 | 6.170 | -9.705 | 19.899 | 1.00 18.19 |
| ATOM | 586 | NH1 | ARG | A | 85 | 5.627 | -10.161 | 21.040 | 1.00 34.03 |
| ATOM | 587 | NH2 | ARG | A | 85 | 7.345 | -9.979 | 19.555 | 1.00 15.36 |
| ATOM | 588 | N | LEU | A | 86 | 6.901 | -4.586 | 20.956 | 1.00 22.21 |
| ATOM | 589 | CA | LEU | A | 86 | 8.006 | -4.792 | 21.873 | 1.00 20.94 |
| ATOM | 590 | C | LEU | A | 86 | 8.044 | -3.637 | 22.803 | 1.00 20.73 |
| ATOM | 591 | O | LEU | A | 86 | 8.155 | -3.970 | 23.925 | 1.00 22.18 |
| ATOM | 592 | CB | LEU | A | 86 | 9.333 | -4.932 | 21.168 | 1.00 6.67 |
| ATOM | 593 | CG | LEU | A | 86 | 9.358 | -6.241 | 20.282 | 1.00 11.45 |
| ATOM | 594 | CD1 | LEU | A | 86 | 10.546 | -6.054 | 19.287 | 1.00 18.60 |
| ATOM | 595 | CD2 | LEU | A | 86 | 9.362 | -7.516 | 21.020 | 1.00 5.17 |
| ATOM | 596 | N | PHE | A | 87 | 7.700 | -2.446 | 22.529 | 1.00 16.79 |
| ATOM | 597 | CA | PHE | A | 87 | 7.850 | -1.416 | 23.492 | 1.00 18.21 |
| ATOM | 598 | C | PHE | A | 87 | 6.939 | -1.805 | 24.618 | 1.00 26.51 |
| ATOM | 599 | O | PHE | A | 87 | 7.082 | -1.565 | 25.839 | 1.00 30.36 |
| ATOM | 600 | CB | PHE | A | 87 | 7.498 | -0.118 | 22.846 | 1.00 15.81 |
| ATOM | 601 | CG | PHE | A | 87 | 8.661 | 0.503 | 22.128 | 1.00 22.72 |
| ATOM | 602 | CD1 | PHE | A | 87 | 9.625 | 1.163 | 22.795 | 1.00 25.90 |
| ATOM | 603 | CD2 | PHE | A | 87 | 8.800 | 0.446 | 20.774 | 1.00 24.19 |
| ATOM | 604 | CE1 | PHE | A | 87 | 10.699 | 1.781 | 22.220 | 1.00 26.46 |
| ATOM | 605 | CE2 | PHE | A | 87 | 9.871 | 0.991 | 20.153 | 1.00 29.24 |
| ATOM | 606 | CZ | PHE | A | 87 | 10.827 | 1.669 | 20.849 | 1.00 20.81 |
| ATOM | 607 | N | ALA | A | 88 | 5.862 | -2.422 | 24.266 | 1.00 29.15 |
| ATOM | 608 | CA | ALA | A | 88 | 4.772 | -2.699 | 25.195 | 1.00 22.92 |
| ATOM | 609 | C | ALA | A | 88 | 5.186 | -3.837 | 26.068 | 1.00 22.03 |
| ATOM | 610 | O | ALA | A | 88 | 4.974 | -3.879 | 27.284 | 1.00 27.02 |
| ATOM | 611 | CB | ALA | A | 88 | 3.551 | -2.803 | 24.299 | 1.00 22.13 |
| ATOM | 612 | N | LEU | A | 89 | 5.649 | -4.897 | 25.531 | 1.00 19.16 |
| ATOM | 613 | CA | LEU | A | 89 | 6.188 | -6.032 | 26.208 | 1.00 19.29 |
| ATOM | 614 | C | LEU | A | 89 | 7.250 | -5.507 | 27.133 | 1.00 22.06 |
| ATOM | 615 | O | LEU | A | 89 | 7.449 | -6.050 | 28.177 | 1.00 20.49 |
| ATOM | 616 | CB | LEU | A | 89 | 7.021 | -6.863 | 25.221 | 1.00 18.41 |
| ATOM | 617 | CG | LEU | A | 89 | 7.477 | -8.167 | 25.834 | 1.00 20.45 |
| ATOM | 618 | CD1 | LEU | A | 89 | 6.326 | -8.707 | 26.627 | 1.00 17.22 |
| ATOM | 619 | CD2 | LEU | A | 89 | 8.060 | -9.057 | 24.769 | 1.00 18.83 |
| ATOM | 620 | N | ALA | A | 90 | 8.124 | -4.644 | 26.722 | 1.00 22.80 |
| ATOM | 621 | CA | ALA | A | 90 | 9.027 | -4.137 | 27.701 | 1.00 24.14 |
| ATOM | 622 | C | ALA | A | 90 | 8.237 | -3.488 | 28.849 | 1.00 23.63 |
| ATOM | 623 | O | ALA | A | 90 | 8.414 | -3.835 | 30.071 | 1.00 22.73 |

| | | | | | | | | | |
|---|---|---|---|---|---|---|---|---|---|
| ATOM | 624 | CB | ALA | A | 90 | 10.080 | -3.253 | 27.139 | 1.00 7.74 |
| ATOM | 625 | N | ASN | A | 91 | 7.457 | -2.445 | 28.732 | 1.00 25.45 |
| ATOM | 626 | CA | ASN | A | 91 | 6.665 | -1.979 | 29.870 | 1.00 27.25 |
| ATOM | 627 | C | ASN | A | 91 | 5.847 | -2.996 | 30.656 | 1.00 30.97 |
| ATOM | 628 | O | ASN | A | 91 | 5.346 | -2.884 | 31.768 | 1.00 27.64 |
| ATOM | 629 | CB | ASN | A | 91 | 5.560 | -1.206 | 29.125 | 1.00 29.14 |
| ATOM | 630 | CG | ASN | A | 91 | 4.946 | -0.345 | 30.216 | 1.00 31.73 |
| ATOM | 631 | OD1 | ASN | A | 91 | 3.845 | -0.692 | 30.645 | 1.00 46.76 |
| ATOM | 632 | ND2 | ASN | A | 91 | 5.641 | 0.629 | 30.643 | 1.00 29.03 |
| ATOM | 633 | N | GLN | A | 92 | 5.369 | -4.008 | 29.969 | 1.00 35.37 |
| ATOM | 634 | CA | GLN | A | 92 | 4.702 | -5.141 | 30.591 | 1.00 35.55 |
| ATOM | 635 | C | GLN | A | 92 | 5.619 | -6.072 | 31.352 | 1.00 34.28 |
| ATOM | 636 | O | GLN | A | 92 | 5.227 | -6.519 | 32.440 | 1.00 39.47 |
| ATOM | 637 | CB | GLN | A | 92 | 3.866 | -5.903 | 29.573 | 1.00 54.94 |
| ATOM | 638 | CG | GLN | A | 92 | 2.689 | -6.698 | 30.142 | 1.00 78.63 |
| ATOM | 639 | CD | GLN | A | 92 | 2.806 | -8.167 | 29.805 | 1.00 93.87 |
| ATOM | 640 | OE1 | GLN | A | 92 | 3.597 | -8.840 | 30.475 | 1.00 96.99 |
| ATOM | 641 | NE2 | GLN | A | 92 | 2.083 | -8.696 | 28.824 | 1.00 97.81 |
| ATOM | 642 | N | LYS | A | 93 | 6.859 | -6.403 | 31.050 | 1.00 31.97 |
| ATOM | 643 | CA | LYS | A | 93 | 7.675 | -7.204 | 31.972 | 1.00 25.22 |
| ATOM | 644 | C | LYS | A | 93 | 8.381 | -6.298 | 33.015 | 1.00 24.68 |
| ATOM | 645 | O | LYS | A | 93 | 8.716 | -6.793 | 34.075 | 1.00 32.13 |
| ATOM | 646 | CB | LYS | A | 93 | 8.673 | -7.980 | 31.148 | 1.00 10.86 |
| ATOM | 647 | CG | LYS | A | 93 | 8.225 | -8.963 | 30.159 | 1.00 24.26 |
| ATOM | 648 | CD | LYS | A | 93 | 9.362 | -9.966 | 29.986 | 1.00 21.96 |
| ATOM | 649 | CE | LYS | A | 93 | 9.093 | -10.718 | 28.658 | 1.00 23.78 |
| ATOM | 650 | NZ | LYS | A | 93 | 10.084 | -11.805 | 28.300 | 1.00 25.87 |
| ATOM | 651 | N | CYS | A | 94 | 8.752 | -5.096 | 32.774 | 1.00 16.62 |
| ATOM | 652 | CA | CYS | A | 94 | 9.752 | -4.412 | 33.480 | 1.00 18.95 |
| ATOM | 653 | C | CYS | A | 94 | 9.512 | -2.936 | 33.537 | 1.00 24.83 |
| ATOM | 654 | O | CYS | A | 94 | 10.184 | -2.017 | 33.150 | 1.00 26.80 |
| ATOM | 655 | CB | CYS | A | 94 | 11.147 | -4.691 | 32.911 | 1.00 3.14 |
| ATOM | 656 | SG | CYS | A | 94 | 11.618 | -6.437 | 32.882 | 1.00 25.28 |
| ATOM | 657 | N | PRO | A | 95 | 8.403 | -2.561 | 34.086 | 1.00 26.08 |
| ATOM | 658 | CA | PRO | A | 95 | 7.891 | -1.202 | 33.878 | 1.00 26.11 |
| ATOM | 659 | C | PRO | A | 95 | 8.960 | -0.259 | 34.299 | 1.00 27.32 |
| ATOM | 660 | O | PRO | A | 95 | 8.776 | 0.966 | 34.108 | 1.00 29.08 |
| ATOM | 661 | CB | PRO | A | 95 | 6.609 | -1.090 | 34.747 | 1.00 20.75 |
| ATOM | 662 | CG | PRO | A | 95 | 6.587 | -2.421 | 35.322 | 1.00 19.04 |
| ATOM | 663 | CD | PRO | A | 95 | 7.363 | -3.461 | 34.509 | 1.00 22.55 |
| ATOM | 664 | N | ASN | A | 96 | 9.836 | -0.776 | 35.193 | 1.00 31.44 |
| ATOM | 665 | CA | ASN | A | 96 | 10.559 | 0.274 | 35.966 | 1.00 35.38 |
| ATOM | 666 | C | ASN | A | 96 | 11.891 | 0.476 | 35.353 | 1.00 33.83 |
| ATOM | 667 | O | ASN | A | 96 | 12.599 | 1.359 | 35.684 | 1.00 33.31 |
| ATOM | 668 | CB | ASN | A | 96 | 10.558 | -0.099 | 37.429 | 1.00 53.70 |
| ATOM | 669 | CG | ASN | A | 96 | 9.238 | 0.342 | 38.026 | 1.00 61.69 |
| ATOM | 670 | OD1 | ASN | A | 96 | 8.758 | 1.432 | 37.706 | 1.00 64.33 |
| ATOM | 671 | ND2 | ASN | A | 96 | 8.676 | -0.526 | 38.861 | 1.00 67.25 |

| ATOM | 672 | N   | THR | A | 97  | 12.287 | -0.409 | 34.507 | 1.00 | 30.32 |
| ---- | --- | --- | --- | - | --- | ------ | ------ | ------ | ---- | ----- |
| ATOM | 673 | CA  | THR | A | 97  | 13.519 | -0.367 | 33.794 | 1.00 | 22.83 |
| ATOM | 674 | C   | THR | A | 97  | 13.404 | 0.493  | 32.534 | 1.00 | 22.44 |
| ATOM | 675 | O   | THR | A | 97  | 12.446 | 0.779  | 31.816 | 1.00 | 21.14 |
| ATOM | 676 | CB  | THR | A | 97  | 13.835 | -1.851 | 33.705 | 1.00 | 25.87 |
| ATOM | 677 | OG1 | THR | A | 97  | 14.602 | -1.915 | 32.528 | 1.00 | 38.91 |
| ATOM | 678 | CG2 | THR | A | 97  | 12.769 | -2.901 | 33.621 | 1.00 | 24.22 |
| ATOM | 679 | N   | PRO | A | 98  | 14.393 | 1.415  | 32.408 | 1.00 | 20.59 |
| ATOM | 680 | CA  | PRO | A | 98  | 14.513 | 2.292  | 31.254 | 1.00 | 18.15 |
| ATOM | 681 | C   | PRO | A | 98  | 14.882 | 1.494  | 29.978 | 1.00 | 16.07 |
| ATOM | 682 | O   | PRO | A | 98  | 15.622 | 0.462  | 29.934 | 1.00 | 17.19 |
| ATOM | 683 | CB  | PRO | A | 98  | 15.563 | 3.339  | 31.676 | 1.00 | 14.55 |
| ATOM | 684 | CG  | PRO | A | 98  | 16.270 | 2.646  | 32.699 | 1.00 | 12.29 |
| ATOM | 685 | CD  | PRO | A | 98  | 15.735 | 1.331  | 33.046 | 1.00 | 12.02 |
| ATOM | 686 | N   | VAL | A | 99  | 14.322 | 2.107  | 28.940 | 1.00 | 13.81 |
| ATOM | 687 | CA  | VAL | A | 99  | 14.225 | 1.544  | 27.632 | 1.00 | 14.02 |
| ATOM | 688 | C   | VAL | A | 99  | 14.956 | 2.407  | 26.663 | 1.00 | 10.66 |
| ATOM | 689 | O   | VAL | A | 99  | 14.716 | 3.679  | 26.712 | 1.00 | 6.90  |
| ATOM | 690 | CB  | VAL | A | 99  | 12.673 | 1.343  | 27.335 | 1.00 | 2.87  |
| ATOM | 691 | CG1 | VAL | A | 99  | 12.666 | 1.272  | 25.872 | 1.00 | 17.40 |
| ATOM | 692 | CG2 | VAL | A | 99  | 12.442 | -0.111 | 27.744 | 1.00 | 5.75  |
| ATOM | 693 | N   | VAL | A | 100 | 15.885 | 1.776  | 25.861 | 1.00 | 6.45  |
| ATOM | 694 | CA  | VAL | A | 100 | 16.525 | 2.755  | 24.900 | 1.00 | 9.61  |
| ATOM | 695 | C   | VAL | A | 100 | 16.389 | 2.159  | 23.561 | 1.00 | 10.79 |
| ATOM | 696 | O   | VAL | A | 100 | 16.256 | 0.973  | 23.477 | 1.00 | 9.11  |
| ATOM | 697 | CB  | VAL | A | 100 | 17.877 | 3.260  | 25.197 | 1.00 | 8.05  |
| ATOM | 698 | CG1 | VAL | A | 100 | 17.824 | 4.252  | 26.336 | 1.00 | 6.05  |
| ATOM | 699 | CG2 | VAL | A | 100 | 18.853 | 2.053  | 25.591 | 1.00 | 6.68  |
| ATOM | 700 | N   | ALA | A | 101 | 16.277 | 2.928  | 22.511 | 1.00 | 13.14 |
| ATOM | 701 | CA  | ALA | A | 101 | 16.127 | 2.266  | 21.183 | 1.00 | 15.67 |
| ATOM | 702 | C   | ALA | A | 101 | 17.065 | 2.747  | 20.053 | 1.00 | 12.08 |
| ATOM | 703 | O   | ALA | A | 101 | 17.261 | 4.042  | 19.907 | 1.00 | 11.16 |
| ATOM | 704 | CB  | ALA | A | 101 | 14.685 | 2.609  | 20.812 | 1.00 | 6.57  |
| ATOM | 705 | N   | GLY | A | 102 | 17.218 | 1.787  | 19.099 | 1.00 | 7.53  |
| ATOM | 706 | CA  | GLY | A | 102 | 17.949 | 2.415  | 17.939 | 1.00 | 7.10  |
| ATOM | 707 | C   | GLY | A | 102 | 17.477 | 1.803  | 16.744 | 1.00 | 7.27  |
| ATOM | 708 | O   | GLY | A | 102 | 17.102 | 0.621  | 16.878 | 1.00 | 10.83 |
| ATOM | 709 | N   | GLY | A | 103 | 17.706 | 2.407  | 15.648 | 1.00 | 7.80  |
| ATOM | 710 | CA  | GLY | A | 103 | 17.446 | 1.745  | 14.356 | 1.00 | 5.33  |
| ATOM | 711 | C   | GLY | A | 103 | 18.303 | 2.211  | 13.180 | 1.00 | 7.56  |
| ATOM | 712 | O   | GLY | A | 103 | 18.785 | 3.340  | 13.227 | 1.00 | 6.88  |
| ATOM | 713 | N   | TYR | A | 104 | 18.490 | 1.387  | 12.139 | 1.00 | 7.09  |
| ATOM | 714 | CA  | TYR | A | 104 | 19.392 | 1.682  | 11.069 | 1.00 | 5.99  |
| ATOM | 715 | C   | TYR | A | 104 | 18.705 | 1.614  | 9.705  | 1.00 | 9.47  |
| ATOM | 716 | O   | TYR | A | 104 | 18.115 | 0.638  | 9.441  | 1.00 | 6.46  |
| ATOM | 717 | CB  | TYR | A | 104 | 20.592 | 0.797  | 11.079 | 1.00 | 5.40  |
| ATOM | 718 | CG  | TYR | A | 104 | 21.436 | 1.078  | 9.876  | 1.00 | 8.05  |
| ATOM | 719 | CD1 | TYR | A | 104 | 21.708 | 2.302  | 9.352  | 1.00 | 5.91  |

| | | | | | | | | | |
|---|---|---|---|---|---|---|---|---|---|
| ATOM | 720 | CD2 | TYR | A | 104 | 21.961 | -0.044 | 9.172 | 1.00 6.85 |
| ATOM | 721 | CE1 | TYR | A | 104 | 22.447 | 2.513 | 8.186 | 1.00 5.61 |
| ATOM | 722 | CE2 | TYR | A | 104 | 22.751 | 0.052 | 8.072 | 1.00 7.49 |
| ATOM | 723 | CZ | TYR | A | 104 | 22.972 | 1.377 | 7.608 | 1.00 11.08 |
| ATOM | 724 | OH | TYR | A | 104 | 23.795 | 1.509 | 6.479 | 1.00 14.32 |
| ATOM | 725 | N | SER | A | 105 | 18.939 | 2.975 | 8.852 | 1.00 18.39 |
| ATOM | 726 | CA | SER | A | 105 | 18.190 | 2.854 | 7.601 | 1.00 9.66 |
| ATOM | 727 | C | SER | A | 105 | 16.763 | 2.370 | 7.722 | 1.00 6.10 |
| ATOM | 728 | O | SER | A | 105 | 16.090 | 3.304 | 8.077 | 1.00 5.63 |
| ATOM | 729 | CB | SER | A | 105 | 19.124 | 2.159 | 6.607 | 1.00 8.55 |
| ATOM | 730 | OG | SER | A | 105 | 18.553 | 1.685 | 5.463 | 1.00 24.30 |
| ATOM | 731 | N | GLN | A | 106 | 16.241 | 1.405 | 7.079 | 1.00 9.93 |
| ATOM | 732 | CA | GLN | A | 106 | 14.759 | 1.316 | 7.002 | 1.00 8.25 |
| ATOM | 733 | C | GLN | A | 106 | 14.453 | 1.089 | 8.473 | 1.00 8.51 |
| ATOM | 734 | O | GLN | A | 106 | 13.470 | 1.683 | 8.862 | 1.00 6.31 |
| ATOM | 735 | CB | GLN | A | 106 | 14.239 | 0.393 | 5.940 | 1.00 7.45 |
| ATOM | 736 | CG | GLN | A | 106 | 13.184 | -0.528 | 6.465 | 1.00 18.04 |
| ATOM | 737 | CD | GLN | A | 106 | 12.228 | -1.220 | 5.581 | 1.00 16.87 |
| ATOM | 738 | OE1 | GLN | A | 106 | 11.024 | -1.180 | 5.492 | 1.00 17.59 |
| ATOM | 739 | NE2 | GLN | A | 106 | 12.643 | -2.032 | 4.713 | 1.00 8.32 |
| ATOM | 740 | N | GLY | A | 107 | 15.269 | 0.310 | 9.172 | 1.00 7.13 |
| ATOM | 741 | CA | GLY | A | 107 | 15.190 | 0.159 | 10.606 | 1.00 4.61 |
| ATOM | 742 | C | GLY | A | 107 | 15.048 | 1.472 | 11.356 | 1.00 8.27 |
| ATOM | 743 | O | GLY | A | 107 | 14.219 | 1.511 | 12.290 | 1.00 6.52 |
| ATOM | 744 | N | ALA | A | 108 | 15.653 | 2.637 | 11.033 | 1.00 6.44 |
| ATOM | 745 | CA | ALA | A | 108 | 15.266 | 3.864 | 11.641 | 1.00 7.41 |
| ATOM | 746 | C | ALA | A | 108 | 13.813 | 4.346 | 11.471 | 1.00 11.76 |
| ATOM | 747 | O | ALA | A | 108 | 13.150 | 4.914 | 12.298 | 1.00 12.64 |
| ATOM | 748 | CB | ALA | A | 108 | 16.121 | 5.006 | 11.170 | 1.00 13.93 |
| ATOM | 749 | N | ALA | A | 109 | 13.321 | 4.312 | 10.267 | 1.00 9.78 |
| ATOM | 750 | CA | ALA | A | 109 | 12.056 | 4.685 | 9.861 | 1.00 10.47 |
| ATOM | 751 | C | ALA | A | 109 | 11.093 | 3.858 | 10.727 | 1.00 12.32 |
| ATOM | 752 | O | ALA | A | 109 | 10.016 | 4.391 | 11.035 | 1.00 14.67 |
| ATOM | 753 | CB | ALA | A | 109 | 12.035 | 4.173 | 8.456 | 1.00 10.24 |
| ATOM | 754 | N | LEU | A | 110 | 11.259 | 2.690 | 11.077 | 1.00 4.34 |
| ATOM | 755 | CA | LEU | A | 110 | 10.458 | 1.760 | 11.783 | 1.00 11.71 |
| ATOM | 756 | C | LEU | A | 110 | 10.305 | 2.253 | 13.203 | 1.00 15.26 |
| ATOM | 757 | O | LEU | A | 110 | 9.298 | 2.672 | 13.685 | 1.00 18.07 |
| ATOM | 758 | CB | LEU | A | 110 | 11.031 | 0.319 | 11.634 | 1.00 7.52 |
| ATOM | 759 | CG | LEU | A | 110 | 10.247 | -0.801 | 12.258 | 1.00 8.41 |
| ATOM | 760 | CD1 | LEU | A | 110 | 10.685 | -2.233 | 11.862 | 1.00 7.17 |
| ATOM | 761 | CD2 | LEU | A | 110 | 10.278 | -0.659 | 13.783 | 1.00 5.25 |
| ATOM | 762 | N | ILE | A | 111 | 11.397 | 2.373 | 13.907 | 1.00 15.77 |
| ATOM | 763 | CA | ILE | A | 111 | 11.510 | 2.860 | 15.246 | 1.00 12.22 |
| ATOM | 764 | C | ILE | A | 111 | 11.027 | 4.255 | 15.234 | 1.00 9.39 |
| ATOM | 765 | O | ILE | A | 111 | 10.404 | 4.636 | 16.241 | 1.00 12.54 |
| ATOM | 766 | CB | ILE | A | 111 | 12.977 | 2.814 | 15.685 | 1.00 15.55 |
| ATOM | 767 | CG1 | ILE | A | 111 | 13.222 | 1.279 | 15.805 | 1.00 14.19 |

```
ATOM    768  CG2 ILE A 111      13.195   3.465  17.005  1.00   4.64
ATOM    769  CD1 ILE A 111      12.410   0.887  17.002  1.00  14.88
ATOM    770  N   ALA A 112      11.309   5.170  14.341  1.00  11.00
ATOM    771  CA  ALA A 112      10.792   6.528  14.427  1.00  12.45
ATOM    772  C   ALA A 112       9.266   6.455  14.308  1.00  15.59
ATOM    773  O   ALA A 112       8.728   7.131  15.154  1.00  18.13
ATOM    774  CB  ALA A 112      11.334   7.505  13.486  1.00   5.70
ATOM    775  N   ALA A 113       8.575   5.572  13.587  1.00  12.85
ATOM    776  CA  ALA A 113       7.167   5.512  13.557  1.00  15.39
ATOM    777  C   ALA A 113       6.475   5.093  14.861  1.00  18.21
ATOM    778  O   ALA A 113       5.498   5.750  15.226  1.00  14.59
ATOM    779  CB  ALA A 113       6.678   4.562  12.500  1.00  17.63
ATOM    780  N   ALA A 114       6.937   3.948  15.303  1.00  16.02
ATOM    781  CA  ALA A 114       6.483   3.218  16.412  1.00  16.43
ATOM    782  C   ALA A 114       6.578   4.114  17.643  1.00  22.20
ATOM    783  O   ALA A 114       5.673   4.321  18.426  1.00  18.94
ATOM    784  CB  ALA A 114       7.474   2.084  16.565  1.00   4.69
ATOM    785  N   VAL A 115       7.722   4.836  17.744  1.00  22.46
ATOM    786  CA  VAL A 115       7.855   5.499  19.064  1.00  20.88
ATOM    787  C   VAL A 115       6.670   6.469  19.007  1.00  22.71
ATOM    788  O   VAL A 115       6.136   6.761  20.057  1.00  22.05
ATOM    789  CB  VAL A 115       9.279   6.090  19.137  1.00  19.61
ATOM    790  CG1 VAL A 115       9.396   7.259  20.122  1.00   8.35
ATOM    791  CG2 VAL A 115      10.245   5.016  19.562  1.00  13.91
ATOM    792  N   SER A 116       6.467   7.085  17.828  1.00  23.59
ATOM    793  CA  SER A 116       5.539   8.172  17.736  1.00  23.68
ATOM    794  C   SER A 116       4.169   7.647  18.120  1.00  23.77
ATOM    795  O   SER A 116       3.333   8.523  18.399  1.00  27.35
ATOM    796  CB  SER A 116       5.522   8.865  16.376  1.00  25.21
ATOM    797  OG  SER A 116       5.168   8.043  15.277  1.00  28.05
ATOM    798  N   GLU A 117       3.859   6.397  18.004  1.00  18.83
ATOM    799  CA  GLU A 117       2.491   6.020  18.238  1.00  22.21
ATOM    800  C   GLU A 117       2.461   5.474  19.653  1.00  30.46
ATOM    801  O   GLU A 117       1.487   4.773  19.863  1.00  35.72
ATOM    802  CB  GLU A 117       1.977   4.902  17.343  1.00  21.63
ATOM    803  CG  GLU A 117       2.167   5.219  15.897  1.00  26.41
ATOM    804  CD  GLU A 117       1.560   4.424  14.814  1.00  34.01
ATOM    805  OE1 GLU A 117       0.912   3.440  15.046  1.00  32.59
ATOM    806  OE2 GLU A 117       1.750   4.833  13.659  1.00  44.62
ATOM    807  N   LEU A 118       3.438   5.570  20.512  1.00  34.45
ATOM    808  CA  LEU A 118       3.326   5.006  21.812  1.00  33.64
ATOM    809  C   LEU A 118       2.681   6.110  22.633  1.00  41.75
ATOM    810  O   LEU A 118       2.594   7.267  22.370  1.00  39.90
ATOM    811  CB  LEU A 118       4.600   4.668  22.392  1.00  29.44
ATOM    812  CG  LEU A 118       5.628   3.891  21.645  1.00  26.36
ATOM    813  CD1 LEU A 118       6.921   3.840  22.379  1.00  27.53
ATOM    814  CD2 LEU A 118       5.110   2.520  21.536  1.00  20.69
ATOM    815  N   SER A 119       2.076   5.794  23.726  1.00  48.86
```

| | | | | | | | | | |
|---|---|---|---|---|---|---|---|---|---|
| ATOM | 816 | CA | SER | A | 119 | 0.910 | 5.647 | 24.476 | 1.00 52.44 |
| ATOM | 817 | C | SER | A | 119 | 1.212 | 6.063 | 25.866 | 1.00 52.57 |
| ATOM | 818 | O | SER | A | 119 | 1.485 | 5.258 | 26.735 | 1.00 55.54 |
| ATOM | 819 | CB | SER | A | 119 | 0.550 | 4.132 | 24.488 | 1.00 70.55 |
| ATOM | 820 | OG | SER | A | 119 | 1.393 | 3.091 | 23.908 | 1.00 66.80 |
| ATOM | 821 | N | GLY | A | 120 | 1.532 | 7.307 | 26.024 | 1.00 52.95 |
| ATOM | 822 | CA | GLY | A | 120 | 1.910 | 7.761 | 27.382 | 1.00 53.35 |
| ATOM | 823 | C | GLY | A | 120 | 2.944 | 7.109 | 28.291 | 1.00 49.09 |
| ATOM | 824 | O | GLY | A | 120 | 4.086 | 7.617 | 28.358 | 1.00 49.66 |
| ATOM | 825 | N | ALA | A | 121 | 2.526 | 6.129 | 29.102 | 1.00 42.97 |
| ATOM | 826 | CA | ALA | A | 121 | 3.477 | 5.574 | 30.022 | 1.00 40.72 |
| ATOM | 827 | C | ALA | A | 121 | 4.587 | 4.772 | 29.326 | 1.00 44.20 |
| ATOM | 828 | O | ALA | A | 121 | 5.749 | 4.803 | 29.711 | 1.00 45.42 |
| ATOM | 829 | CB | ALA | A | 121 | 2.965 | 4.542 | 30.903 | 1.00 36.34 |
| ATOM | 830 | N | VAL | A | 122 | 4.122 | 4.035 | 28.312 | 1.00 41.15 |
| ATOM | 831 | CA | VAL | A | 122 | 5.090 | 3.269 | 27.548 | 1.00 33.41 |
| ATOM | 832 | C | VAL | A | 122 | 5.870 | 4.168 | 26.652 | 1.00 28.48 |
| ATOM | 833 | O | VAL | A | 122 | 7.084 | 4.019 | 26.872 | 1.00 27.69 |
| ATOM | 834 | CB | VAL | A | 122 | 4.424 | 2.056 | 26.952 | 1.00 30.22 |
| ATOM | 835 | CG1 | VAL | A | 122 | 2.924 | 1.997 | 27.098 | 1.00 28.03 |
| ATOM | 836 | CG2 | VAL | A | 122 | 4.891 | 1.836 | 25.551 | 1.00 23.22 |
| ATOM | 837 | N | LYS | A | 123 | 5.424 | 5.310 | 26.177 | 1.00 23.16 |
| ATOM | 838 | CA | LYS | A | 123 | 6.354 | 6.314 | 25.661 | 1.00 23.11 |
| ATOM | 839 | C | LYS | A | 123 | 7.403 | 6.783 | 26.661 | 1.00 25.28 |
| ATOM | 840 | O | LYS | A | 123 | 8.524 | 7.224 | 26.449 | 1.00 29.01 |
| ATOM | 841 | CB | LYS | A | 123 | 5.561 | 7.502 | 25.100 | 1.00 23.54 |
| ATOM | 842 | CG | LYS | A | 123 | 6.171 | 8.573 | 24.277 | 1.00 26.71 |
| ATOM | 843 | CD | LYS | A | 123 | 5.400 | 9.775 | 23.888 | 1.00 43.07 |
| ATOM | 844 | CE | LYS | A | 123 | 4.953 | 9.783 | 22.461 | 1.00 59.59 |
| ATOM | 845 | NZ | LYS | A | 123 | 3.518 | 9.637 | 22.099 | 1.00 67.50 |
| ATOM | 846 | N | GLU | A | 124 | 6.977 | 6.991 | 27.918 | 1.00 27.95 |
| ATOM | 847 | CA | GLU | A | 124 | 7.845 | 7.700 | 28.863 | 1.00 27.29 |
| ATOM | 848 | C | GLU | A | 124 | 8.910 | 6.706 | 29.243 | 1.00 25.21 |
| ATOM | 849 | O | GLU | A | 124 | 9.993 | 7.165 | 29.769 | 1.00 21.21 |
| ATOM | 850 | CB | GLU | A | 124 | 6.986 | 8.351 | 29.927 | 1.00 40.13 |
| ATOM | 851 | CG | GLU | A | 124 | 7.588 | 8.609 | 31.295 | 1.00 57.40 |
| ATOM | 852 | CD | GLU | A | 124 | 8.530 | 9.814 | 31.247 | 1.00 66.99 |
| ATOM | 853 | OE1 | GLU | A | 124 | 9.619 | 9.751 | 31.902 | 1.00 70.44 |
| ATOM | 854 | OE2 | GLU | A | 124 | 7.949 | 10.652 | 30.502 | 1.00 73.84 |
| ATOM | 855 | N | GLN | A | 125 | 8.656 | 5.393 | 29.058 | 1.00 19.93 |
| ATOM | 856 | CA | GLN | A | 125 | 9.761 | 4.509 | 29.546 | 1.00 17.98 |
| ATOM | 857 | C | GLN | A | 125 | 10.865 | 4.556 | 28.521 | 1.00 24.28 |
| ATOM | 858 | O | GLN | A | 125 | 11.964 | 4.107 | 28.815 | 1.00 21.47 |
| ATOM | 859 | CB | GLN | A | 125 | 9.225 | 3.178 | 29.844 | 1.00 9.13 |
| ATOM | 860 | CG | GLN | A | 125 | 9.901 | 2.001 | 30.299 | 1.00 9.05 |
| ATOM | 861 | CD | GLN | A | 125 | 9.211 | 0.719 | 30.129 | 1.00 19.33 |
| ATOM | 862 | OE1 | GLN | A | 125 | 8.190 | 0.703 | 29.466 | 1.00 28.52 |
| ATOM | 863 | NE2 | GLN | A | 125 | 9.662 | -0.396 | 30.684 | 1.00 13.34 |

| ATOM | 864 | N   | VAL | A | 126 | 10.593 | 5.188 | 27.319 | 1.00 | 25.30 |
| ATOM | 865 | CA  | VAL | A | 126 | 11.738 | 5.124 | 26.361 | 1.00 | 22.55 |
| ATOM | 866 | C   | VAL | A | 126 | 12.546 | 6.334 | 26.614 | 1.00 | 17.55 |
| ATOM | 867 | O   | VAL | A | 126 | 12.109 | 7.408 | 26.329 | 1.00 | 12.79 |
| ATOM | 868 | CB  | VAL | A | 126 | 11.227 | 4.560 | 25.022 | 1.00 | 23.76 |
| ATOM | 869 | CG1 | VAL | A | 126 | 9.706  | 4.686 | 24.946 | 1.00 | 23.77 |
| ATOM | 870 | CG2 | VAL | A | 126 | 11.795 | 5.081 | 23.743 | 1.00 | 23.81 |
| ATOM | 871 | N   | LYS | A | 127 | 13.726 | 6.233 | 27.264 | 1.00 | 16.41 |
| ATOM | 872 | CA  | LYS | A | 127 | 14.462 | 7.494 | 27.639 | 1.00 | 18.18 |
| ATOM | 873 | C   | LYS | A | 127 | 15.239 | 8.063 | 26.488 | 1.00 | 18.49 |
| ATOM | 874 | O   | LYS | A | 127 | 15.812 | 9.103 | 26.680 | 1.00 | 18.99 |
| ATOM | 875 | CB  | LYS | A | 127 | 15.401 | 7.148 | 28.792 | 1.00 | 20.81 |
| ATOM | 876 | CG  | LYS | A | 127 | 14.770 | 6.110 | 29.713 | 1.00 | 21.99 |
| ATOM | 877 | CD  | LYS | A | 127 | 13.435 | 6.726 | 30.064 | 1.00 | 33.86 |
| ATOM | 878 | CE  | LYS | A | 127 | 12.779 | 6.612 | 31.399 | 1.00 | 32.17 |
| ATOM | 879 | NZ  | LYS | A | 127 | 12.279 | 7.863 | 31.993 | 1.00 | 45.34 |
| ATOM | 880 | N   | GLY | A | 128 | 15.522 | 7.281 | 25.416 | 1.00 | 20.56 |
| ATOM | 881 | CA  | GLY | A | 128 | 16.280 | 7.948 | 24.306 | 1.00 | 20.72 |
| ATOM | 882 | C   | GLY | A | 128 | 16.358 | 7.104 | 23.063 | 1.00 | 17.71 |
| ATOM | 883 | O   | GLY | A | 128 | 16.168 | 5.901 | 23.226 | 1.00 | 16.66 |
| ATOM | 884 | N   | VAL | A | 129 | 16.451 | 7.725 | 21.892 | 1.00 | 16.16 |
| ATOM | 885 | CA  | VAL | A | 129 | 16.497 | 6.872 | 20.691 | 1.00 | 13.82 |
| ATOM | 886 | C   | VAL | A | 129 | 17.519 | 7.371 | 19.719 | 1.00 | 8.35  |
| ATOM | 887 | O   | VAL | A | 129 | 17.602 | 8.553 | 19.556 | 1.00 | 2.85  |
| ATOM | 888 | CB  | VAL | A | 129 | 15.192 | 6.426 | 20.054 | 1.00 | 11.02 |
| ATOM | 889 | CG1 | VAL | A | 129 | 14.007 | 7.041 | 20.726 | 1.00 | 6.50  |
| ATOM | 890 | CG2 | VAL | A | 129 | 15.051 | 6.729 | 18.571 | 1.00 | 10.03 |
| ATOM | 891 | N   | ALA | A | 130 | 18.455 | 6.398 | 19.363 | 1.00 | 8.05  |
| ATOM | 892 | CA  | ALA | A | 130 | 19.430 | 6.845 | 18.344 | 1.00 | 7.55  |
| ATOM | 893 | C   | ALA | A | 130 | 19.078 | 6.293 | 16.958 | 1.00 | 11.17 |
| ATOM | 894 | O   | ALA | A | 130 | 18.755 | 5.145 | 16.849 | 1.00 | 15.74 |
| ATOM | 895 | CB  | ALA | A | 130 | 20.781 | 6.391 | 18.603 | 1.00 | 5.89  |
| ATOM | 896 | N   | LEU | A | 131 | 18.911 | 6.953 | 15.892 | 1.00 | 7.36  |
| ATOM | 897 | CA  | LEU | A | 131 | 18.635 | 6.625 | 14.553 | 1.00 | 7.70  |
| ATOM | 898 | C   | LEU | A | 131 | 19.876 | 6.908 | 13.661 | 1.00 | 12.02 |
| ATOM | 899 | O   | LEU | A | 131 | 20.436 | 8.033 | 13.604 | 1.00 | 6.80  |
| ATOM | 900 | CB  | LEU | A | 131 | 17.604 | 7.713 | 14.102 | 1.00 | 8.40  |
| ATOM | 901 | CG  | LEU | A | 131 | 16.160 | 7.830 | 14.575 | 1.00 | 6.67  |
| ATOM | 902 | CD1 | LEU | A | 131 | 15.391 | 8.957 | 13.981 | 1.00 | 4.49  |
| ATOM | 903 | CD2 | LEU | A | 131 | 15.481 | 6.488 | 14.324 | 1.00 | 5.12  |
| ATOM | 904 | N   | PHE | A | 132 | 20.271 | 6.009 | 12.802 | 1.00 | 11.56 |
| ATOM | 905 | CA  | PHE | A | 132 | 21.422 | 6.183 | 11.908 | 1.00 | 10.44 |
| ATOM | 906 | C   | PHE | A | 132 | 20.965 | 6.013 | 10.478 | 1.00 | 8.46  |
| ATOM | 907 | O   | PHE | A | 132 | 20.175 | 5.101 | 10.097 | 1.00 | 11.04 |
| ATOM | 908 | CB  | PHE | A | 132 | 22.217 | 4.931 | 12.282 | 1.00 | 10.56 |
| ATOM | 909 | CG  | PHE | A | 132 | 22.693 | 4.830 | 13.714 | 1.00 | 16.38 |
| ATOM | 910 | CD1 | PHE | A | 132 | 21.951 | 4.029 | 14.542 | 1.00 | 13.36 |
| ATOM | 911 | CD2 | PHE | A | 132 | 23.860 | 5.489 | 14.213 | 1.00 | 15.12 |

| ATOM | 912 | CE1 | PHE | A | 132 | 22.342 | 3.911 | 15.889 | 1.00 | 14.91 |
| ATOM | 913 | CE2 | PHE | A | 132 | 24.176 | 5.323 | 15.513 | 1.00 | 18.02 |
| ATOM | 914 | CZ | PHE | A | 132 | 23.426 | 4.530 | 16.403 | 1.00 | 15.09 |
| ATOM | 915 | N | GLY | A | 133 | 21.431 | 6.876 | 9.580 | 1.00 | 7.35 |
| ATOM | 916 | CA | GLY | A | 133 | 21.026 | 6.893 | 8.148 | 1.00 | 5.86 |
| ATOM | 917 | C | GLY | A | 133 | 19.503 | 6.919 | 8.061 | 1.00 | 12.25 |
| ATOM | 918 | O | GLY | A | 133 | 18.890 | 5.926 | 7.593 | 1.00 | 9.03 |
| ATOM | 919 | N | TYR | A | 134 | 18.926 | 8.070 | 8.532 | 1.00 | 9.85 |
| ATOM | 920 | CA | TYR | A | 134 | 17.455 | 8.022 | 8.838 | 1.00 | 7.40 |
| ATOM | 921 | C | TYR | A | 134 | 16.647 | 8.365 | 7.584 | 1.00 | 10.61 |
| ATOM | 922 | O | TYR | A | 134 | 16.785 | 9.513 | 7.131 | 1.00 | 5.85 |
| ATOM | 923 | CB | TYR | A | 134 | 17.161 | 9.128 | 9.836 | 1.00 | 7.27 |
| ATOM | 924 | CG | TYR | A | 134 | 15.842 | 9.393 | 10.391 | 1.00 | 7.89 |
| ATOM | 925 | CD1 | TYR | A | 134 | 14.889 | 8.437 | 10.312 | 1.00 | 6.65 |
| ATOM | 926 | CD2 | TYR | A | 134 | 15.661 | 10.651 | 10.948 | 1.00 | 11.44 |
| ATOM | 927 | CE1 | TYR | A | 134 | 13.657 | 8.690 | 10.821 | 1.00 | 9.05 |
| ATOM | 928 | CE2 | TYR | A | 134 | 14.408 | 10.928 | 11.467 | 1.00 | 12.89 |
| ATOM | 929 | CZ | TYR | A | 134 | 13.428 | 9.923 | 11.423 | 1.00 | 14.22 |
| ATOM | 930 | OH | TYR | A | 134 | 12.146 | 10.110 | 11.975 | 1.00 | 12.41 |
| ATOM | 931 | N | THR | A | 135 | 15.811 | 7.398 | 7.139 | 1.00 | 11.51 |
| ATOM | 932 | CA | THR | A | 135 | 15.229 | 7.581 | 5.789 | 1.00 | 7.71 |
| ATOM | 933 | C | THR | A | 135 | 14.082 | 8.530 | 5.825 | 1.00 | 10.36 |
| ATOM | 934 | O | THR | A | 135 | 13.845 | 8.878 | 4.727 | 1.00 | 11.26 |
| ATOM | 935 | CB | THR | A | 135 | 14.772 | 6.394 | 4.967 | 1.00 | 12.02 |
| ATOM | 936 | OG1 | THR | A | 135 | 13.821 | 5.399 | 5.398 | 1.00 | 22.81 |
| ATOM | 937 | CG2 | THR | A | 135 | 15.828 | 5.332 | 4.712 | 1.00 | 14.88 |
| ATOM | 938 | N | GLN | A | 136 | 13.632 | 9.105 | 6.928 | 1.00 | 15.28 |
| ATOM | 939 | CA | GLN | A | 136 | 12.596 | 10.134 | 6.968 | 1.00 | 16.48 |
| ATOM | 940 | C | GLN | A | 136 | 13.102 | 11.418 | 7.646 | 1.00 | 17.46 |
| ATOM | 941 | O | GLN | A | 136 | 12.292 | 12.231 | 8.035 | 1.00 | 12.82 |
| ATOM | 942 | CB | GLN | A | 136 | 11.336 | 9.671 | 7.701 | 1.00 | 5.71 |
| ATOM | 943 | CG | GLN | A | 136 | 11.178 | 8.191 | 7.263 | 1.00 | 13.60 |
| ATOM | 944 | CD | GLN | A | 136 | 10.504 | 8.264 | 5.932 | 1.00 | 14.65 |
| ATOM | 945 | OE1 | GLN | A | 136 | 9.587 | 9.102 | 5.986 | 1.00 | 23.99 |
| ATOM | 946 | NE2 | GLN | A | 136 | 10.852 | 7.529 | 4.914 | 1.00 | 14.68 |
| ATOM | 947 | N | ASN | A | 137 | 14.421 | 11.532 | 7.566 | 1.00 | 18.52 |
| ATOM | 948 | CA | ASN | A | 137 | 14.953 | 12.752 | 8.141 | 1.00 | 18.16 |
| ATOM | 949 | C | ASN | A | 137 | 14.301 | 13.929 | 7.458 | 1.00 | 19.79 |
| ATOM | 950 | O | ASN | A | 137 | 13.895 | 14.802 | 8.157 | 1.00 | 12.28 |
| ATOM | 951 | CB | ASN | A | 137 | 16.481 | 12.573 | 8.239 | 1.00 | 14.17 |
| ATOM | 952 | CG | ASN | A | 137 | 17.247 | 13.740 | 8.812 | 1.00 | 19.75 |
| ATOM | 953 | OD1 | ASN | A | 137 | 17.821 | 14.341 | 7.934 | 1.00 | 14.52 |
| ATOM | 954 | ND2 | ASN | A | 137 | 17.390 | 14.130 | 10.042 | 1.00 | 17.43 |
| ATOM | 955 | N | LEU | A | 138 | 14.180 | 14.062 | 6.141 | 1.00 | 27.31 |
| ATOM | 956 | CA | LEU | A | 138 | 13.640 | 15.270 | 5.553 | 1.00 | 25.53 |
| ATOM | 957 | C | LEU | A | 138 | 12.190 | 15.332 | 5.971 | 1.00 | 22.45 |
| ATOM | 958 | O | LEU | A | 138 | 11.710 | 16.281 | 6.549 | 1.00 | 25.13 |
| ATOM | 959 | CB | LEU | A | 138 | 13.632 | 15.269 | 4.056 | 1.00 | 41.28 |

| | | | | | | | | |
|---|---|---|---|---|---|---|---|---|
| ATOM | 960 | CG | LEU | A | 138 | 13.713 | 16.582 | 3.303 | 1.00 31.76 |
| ATOM | 961 | CD1 | LEU | A | 138 | 14.641 | 17.503 | 4.012 | 1.00 51.09 |
| ATOM | 962 | CD2 | LEU | A | 138 | 14.207 | 16.573 | 1.958 | 1.00 46.20 |
| ATOM | 963 | N | GLN | A | 139 | 11.378 | 14.403 | 5.569 | 1.00 20.48 |
| ATOM | 964 | CA | GLN | A | 139 | 10.034 | 14.390 | 6.037 | 1.00 19.98 |
| ATOM | 965 | C | GLN | A | 139 | 9.846 | 14.749 | 7.471 | 1.00 22.85 |
| ATOM | 966 | O | GLN | A | 139 | 8.791 | 15.282 | 7.528 | 1.00 26.66 |
| ATOM | 967 | CB | GLN | A | 139 | 9.517 | 12.969 | 5.899 | 1.00 18.37 |
| ATOM | 968 | CG | GLN | A | 139 | 9.684 | 12.643 | 4.450 | 1.00 22.02 |
| ATOM | 969 | CD | GLN | A | 139 | 10.984 | 11.983 | 4.110 | 1.00 22.69 |
| ATOM | 970 | OE1 | GLN | A | 139 | 10.674 | 10.980 | 3.477 | 1.00 35.62 |
| ATOM | 971 | NE2 | GLN | A | 139 | 12.195 | 12.405 | 4.410 | 1.00 31.70 |
| ATOM | 972 | N | ASN | A | 140 | 10.454 | 14.072 | 8.427 | 1.00 26.14 |
| ATOM | 973 | CA | ASN | A | 140 | 10.215 | 14.183 | 9.848 | 1.00 19.06 |
| ATOM | 974 | C | ASN | A | 140 | 10.941 | 15.429 | 10.293 | 1.00 16.99 |
| ATOM | 975 | O | ASN | A | 140 | 11.040 | 15.654 | 11.454 | 1.00 18.05 |
| ATOM | 976 | CB | ASN | A | 140 | 10.581 | 12.910 | 10.541 | 1.00 17.20 |
| ATOM | 977 | CG | ASN | A | 140 | 9.465 | 11.998 | 10.210 | 1.00 16.28 |
| ATOM | 978 | OD1 | ASN | A | 140 | 8.615 | 12.565 | 9.563 | 1.00 23.57 |
| ATOM | 979 | ND2 | ASN | A | 140 | 9.460 | 10.756 | 10.630 | 1.00 22.65 |
| ATOM | 980 | N | ARG | A | 141 | 11.457 | 16.162 | 9.397 | 1.00 19.20 |
| ATOM | 981 | CA | ARG | A | 141 | 12.170 | 17.350 | 9.790 | 1.00 26.25 |
| ATOM | 982 | C | ARG | A | 141 | 13.219 | 17.090 | 10.818 | 1.00 25.06 |
| ATOM | 983 | O | ARG | A | 141 | 13.365 | 17.928 | 11.649 | 1.00 27.60 |
| ATOM | 984 | CB | ARG | A | 141 | 11.123 | 18.299 | 10.271 | 1.00 37.72 |
| ATOM | 985 | CG | ARG | A | 141 | 10.083 | 18.974 | 9.372 | 1.00 49.61 |
| ATOM | 986 | N | GLY | A | 142 | 14.110 | 16.165 | 10.920 | 1.00 19.42 |
| ATOM | 987 | CA | GLY | A | 142 | 14.997 | 15.778 | 11.902 | 1.00 14.21 |
| ATOM | 988 | C | GLY | A | 142 | 14.652 | 15.066 | 13.158 | 1.00 19.42 |
| ATOM | 989 | O | GLY | A | 142 | 15.547 | 14.759 | 13.971 | 1.00 23.74 |
| ATOM | 990 | N | GLY | A | 143 | 13.354 | 14.851 | 13.569 | 1.00 14.09 |
| ATOM | 991 | CA | GLY | A | 143 | 13.210 | 14.075 | 14.757 | 1.00 11.80 |
| ATOM | 992 | C | GLY | A | 143 | 12.203 | 12.972 | 14.555 | 1.00 16.69 |
| ATOM | 993 | O | GLY | A | 143 | 11.760 | 12.787 | 13.481 | 1.00 19.57 |
| ATOM | 994 | N | ILE | A | 144 | 11.668 | 12.386 | 15.590 | 1.00 19.71 |
| ATOM | 995 | CA | ILE | A | 144 | 10.494 | 11.589 | 15.667 | 1.00 20.13 |
| ATOM | 996 | C | ILE | A | 144 | 9.313 | 12.315 | 16.296 | 1.00 27.00 |
| ATOM | 997 | O | ILE | A | 144 | 9.298 | 13.026 | 17.268 | 1.00 26.75 |
| ATOM | 998 | CB | ILE | A | 144 | 10.973 | 10.583 | 16.692 | 1.00 16.84 |
| ATOM | 999 | CG1 | ILE | A | 144 | 12.363 | 9.956 | 16.348 | 1.00 5.60 |
| ATOM | 1000 | CG2 | ILE | A | 144 | 9.882 | 9.636 | 16.775 | 1.00 14.01 |
| ATOM | 1001 | CD1 | ILE | A | 144 | 12.437 | 9.156 | 17.562 | 1.00 2.75 |
| ATOM | 1002 | N | PRO | A | 145 | 8.249 | 12.380 | 15.499 | 1.00 32.77 |
| ATOM | 1003 | CA | PRO | A | 145 | 6.959 | 12.993 | 15.779 | 1.00 29.89 |
| ATOM | 1004 | C | PRO | A | 145 | 6.484 | 12.588 | 17.180 | 1.00 27.78 |
| ATOM | 1005 | O | PRO | A | 145 | 6.475 | 11.446 | 17.537 | 1.00 26.07 |
| ATOM | 1006 | CB | PRO | A | 145 | 5.957 | 12.384 | 14.784 | 1.00 26.51 |
| ATOM | 1007 | CG | PRO | A | 145 | 6.887 | 12.059 | 13.668 | 1.00 25.85 |

```
ATOM   1008  CD   PRO A 145       8.174  11.563  14.234  1.00  31.33
ATOM   1009  N    ASN A 146       5.796  13.462  17.878  1.00  27.07
ATOM   1010  CA   ASN A 146       5.454  13.274  19.230  1.00  28.59
ATOM   1011  C    ASN A 146       6.526  12.605  20.045  1.00  29.25
ATOM   1012  O    ASN A 146       6.087  11.995  20.996  1.00  35.51
ATOM   1013  CB   ASN A 146       4.285  12.364  19.230  1.00  41.13
ATOM   1014  CG   ASN A 146       3.300  12.568  18.120  1.00  48.43
ATOM   1015  OD1  ASN A 146       3.134  13.721  17.788  1.00  49.24
ATOM   1016  ND2  ASN A 146       2.763  11.437  17.695  1.00  47.79
ATOM   1017  N    TYR A 147       7.791  12.799  19.885  1.00  23.88
ATOM   1018  CA   TYR A 147       8.689  12.339  20.969  1.00  21.90
ATOM   1019  C    TYR A 147       9.583  13.495  21.285  1.00  22.57
ATOM   1020  O    TYR A 147       9.777  14.399  20.494  1.00  26.53
ATOM   1021  CB   TYR A 147       9.309  11.098  20.498  1.00  21.16
ATOM   1022  CG   TYR A 147      10.285  10.471  21.349  1.00  20.45
ATOM   1023  CD1  TYR A 147       9.882   9.720  22.384  1.00  24.28
ATOM   1024  CD2  TYR A 147      11.608  10.564  21.189  1.00  17.96
ATOM   1025  CE1  TYR A 147      10.681   9.029  23.273  1.00  24.55
ATOM   1026  CE2  TYR A 147      12.509   9.948  21.983  1.00  20.73
ATOM   1027  CZ   TYR A 147      12.022   9.184  23.030  1.00  24.61
ATOM   1028  OH   TYR A 147      12.891   8.536  23.887  1.00  24.80
ATOM   1029  N    PRO A 148       9.893  13.858  22.507  1.00  22.86
ATOM   1030  CA   PRO A 148      10.817  14.916  22.769  1.00  21.77
ATOM   1031  C    PRO A 148      12.127  14.882  21.957  1.00  22.49
ATOM   1032  O    PRO A 148      13.007  14.004  22.117  1.00  22.31
ATOM   1033  CB   PRO A 148      11.185  14.694  24.251  1.00  23.23
ATOM   1034  CG   PRO A 148      10.324  13.576  24.719  1.00  23.39
ATOM   1035  CD   PRO A 148       9.677  12.889  23.590  1.00  25.33
ATOM   1036  N    ARG A 149      12.432  15.980  21.250  1.00  25.45
ATOM   1037  CA   ARG A 149      13.735  16.138  20.567  1.00  22.54
ATOM   1038  C    ARG A 149      14.910  16.018  21.499  1.00  21.28
ATOM   1039  O    ARG A 149      15.860  15.477  21.015  1.00  16.61
ATOM   1040  CB   ARG A 149      13.829  17.346  19.727  1.00  31.02
ATOM   1041  CG   ARG A 149      12.837  17.750  18.719  1.00  58.26
ATOM   1042  CD   ARG A 149      13.452  18.605  17.658  1.00  80.58
ATOM   1043  NE   ARG A 149      13.769  17.798  16.491  1.00  92.05
ATOM   1044  CZ   ARG A 149      13.315  18.154  15.320  1.00  91.85
ATOM   1045  NH1  ARG A 149      12.586  19.213  15.165  1.00  86.98
ATOM   1046  NH2  ARG A 149      13.544  17.488  14.242  1.00  91.61
ATOM   1047  N    GLU A 150      14.813  16.282  22.825  1.00  28.09
ATOM   1048  CA   GLU A 150      15.950  16.171  23.735  1.00  25.55
ATOM   1049  C    GLU A 150      16.272  14.736  24.020  1.00  21.12
ATOM   1050  O    GLU A 150      17.372  14.443  24.371  1.00  24.39
ATOM   1051  CB   GLU A 150      15.753  17.040  24.917  1.00  38.73
ATOM   1052  CG   GLU A 150      14.328  17.370  25.359  1.00  67.27
ATOM   1053  CD   GLU A 150      14.252  17.185  26.899  1.00  85.05
ATOM   1054  OE1  GLU A 150      15.005  17.890  27.657  1.00  90.70
ATOM   1055  OE2  GLU A 150      13.454  16.321  27.373  1.00  91.68
```

| | | | | | | | | |
|---|---|---|---|---|---|---|---|---|
| ATOM | 1056 | N   | ARG | A 151 | 15.396 | 13.807 | 23.727 | 1.00 19.70 |
| ATOM | 1057 | CA  | ARG | A 151 | 15.752 | 12.424 | 23.844 | 1.00 19.52 |
| ATOM | 1058 | C   | ARG | A 151 | 16.163 | 11.779 | 22.531 | 1.00 19.28 |
| ATOM | 1059 | O   | ARG | A 151 | 16.373 | 10.586 | 22.480 | 1.00 14.55 |
| ATOM | 1060 | CB  | ARG | A 151 | 14.548 | 11.796 | 24.412 | 1.00 23.06 |
| ATOM | 1061 | CG  | ARG | A 151 | 13.853 | 12.432 | 25.516 | 1.00 22.24 |
| ATOM | 1062 | CD  | ARG | A 151 | 13.200 | 11.451 | 26.393 | 1.00 33.40 |
| ATOM | 1063 | NE  | ARG | A 151 | 12.609 | 11.893 | 27.633 | 1.00 46.53 |
| ATOM | 1064 | CZ  | ARG | A 151 | 11.796 | 11.028 | 28.275 | 1.00 52.87 |
| ATOM | 1065 | NH1 | ARG | A 151 | 11.428 |  9.823 | 27.930 | 1.00 51.02 |
| ATOM | 1066 | NH2 | ARG | A 151 | 11.203 | 11.278 | 29.416 | 1.00 59.98 |
| ATOM | 1067 | N   | THR | A 152 | 16.360 | 12.526 | 21.505 | 1.00 14.12 |
| ATOM | 1068 | CA  | THR | A 152 | 16.629 | 11.925 | 20.253 | 1.00 15.05 |
| ATOM | 1069 | C   | THR | A 152 | 17.995 | 12.249 | 19.745 | 1.00 17.30 |
| ATOM | 1070 | O   | THR | A 152 | 18.282 | 13.373 | 19.965 | 1.00 21.34 |
| ATOM | 1071 | CB  | THR | A 152 | 15.680 | 12.408 | 19.158 | 1.00 13.91 |
| ATOM | 1072 | OG1 | THR | A 152 | 14.423 | 12.256 | 19.858 | 1.00 23.92 |
| ATOM | 1073 | CG2 | THR | A 152 | 15.737 | 11.934 | 17.759 | 1.00  6.77 |
| ATOM | 1074 | N   | LYS | A 153 | 18.704 | 11.336 | 19.121 | 1.00 15.49 |
| ATOM | 1075 | CA  | LYS | A 153 | 19.930 | 11.725 | 18.450 | 1.00 17.73 |
| ATOM | 1076 | C   | LYS | A 153 | 19.893 | 11.035 | 17.073 | 1.00 18.41 |
| ATOM | 1077 | O   | LYS | A 153 | 19.866 |  9.800 | 17.121 | 1.00 16.04 |
| ATOM | 1078 | CB  | LYS | A 153 | 21.112 | 11.260 | 19.338 | 1.00 14.55 |
| ATOM | 1079 | CG  | LYS | A 153 | 22.523 | 11.508 | 18.933 | 1.00 11.95 |
| ATOM | 1080 | CD  | LYS | A 153 | 22.883 | 12.882 | 19.403 | 1.00 40.35 |
| ATOM | 1081 | CE  | LYS | A 153 | 24.358 | 13.093 | 19.079 | 1.00 62.12 |
| ATOM | 1082 | NZ  | LYS | A 153 | 24.930 | 14.235 | 19.863 | 1.00 73.03 |
| ATOM | 1083 | N   | VAL | A 154 | 19.910 | 11.962 | 16.136 | 1.00 15.86 |
| ATOM | 1084 | CA  | VAL | A 154 | 20.031 | 11.508 | 14.730 | 1.00 15.79 |
| ATOM | 1085 | C   | VAL | A 154 | 21.406 | 11.481 | 14.040 | 1.00 13.11 |
| ATOM | 1086 | O   | VAL | A 154 | 21.958 | 12.460 | 13.675 | 1.00 13.51 |
| ATOM | 1087 | CB  | VAL | A 154 | 19.095 | 12.257 | 13.674 | 1.00  5.90 |
| ATOM | 1088 | CG1 | VAL | A 154 | 19.276 | 11.765 | 12.247 | 1.00  8.45 |
| ATOM | 1089 | CG2 | VAL | A 154 | 17.672 | 12.091 | 14.117 | 1.00  7.14 |
| ATOM | 1090 | N   | PHE | A 155 | 22.039 | 10.448 | 13.605 | 1.00 13.75 |
| ATOM | 1091 | CA  | PHE | A 155 | 23.263 | 10.473 | 12.843 | 1.00 10.67 |
| ATOM | 1092 | C   | PHE | A 155 | 22.906 | 10.406 | 11.402 | 1.00 11.64 |
| ATOM | 1093 | O   | PHE | A 155 | 22.505 |  9.367 | 10.893 | 1.00 15.09 |
| ATOM | 1094 | CB  | PHE | A 155 | 23.955 |  9.120 | 13.304 | 1.00  5.38 |
| ATOM | 1095 | CG  | PHE | A 155 | 24.396 |  9.266 | 14.739 | 1.00 16.52 |
| ATOM | 1096 | CD1 | PHE | A 155 | 23.678 |  8.642 | 15.696 | 1.00 23.70 |
| ATOM | 1097 | CD2 | PHE | A 155 | 25.503 |  9.950 | 15.107 | 1.00 11.27 |
| ATOM | 1098 | CE1 | PHE | A 155 | 24.037 |  8.702 | 17.011 | 1.00 23.25 |
| ATOM | 1099 | CE2 | PHE | A 155 | 25.888 |  9.994 | 16.372 | 1.00  7.37 |
| ATOM | 1100 | CZ  | PHE | A 155 | 25.139 |  9.384 | 17.357 | 1.00 16.13 |
| ATOM | 1101 | N   | CYS | A 156 | 23.205 | 11.255 | 10.511 | 1.00 12.38 |
| ATOM | 1102 | CA  | CYS | A 156 | 22.847 | 11.443 |  9.114 | 1.00 11.64 |
| ATOM | 1103 | C   | CYS | A 156 | 24.057 | 12.027 |  8.461 | 1.00 10.08 |

| ATOM | 1104 | O   | CYS A 156 | 24.385 | 13.174 | 8.378  | 1.00 | 13.73 |
|------|------|-----|-----------|--------|--------|--------|------|-------|
| ATOM | 1105 | CB  | CYS A 156 | 21.575 | 12.391 | 8.917  | 1.00 | 6.30  |
| ATOM | 1106 | SG  | CYS A 156 | 20.137 | 11.470 | 8.287  | 1.00 | 10.60 |
| ATOM | 1107 | N   | ASN A 157 | 24.814 | 11.147 | 7.918  | 1.00 | 16.95 |
| ATOM | 1108 | CA  | ASN A 157 | 26.229 | 11.665 | 7.576  | 1.00 | 19.16 |
| ATOM | 1109 | C   | ASN A 157 | 26.197 | 12.367 | 6.310  | 1.00 | 17.70 |
| ATOM | 1110 | O   | ASN A 157 | 25.368 | 12.330 | 5.469  | 1.00 | 20.91 |
| ATOM | 1111 | CB  | ASN A 157 | 27.115 | 10.714 | 8.300  | 1.00 | 30.34 |
| ATOM | 1112 | CG  | ASN A 157 | 27.733 | 9.498  | 7.932  | 1.00 | 34.95 |
| ATOM | 1113 | OD1 | ASN A 157 | 28.011 | 8.573  | 8.606  | 1.00 | 44.28 |
| ATOM | 1114 | ND2 | ASN A 157 | 27.965 | 9.541  | 6.660  | 1.00 | 54.18 |
| ATOM | 1115 | N   | VAL A 158 | 26.849 | 13.501 | 6.313  | 1.00 | 25.65 |
| ATOM | 1116 | CA  | VAL A 158 | 26.825 | 14.483 | 5.192  | 1.00 | 28.21 |
| ATOM | 1117 | C   | VAL A 158 | 26.768 | 13.893 | 3.758  | 1.00 | 24.85 |
| ATOM | 1118 | O   | VAL A 158 | 25.732 | 14.266 | 3.111  | 1.00 | 30.96 |
| ATOM | 1119 | CB  | VAL A 158 | 27.954 | 15.512 | 5.217  | 1.00 | 27.87 |
| ATOM | 1120 | CG1 | VAL A 158 | 28.751 | 14.595 | 4.238  | 1.00 | 40.51 |
| ATOM | 1121 | CG2 | VAL A 158 | 27.791 | 16.704 | 4.399  | 1.00 | 34.39 |
| ATOM | 1122 | N   | GLY A 159 | 27.483 | 12.956 | 3.016  | 1.00 | 5.94  |
| ATOM | 1123 | CA  | GLY A 159 | 26.713 | 12.774 | 1.732  | 1.00 | 6.20  |
| ATOM | 1124 | C   | GLY A 159 | 25.734 | 11.797 | 1.487  | 1.00 | 4.00  |
| ATOM | 1125 | O   | GLY A 159 | 25.732 | 10.704 | 0.848  | 1.00 | 4.06  |
| ATOM | 1126 | N   | ASP A 160 | 25.052 | 11.441 | 2.643  | 1.00 | 8.53  |
| ATOM | 1127 | CA  | ASP A 160 | 24.106 | 10.302 | 2.828  | 1.00 | 11.97 |
| ATOM | 1128 | C   | ASP A 160 | 22.755 | 10.698 | 2.177  | 1.00 | 14.44 |
| ATOM | 1129 | O   | ASP A 160 | 21.928 | 11.398 | 2.692  | 1.00 | 10.21 |
| ATOM | 1130 | CB  | ASP A 160 | 24.037 | 9.829  | 4.277  | 1.00 | 12.43 |
| ATOM | 1131 | CG  | ASP A 160 | 23.126 | 8.629  | 4.261  | 1.00 | 20.99 |
| ATOM | 1132 | OD1 | ASP A 160 | 22.525 | 8.408  | 3.179  | 1.00 | 33.03 |
| ATOM | 1133 | OD2 | ASP A 160 | 22.956 | 7.840  | 5.216  | 1.00 | 10.13 |
| ATOM | 1134 | N   | ALA A 161 | 22.455 | 10.402 | 0.961  | 1.00 | 12.33 |
| ATOM | 1135 | CA  | ALA A 161 | 21.318 | 10.743 | 0.269  | 1.00 | 11.01 |
| ATOM | 1136 | C   | ALA A 161 | 19.961 | 10.317 | 0.848  | 1.00 | 15.22 |
| ATOM | 1137 | O   | ALA A 161 | 18.969 | 11.034 | 0.594  | 1.00 | 9.50  |
| ATOM | 1138 | CB  | ALA A 161 | 21.365 | 10.334 | -1.172 | 1.00 | 13.68 |
| ATOM | 1139 | N   | VAL A 162 | 19.915 | 9.468  | 1.840  | 1.00 | 14.54 |
| ATOM | 1140 | CA  | VAL A 162 | 18.653 | 9.014  | 2.287  | 1.00 | 9.86  |
| ATOM | 1141 | C   | VAL A 162 | 18.235 | 10.063 | 3.258  | 1.00 | 13.50 |
| ATOM | 1142 | O   | VAL A 162 | 17.094 | 10.458 | 3.377  | 1.00 | 20.47 |
| ATOM | 1143 | CB  | VAL A 162 | 18.596 | 7.778  | 3.117  | 1.00 | 7.34  |
| ATOM | 1144 | CG1 | VAL A 162 | 18.931 | 6.592  | 2.259  | 1.00 | 6.50  |
| ATOM | 1145 | CG2 | VAL A 162 | 19.514 | 7.858  | 4.210  | 1.00 | 18.46 |
| ATOM | 1146 | N   | CYS A 163 | 19.198 | 10.733 | 3.719  | 1.00 | 13.44 |
| ATOM | 1147 | CA  | CYS A 163 | 18.864 | 11.811 | 4.720  | 1.00 | 11.26 |
| ATOM | 1148 | C   | CYS A 163 | 18.256 | 12.963 | 4.042  | 1.00 | 15.57 |
| ATOM | 1149 | O   | CYS A 163 | 18.219 | 13.857 | 4.880  | 1.00 | 14.09 |
| ATOM | 1150 | CB  | CYS A 163 | 20.144 | 12.145 | 5.570  | 1.00 | 18.70 |
| ATOM | 1151 | SG  | CYS A 163 | 20.748 | 10.705 | 6.581  | 1.00 | 13.38 |

| ATOM | 1152 | N   | THR | A | 164 | 18.100 | 13.014 | 2.696  | 1.00 | 21.82 |
| ATOM | 1153 | CA  | THR | A | 164 | 17.603 | 14.283 | 2.171  | 1.00 | 23.08 |
| ATOM | 1154 | C   | THR | A | 164 | 16.597 | 14.022 | 1.098  | 1.00 | 23.39 |
| ATOM | 1155 | O   | THR | A | 164 | 16.517 | 14.727 | 0.137  | 1.00 | 33.37 |
| ATOM | 1156 | CB  | THR | A | 164 | 18.463 | 15.341 | 1.454  | 1.00 | 23.25 |
| ATOM | 1157 | OG1 | THR | A | 164 | 19.486 | 14.707 | 0.674  | 1.00 | 23.21 |
| ATOM | 1158 | CG2 | THR | A | 164 | 18.958 | 16.261 | 2.491  | 1.00 | 37.71 |
| ATOM | 1159 | N   | GLY | A | 165 | 15.802 | 13.085 | 1.309  | 1.00 | 24.23 |
| ATOM | 1160 | CA  | GLY | A | 165 | 14.606 | 12.783 | 0.579  | 1.00 | 26.69 |
| ATOM | 1161 | C   | GLY | A | 165 | 14.699 | 11.814 | -0.515 | 1.00 | 28.56 |
| ATOM | 1162 | O   | GLY | A | 165 | 13.680 | 11.775 | -1.124 | 1.00 | 39.76 |
| ATOM | 1163 | N   | THR | A | 166 | 15.661 | 11.044 | -0.736 | 1.00 | 25.80 |
| ATOM | 1164 | CA  | THR | A | 166 | 16.006 | 10.220 | -1.774 | 1.00 | 25.53 |
| ATOM | 1165 | C   | THR | A | 166 | 16.195 | 8.866  | -1.175 | 1.00 | 25.35 |
| ATOM | 1166 | O   | THR | A | 166 | 16.913 | 8.760  | -0.206 | 1.00 | 30.91 |
| ATOM | 1167 | CB  | THR | A | 166 | 17.406 | 10.657 | -2.230 | 1.00 | 31.57 |
| ATOM | 1168 | OG1 | THR | A | 166 | 17.105 | 11.788 | -2.982 | 1.00 | 24.13 |
| ATOM | 1169 | CG2 | THR | A | 166 | 18.061 | 9.559  | -2.983 | 1.00 | 34.67 |
| ATOM | 1170 | N   | LEU | A | 167 | 15.734 | 7.833  | -1.817 | 1.00 | 19.63 |
| ATOM | 1171 | CA  | LEU | A | 167 | 16.219 | 6.552  | -1.465 | 1.00 | 16.11 |
| ATOM | 1172 | C   | LEU | A | 167 | 17.395 | 6.044  | -2.300 | 1.00 | 19.87 |
| ATOM | 1173 | O   | LEU | A | 167 | 17.265 | 4.869  | -2.612 | 1.00 | 21.38 |
| ATOM | 1174 | CB  | LEU | A | 167 | 15.086 | 5.624  | -1.555 | 1.00 | 23.45 |
| ATOM | 1175 | CG  | LEU | A | 167 | 14.123 | 5.773  | -0.401 | 1.00 | 33.91 |
| ATOM | 1176 | CD1 | LEU | A | 167 | 12.969 | 4.908  | -0.793 | 1.00 | 42.10 |
| ATOM | 1177 | CD2 | LEU | A | 167 | 14.776 | 5.385  | 0.903  | 1.00 | 25.86 |
| ATOM | 1178 | N   | ILE | A | 168 | 18.534 | 6.726  | -2.507 | 1.00 | 21.67 |
| ATOM | 1179 | CA  | ILE | A | 168 | 19.608 | 6.051  | -3.170 | 1.00 | 23.38 |
| ATOM | 1180 | C   | ILE | A | 168 | 20.675 | 5.585  | -2.189 | 1.00 | 20.47 |
| ATOM | 1181 | O   | ILE | A | 168 | 21.139 | 6.541  | -1.581 | 1.00 | 18.08 |
| ATOM | 1182 | CB  | ILE | A | 168 | 20.254 | 6.835  | -4.297 | 1.00 | 23.50 |
| ATOM | 1183 | CG1 | ILE | A | 168 | 21.232 | 7.874  | -3.800 | 1.00 | 13.71 |
| ATOM | 1184 | CG2 | ILE | A | 168 | 19.445 | 7.627  | -5.276 | 1.00 | 18.16 |
| ATOM | 1185 | CD1 | ILE | A | 168 | 20.908 | 8.938  | -4.804 | 1.00 | 26.95 |
| ATOM | 1186 | N   | ILE | A | 169 | 21.396 | 4.478  | -2.394 | 1.00 | 18.32 |
| ATOM | 1187 | CA  | ILE | A | 169 | 22.554 | 4.448  | -1.536 | 1.00 | 13.25 |
| ATOM | 1188 | C   | ILE | A | 169 | 23.924 | 4.662  | -1.967 | 1.00 | 11.95 |
| ATOM | 1189 | O   | ILE | A | 169 | 24.615 | 3.942  | -2.539 | 1.00 | 20.35 |
| ATOM | 1190 | CB  | ILE | A | 169 | 22.503 | 3.351  | -0.499 | 1.00 | 21.07 |
| ATOM | 1191 | CG1 | ILE | A | 169 | 23.398 | 2.181  | -0.655 | 1.00 | 11.06 |
| ATOM | 1192 | CG2 | ILE | A | 169 | 21.122 | 2.801  | -0.533 | 1.00 | 7.02  |
| ATOM | 1193 | CD1 | ILE | A | 169 | 22.581 | 1.266  | -1.587 | 1.00 | 32.83 |
| ATOM | 1194 | N   | THR | A | 170 | 24.570 | 5.586  | -1.296 | 1.00 | 17.16 |
| ATOM | 1195 | CA  | THR | A | 170 | 25.883 | 6.217  | -1.397 | 1.00 | 13.01 |
| ATOM | 1196 | C   | THR | A | 170 | 26.722 | 5.719  | -0.240 | 1.00 | 10.14 |
| ATOM | 1197 | O   | THR | A | 170 | 26.334 | 5.036  | 0.758  | 1.00 | 9.98  |
| ATOM | 1198 | CB  | THR | A | 170 | 25.623 | 7.713  | -1.344 | 1.00 | 15.02 |
| ATOM | 1199 | OG1 | THR | A | 170 | 26.466 | 7.947  | -0.255 | 1.00 | 23.39 |

```
ATOM   1200  CG2  THR A 170      24.389    7.914   -0.452   1.00  41.10
ATOM   1201  N    PRO A 171      28.000    5.738   -0.469   1.00  10.12
ATOM   1202  CA   PRO A 171      29.012    5.066    0.339   1.00  11.88
ATOM   1203  C    PRO A 171      28.897    5.492    1.765   1.00   9.74
ATOM   1204  O    PRO A 171      28.904    4.682    2.646   1.00   9.54
ATOM   1205  CB   PRO A 171      30.414    5.207   -0.286   1.00   7.15
ATOM   1206  CG   PRO A 171      30.017    5.603   -1.654   1.00   7.18
ATOM   1207  CD   PRO A 171      28.667    6.233   -1.601   1.00   6.90
ATOM   1208  N    ALA A 172      28.725    6.718    1.980   1.00   6.71
ATOM   1209  CA   ALA A 172      28.247    7.315    3.169   1.00   8.62
ATOM   1210  C    ALA A 172      27.075    6.631    3.892   1.00  10.99
ATOM   1211  O    ALA A 172      27.037    6.755    5.165   1.00  16.49
ATOM   1212  CB   ALA A 172      27.904    8.812    3.040   1.00   2.86
ATOM   1213  N    HIS A 173      26.287    5.815    3.278   1.00   6.36
ATOM   1214  CA   HIS A 173      25.133    5.468    4.081   1.00   5.29
ATOM   1215  C    HIS A 173      25.685    4.314    4.888   1.00  10.58
ATOM   1216  O    HIS A 173      25.082    3.598    5.668   1.00   9.36
ATOM   1217  CB   HIS A 173      24.081    4.883    3.216   1.00   8.41
ATOM   1218  CG   HIS A 173      22.815    4.403    3.791   1.00   7.30
ATOM   1219  ND1  HIS A 173      22.066    5.327    4.565   1.00   8.48
ATOM   1220  CD2  HIS A 173      22.148    3.264    3.670   1.00   7.83
ATOM   1221  CE1  HIS A 173      20.932    4.657    4.861   1.00  17.36
ATOM   1222  NE2  HIS A 173      20.945    3.423    4.379   1.00   5.29
ATOM   1223  N    LEU A 174      26.823    3.947    4.326   1.00   8.03
ATOM   1224  CA   LEU A 174      27.344    2.623    4.682   1.00   8.06
ATOM   1225  C    LEU A 174      28.171    2.787    5.930   1.00  13.06
ATOM   1226  O    LEU A 174      28.609    1.648    6.151   1.00  19.88
ATOM   1227  CB   LEU A 174      28.078    2.118    3.488   1.00   2.76
ATOM   1228  CG   LEU A 174      27.560    0.902    2.847   1.00  13.35
ATOM   1229  CD1  LEU A 174      26.024    1.017    2.796   1.00  18.01
ATOM   1230  CD2  LEU A 174      27.913    0.740    1.421   1.00  21.70
ATOM   1231  N    SER A 175      28.290    3.989    6.447   1.00  12.43
ATOM   1232  CA   SER A 175      29.230    4.052    7.553   1.00  18.01
ATOM   1233  C    SER A 175      28.872    4.811    8.847   1.00  19.89
ATOM   1234  O    SER A 175      28.968    6.047    9.120   1.00  14.61
ATOM   1235  CB   SER A 175      30.516    4.606    6.847   1.00  20.11
ATOM   1236  OG   SER A 175      30.834    5.907    7.293   1.00  27.73
ATOM   1237  N    TYR A 176      28.479    3.978    9.815   1.00  17.89
ATOM   1238  CA   TYR A 176      28.092    4.530   11.133   1.00  12.54
ATOM   1239  C    TYR A 176      28.530    3.671   12.272   1.00  11.16
ATOM   1240  O    TYR A 176      27.949    3.770   13.257   1.00   7.63
ATOM   1241  CB   TYR A 176      26.511    4.283   11.053   1.00   9.13
ATOM   1242  CG   TYR A 176      25.831    5.525   10.029   1.00   5.03
ATOM   1243  CD1  TYR A 176      25.874    6.923   10.425   1.00   2.75
ATOM   1244  CD2  TYR A 176      25.152    5.022    8.980   1.00   2.18
ATOM   1245  CE1  TYR A 176      25.287    7.754    9.633   1.00   4.25
ATOM   1246  CE2  TYR A 176      24.649    5.981    8.085   1.00   6.77
ATOM   1247  CZ   TYR A 176      24.658    7.329    8.399   1.00   6.22
```

```
ATOM   1248  OH   TYR A 176      24.074    8.375    7.635  1.00   5.76
ATOM   1249  N    THR A 177      29.430    2.685   12.167  1.00  10.72
ATOM   1250  CA   THR A 177      29.797    1.854   13.284  1.00  13.31
ATOM   1251  C    THR A 177      30.516    2.659   14.320  1.00  12.46
ATOM   1252  O    THR A 177      30.311    2.436   15.475  1.00  13.12
ATOM   1253  CB   THR A 177      30.658    0.683   12.798  1.00   3.49
ATOM   1254  OG1  THR A 177      31.361    1.247   11.870  1.00  32.08
ATOM   1255  CG2  THR A 177      29.675   -0.149   12.083  1.00   6.42
ATOM   1256  N    ILE A 178      31.409    3.474   13.920  1.00  10.48
ATOM   1257  CA   ILE A 178      32.203    4.246   14.783  1.00  15.25
ATOM   1258  C    ILE A 178      31.180    5.045   15.632  1.00  16.95
ATOM   1259  O    ILE A 178      31.092    4.774   16.851  1.00  22.68
ATOM   1260  CB   ILE A 178      33.338    5.121   14.357  1.00  25.11
ATOM   1261  CG1  ILE A 178      34.701    4.496   14.056  1.00  25.05
ATOM   1262  CG2  ILE A 178      33.599    6.205   15.392  1.00  27.60
ATOM   1263  CD1  ILE A 178      34.553    3.006   14.071  1.00  55.86
ATOM   1264  N    GLU A 179      30.218    5.799   15.178  1.00  16.34
ATOM   1265  CA   GLU A 179      29.290    6.610   15.985  1.00  16.94
ATOM   1266  C    GLU A 179      28.324    5.713   16.692  1.00  14.79
ATOM   1267  O    GLU A 179      27.683    6.012   17.716  1.00  19.20
ATOM   1268  CB   GLU A 179      28.555    7.637   15.169  1.00  21.16
ATOM   1269  CG   GLU A 179      28.790    7.283   13.691  1.00  50.37
ATOM   1270  CD   GLU A 179      29.933    7.701   12.851  1.00  61.82
ATOM   1271  OE1  GLU A 179      30.163    8.890   12.697  1.00  77.56
ATOM   1272  OE2  GLU A 179      30.627    6.854   12.309  1.00  75.83
ATOM   1273  N    ALA A 180      28.240    4.418   16.412  1.00   8.00
ATOM   1274  CA   ALA A 180      27.353    3.520   17.042  1.00  14.34
ATOM   1275  C    ALA A 180      28.048    2.991   18.280  1.00  19.53
ATOM   1276  O    ALA A 180      27.397    3.142   19.265  1.00  21.17
ATOM   1277  CB   ALA A 180      26.843    2.437   16.128  1.00  11.97
ATOM   1278  N    ARG A 181      29.317    2.547   18.287  1.00  21.89
ATOM   1279  CA   ARG A 181      29.992    1.982   19.398  1.00  16.48
ATOM   1280  C    ARG A 181      30.296    3.106   20.367  1.00  19.44
ATOM   1281  O    ARG A 181      30.243    3.104   21.639  1.00  28.53
ATOM   1282  CB   ARG A 181      31.310    1.408   19.143  1.00  12.43
ATOM   1283  CG   ARG A 181      31.954    0.432   20.052  1.00  45.44
ATOM   1284  CD   ARG A 181      32.596   -0.688   19.242  1.00  66.21
ATOM   1285  NE   ARG A 181      33.333   -0.030   18.164  1.00  85.83
ATOM   1286  CZ   ARG A 181      33.306   -0.321   16.895  1.00  91.35
ATOM   1287  NH1  ARG A 181      32.551   -1.320   16.530  1.00  96.98
ATOM   1288  NH2  ARG A 181      34.023    0.400   16.095  1.00  92.83
ATOM   1289  N    GLY A 182      30.387    4.262   19.847  1.00  13.94
ATOM   1290  CA   GLY A 182      30.553    5.404   20.728  1.00   7.40
ATOM   1291  C    GLY A 182      29.741    6.574   20.960  1.00   7.95
ATOM   1292  O    GLY A 182      29.171    6.512   22.083  1.00  12.73
ATOM   1293  N    GLU A 183      29.725    7.622   20.138  1.00   6.42
ATOM   1294  CA   GLU A 183      28.816    8.775   20.405  1.00  10.04
ATOM   1295  C    GLU A 183      27.421    8.369   20.645  1.00  14.41
```

| ATOM | 1296 | O | GLU | A | 183 | 26.846 | 8.530 | 21.749 | 1.00 | 15.43 |
|------|------|-----|-----|---|-----|--------|--------|--------|------|-------|
| ATOM | 1297 | CB | GLU | A | 183 | 29.053 | 9.791 | 19.402 | 1.00 | 21.24 |
| ATOM | 1298 | CG | GLU | A | 183 | 28.079 | 10.638 | 18.725 | 1.00 | 62.21 |
| ATOM | 1299 | CD | GLU | A | 183 | 28.248 | 12.103 | 19.141 | 1.00 | 81.34 |
| ATOM | 1300 | OE1 | GLU | A | 183 | 28.850 | 12.243 | 20.232 | 1.00 | 95.85 |
| ATOM | 1301 | OE2 | GLU | A | 183 | 27.791 | 13.027 | 18.430 | 1.00 | 90.85 |
| ATOM | 1302 | N | ALA | A | 184 | 26.766 | 7.605 | 19.808 | 1.00 | 15.56 |
| ATOM | 1303 | CA | ALA | A | 184 | 25.444 | 7.083 | 20.117 | 1.00 | 14.54 |
| ATOM | 1304 | C | ALA | A | 184 | 25.549 | 6.382 | 21.464 | 1.00 | 13.62 |
| ATOM | 1305 | O | ALA | A | 184 | 24.575 | 6.533 | 22.215 | 1.00 | 16.75 |
| ATOM | 1306 | CB | ALA | A | 184 | 25.019 | 6.015 | 19.089 | 1.00 | 9.58 |
| ATOM | 1307 | N | ALA | A | 185 | 26.428 | 5.396 | 21.774 | 1.00 | 9.42 |
| ATOM | 1308 | CA | ALA | A | 185 | 26.219 | 4.677 | 23.031 | 1.00 | 7.48 |
| ATOM | 1309 | C | ALA | A | 185 | 26.330 | 5.715 | 24.100 | 1.00 | 12.30 |
| ATOM | 1310 | O | ALA | A | 185 | 25.761 | 5.503 | 25.179 | 1.00 | 9.50 |
| ATOM | 1311 | CB | ALA | A | 185 | 27.138 | 3.475 | 23.260 | 1.00 | 4.60 |
| ATOM | 1312 | N | ARG | A | 186 | 27.271 | 6.673 | 24.090 | 1.00 | 15.54 |
| ATOM | 1313 | CA | ARG | A | 186 | 27.352 | 7.507 | 25.300 | 1.00 | 13.57 |
| ATOM | 1314 | C | ARG | A | 186 | 26.085 | 8.286 | 25.561 | 1.00 | 11.49 |
| ATOM | 1315 | O | ARG | A | 186 | 25.421 | 8.267 | 26.573 | 1.00 | 8.74 |
| ATOM | 1316 | CB | ARG | A | 186 | 28.484 | 8.460 | 25.043 | 1.00 | 30.29 |
| ATOM | 1317 | CG | ARG | A | 186 | 29.869 | 7.851 | 25.240 | 1.00 | 37.15 |
| ATOM | 1318 | CD | ARG | A | 186 | 30.983 | 8.826 | 24.813 | 1.00 | 42.36 |
| ATOM | 1319 | NE | ARG | A | 186 | 31.902 | 7.942 | 24.064 | 1.00 | 51.82 |
| ATOM | 1320 | CZ | ARG | A | 186 | 32.324 | 8.346 | 22.870 | 1.00 | 50.20 |
| ATOM | 1321 | NH1 | ARG | A | 186 | 31.924 | 9.538 | 22.424 | 1.00 | 47.65 |
| ATOM | 1322 | NH2 | ARG | A | 186 | 33.115 | 7.476 | 22.318 | 1.00 | 39.90 |
| ATOM | 1323 | N | PHE | A | 187 | 25.565 | 8.774 | 24.434 | 1.00 | 8.37 |
| ATOM | 1324 | CA | PHE | A | 187 | 24.195 | 9.370 | 24.426 | 1.00 | 13.48 |
| ATOM | 1325 | C | PHE | A | 187 | 23.187 | 8.476 | 25.182 | 1.00 | 15.92 |
| ATOM | 1326 | O | PHE | A | 187 | 22.379 | 8.916 | 25.995 | 1.00 | 14.81 |
| ATOM | 1327 | CB | PHE | A | 187 | 23.667 | 9.791 | 23.087 | 1.00 | 11.81 |
| ATOM | 1328 | CG | PHE | A | 187 | 22.282 | 10.323 | 23.032 | 1.00 | 14.64 |
| ATOM | 1329 | CD1 | PHE | A | 187 | 21.984 | 11.586 | 23.391 | 1.00 | 8.47 |
| ATOM | 1330 | CD2 | PHE | A | 187 | 21.186 | 9.599 | 22.564 | 1.00 | 18.34 |
| ATOM | 1331 | CE1 | PHE | A | 187 | 20.698 | 12.134 | 23.353 | 1.00 | 12.89 |
| ATOM | 1332 | CE2 | PHE | A | 187 | 19.895 | 10.026 | 22.485 | 1.00 | 17.42 |
| ATOM | 1333 | CZ | PHE | A | 187 | 19.661 | 11.322 | 22.924 | 1.00 | 3.70 |
| ATOM | 1334 | N | LEU | A | 188 | 23.033 | 7.232 | 24.803 | 1.00 | 15.17 |
| ATOM | 1335 | CA | LEU | A | 188 | 21.908 | 6.427 | 25.324 | 1.00 | 18.43 |
| ATOM | 1336 | C | LEU | A | 188 | 22.207 | 6.221 | 26.775 | 1.00 | 19.67 |
| ATOM | 1337 | O | LEU | A | 188 | 21.280 | 6.512 | 27.461 | 1.00 | 18.17 |
| ATOM | 1338 | CB | LEU | A | 188 | 21.703 | 5.088 | 24.552 | 1.00 | 18.72 |
| ATOM | 1339 | CG | LEU | A | 188 | 21.116 | 5.375 | 23.136 | 1.00 | 9.96 |
| ATOM | 1340 | CD1 | LEU | A | 188 | 20.950 | 4.066 | 22.601 | 1.00 | 7.86 |
| ATOM | 1341 | CD2 | LEU | A | 188 | 19.849 | 6.206 | 23.168 | 1.00 | 4.70 |
| ATOM | 1342 | N | ARG | A | 189 | 23.333 | 5.805 | 27.230 | 1.00 | 17.48 |
| ATOM | 1343 | CA | ARG | A | 189 | 23.798 | 5.812 | 28.547 | 1.00 | 18.41 |

| ATOM | 1344 | C   | ARG A 189 | 23.353 | 7.039  | 29.321 | 1.00 | 16.87 |
|------|------|-----|-----------|--------|--------|--------|------|-------|
| ATOM | 1345 | O   | ARG A 189 | 22.852 | 7.164  | 30.389 | 1.00 | 13.64 |
| ATOM | 1346 | CB  | ARG A 189 | 25.325 | 6.017  | 28.529 | 1.00 | 21.93 |
| ATOM | 1347 | CG  | ARG A 189 | 25.882 | 5.624  | 29.894 | 1.00 | 19.95 |
| ATOM | 1348 | CD  | ARG A 189 | 27.239 | 6.140  | 30.235 | 1.00 | 21.42 |
| ATOM | 1349 | NE  | ARG A 189 | 27.257 | 7.545  | 29.926 | 1.00 | 25.62 |
| ATOM | 1350 | CZ  | ARG A 189 | 28.491 | 7.983  | 29.699 | 1.00 | 29.22 |
| ATOM | 1351 | NH1 | ARG A 189 | 29.315 | 6.960  | 29.840 | 1.00 | 26.71 |
| ATOM | 1352 | NH2 | ARG A 189 | 28.780 | 9.210  | 29.383 | 1.00 | 33.27 |
| ATOM | 1353 | N   | ASP A 190 | 23.837 | 8.150  | 28.796 | 1.00 | 13.76 |
| ATOM | 1354 | CA  | ASP A 190 | 23.489 | 9.338  | 29.615 | 1.00 | 17.78 |
| ATOM | 1355 | C   | ASP A 190 | 22.008 | 9.364  | 29.711 | 1.00 | 16.79 |
| ATOM | 1356 | O   | ASP A 190 | 21.661 | 9.891  | 30.692 | 1.00 | 23.13 |
| ATOM | 1357 | CB  | ASP A 190 | 23.995 | 10.663 | 29.070 | 1.00 | 23.17 |
| ATOM | 1358 | CG  | ASP A 190 | 25.553 | 10.664 | 29.079 | 1.00 | 33.40 |
| ATOM | 1359 | OD1 | ASP A 190 | 26.250 | 9.836  | 29.761 | 1.00 | 22.68 |
| ATOM | 1360 | OD2 | ASP A 190 | 25.961 | 11.595 | 28.321 | 1.00 | 30.24 |
| ATOM | 1361 | N   | ARG A 191 | 21.156 | 9.128  | 28.781 | 1.00 | 21.61 |
| ATOM | 1362 | CA  | ARG A 191 | 19.707 | 9.265  | 28.849 | 1.00 | 20.99 |
| ATOM | 1363 | C   | ARG A 191 | 19.176 | 8.237  | 29.825 | 1.00 | 21.23 |
| ATOM | 1364 | O   | ARG A 191 | 18.327 | 8.515  | 30.651 | 1.00 | 20.98 |
| ATOM | 1365 | CB  | ARG A 191 | 19.014 | 9.214  | 27.450 | 1.00 | 19.76 |
| ATOM | 1366 | CG  | ARG A 191 | 19.605 | 10.282 | 26.521 | 1.00 | 27.49 |
| ATOM | 1367 | CD  | ARG A 191 | 18.848 | 11.594 | 26.689 | 1.00 | 36.68 |
| ATOM | 1368 | NE  | ARG A 191 | 17.559 | 11.023 | 27.144 | 1.00 | 60.89 |
| ATOM | 1369 | CZ  | ARG A 191 | 16.841 | 11.651 | 28.087 | 1.00 | 73.30 |
| ATOM | 1370 | NH1 | ARG A 191 | 17.404 | 12.780 | 28.496 | 1.00 | 76.65 |
| ATOM | 1371 | NH2 | ARG A 191 | 15.675 | 11.224 | 28.574 | 1.00 | 62.02 |
| ATOM | 1372 | N   | ILE A 192 | 19.734 | 7.037  | 29.885 | 1.00 | 21.02 |
| ATOM | 1373 | CA  | ILE A 192 | 19.500 | 6.080  | 30.913 | 1.00 | 21.92 |
| ATOM | 1374 | C   | ILE A 192 | 19.705 | 6.598  | 32.337 | 1.00 | 25.67 |
| ATOM | 1375 | O   | ILE A 192 | 19.145 | 6.053  | 33.263 | 1.00 | 27.95 |
| ATOM | 1376 | CB  | ILE A 192 | 20.289 | 4.775  | 30.750 | 1.00 | 24.23 |
| ATOM | 1377 | CG1 | ILE A 192 | 19.770 | 4.215  | 29.475 | 1.00 | 26.91 |
| ATOM | 1378 | CG2 | ILE A 192 | 19.923 | 3.983  | 31.951 | 1.00 | 15.15 |
| ATOM | 1379 | CD1 | ILE A 192 | 20.418 | 2.954  | 29.019 | 1.00 | 21.07 |
| ATOM | 1380 | N   | ARG A 193 | 20.535 | 7.574  | 32.629 | 1.00 | 28.72 |
| ATOM | 1381 | CA  | ARG A 193 | 20.800 | 8.068  | 33.963 | 1.00 | 33.95 |
| ATOM | 1382 | C   | ARG A 193 | 20.116 | 9.377  | 34.406 | 1.00 | 42.87 |
| ATOM | 1383 | O   | ARG A 193 | 20.479 | 9.267  | 35.618 | 1.00 | 48.19 |
| ATOM | 1384 | CB  | ARG A 193 | 22.298 | 8.179  | 34.167 | 1.00 | 34.19 |
| ATOM | 1385 | CG  | ARG A 193 | 23.096 | 6.896  | 34.100 | 1.00 | 39.38 |
| ATOM | 1386 | CD  | ARG A 193 | 24.590 | 7.213  | 34.133 | 1.00 | 65.92 |
| ATOM | 1387 | NE  | ARG A 193 | 25.339 | 5.973  | 34.003 | 1.00 | 81.05 |
| ATOM | 1388 | CZ  | ARG A 193 | 26.631 | 5.765  | 33.770 | 1.00 | 81.52 |
| ATOM | 1389 | NH1 | ARG A 193 | 27.441 | 6.816  | 33.647 | 1.00 | 80.92 |
| ATOM | 1390 | NH2 | ARG A 193 | 27.120 | 4.536  | 33.652 | 1.00 | 74.00 |
| ATOM | 1391 | OT  | ARG A 193 | 19.292 | 10.277 | 34.082 | 1.00 | 38.80 |
| TER  |      |     |           |        |        |        |      |       |

3D structure of cutinases from *F. solani pisi* (left) and *H. insolens* (right)

Hydrolysis of solid c3ET, 2 hr

Hydrolysis of c3ET on yarn, 17 hr

Treatment of yarn; time course

Treatment of yarn; time course

CUTINASE VARIANTS

CROSS-REFERENCE TO RELATED APPLICATIONS

This application is a 35 U.S.C. 371 national application of PCT/DK99/00678 filed Dec. 3, 1999 and claims, under 35 U.S.C. 119, priority or the benefit of Danish application nos. PA 1998 01604 and PA 1999 00330 filed Dec. 4, 1998 and Mar. 9, 1999, respectively, and U.S. application Ser. Nos. 60/111,591 and 60/124,671 filed Dec. 9, 1998 and Mar. 16, 1999, respectively, the contents of which are fully incorporated herein by reference.

FIELD OF THE INVENTION

The present invention relates to a cutinase variant, more particularly to a cutinase variant having improved thermostability. The invention also relates to a DNA sequence encoding the variant, a vector comprising the DNA sequence, a transformed host cell harboring the DNA sequence or the vector, to a method of producing the variant, and to use of the variant.

BACKGROUND OF THE INVENTION

Cutinases are lipolytic enzymes capable of hydrolyzing the substrate cutin. Cutinases are known from various fungi (P. E. Kolattukudy in "Lipases", Ed. B. Borgström and H. L. Brockman, Elsevier 1984, 471–504). The amino acid sequence and the crystal structure of a cutinase of *Fusarium solani pisi* have been described (S. Longhi et al., Journal of Molecular Biology, 268 (4), 779–799 (1997)). The amino acid sequence of a cutinase from *Humicola insolens* has also been published (U.S. Pat. No. 5,827,719).

A number of variants of the cutinase of *Fusarium solani pisi* have been published WO 94/14963; WO 94/14964; Appl. Environm. Microbiol. 64, 2794–2799, 1998; Proteins: Structure, Function and Genetics 26, 442–458, 1996; J. of Computational Chemistry 17, 1783–1803, 1996; Protein Engineering 6, 157–165, 1993; Proteins: Structure, Function, and Genetics 33, 253–264, 1998; J. of Biotechnology 66, 11–26, 1998; Biochemistry 35, 398–410, 1996.

Fungal cutinases may be used in the enzymatic hydrolysis of cyclic oligomers of poly(ethylene terephthalate), e.g. in the finishing of yarn or fabric from poly(ethylene terephthalate) fibers (WO 97/27237). However, it is desirable to improve the thermostability of known fungal cutinases to allow a higher process temperature.

SUMMARY OF THE INVENTION

The inventors have found certain variants of fungal cutinases having improved thermostability.

Accordingly, the invention provides a variant of a parent fungal cutinase comprising substitution of one or, more amino acid residues which is located:

a) within 17 Å from the location of the N-terminal amino acid (as calculated from amino acid residues in a crystal structure), and/or b) within 20 positions from the N-terminal amino acid.

The invention also provides a DNA sequence encoding the variant, an expression vector comprising the DNA sequence, a transformed host cell harboring the DNA sequence or the expression vector, a method of producing the variant, processes using the variant and a detergent composition comprising the variant.

BRIEF DESCRIPTION OF THE DRAWINGS

FIG. 1 gives the coordinates for the 3D structure of the cutinase of *H. insolens*.

DETAILED DESCRIPTION OF THE INVENTION

Fungal Cutinase

The parent cutinase is a fungal cutinase, such as a filamentous fungal cutinase, e.g. native to a strain of Humicola or Fusarium, specifically *H. insolens* or *F. solani pisi*, more specifically *H. insolens* strain DSM 1800.

The amino acid sequence of the cutinase of *H. insolens* strain DSM 1800 and the DNA sequence encoding it are shown as SEQ ID NO: 2 and SEQ ID NO: 1 of U.S. Pat. No. 5,827,719. The numbering system used herein for the *H. insolens* cutinase is based on the mature peptide, as shown in said SEQ ID NO: 2.

The amino acid sequence of the cutinase of *F. solani pisi* is shown as the mature peptide in FIG. 1D of WO 94/14964. The numbering system used herein for the *F. solani pisi* cutinase is that used in WO 94/14964; it includes the prosequence shown in said FIG. 1D; thus, the mature cutinase is at positions 16–214.

The parent cutinase may have an amino acid sequence which is at least 50% (particularly at least 70% or at least 80%) homologous to the cutinase of *H. insolens* strain DSM 1800. The parent cutinase may particularly be one that can be aligned with the cutinase of *H. insolens* strain DSM 1800.

Nomenclature for Amino Acids and Alterations

The specification and claims refer to amino acids by their one-letter codes. A particular amino acid in a sequence is identified by its one-letter code and its position e.g. Q1 indicates Gln (glutamine at position 1, i.e. at the N-terminal.

The nomenclature used herein for defining substitutions is basically as described in WO 92/05249. Thus, R51P indicates substitution of R (Arg) at position 51 with P (Pro).

Homology and Alignment

For purposes of the present invention, the degree of homology may be suitably determined according to the method described in Needleman, S. B. and Wunsch, C. D., (1970), Journal of Molecular Biology, 48, 443–45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version 8, August 1994, Genetics Computer Group, 575 Science Drive, Madison, Wis., USA 53711).

Two given sequences can be aligned according to the method described in Needleman (supra) using the same parameters. This may be done by means of the GAP program (supra).

Three-dimensional Structure of Cutinase

The structure of the cutinase of *H. insolens* was solved in accordance with the principle for X-ray crystallographic methods as given, for example, in X-Ray Structure Determination, Stout, G. K. and Jensen, L. H., John Wiley & Sons, Inc. NY, 1989. The structural coordinates for the solved crystal structure at 2.2 Å resolution using the isomorphous replacement method are given in FIG. 1 in standard PDB format (Protein Data Bank, Brookhaven National Laboratory, Brookhaven, Conn.).

Figure 2:
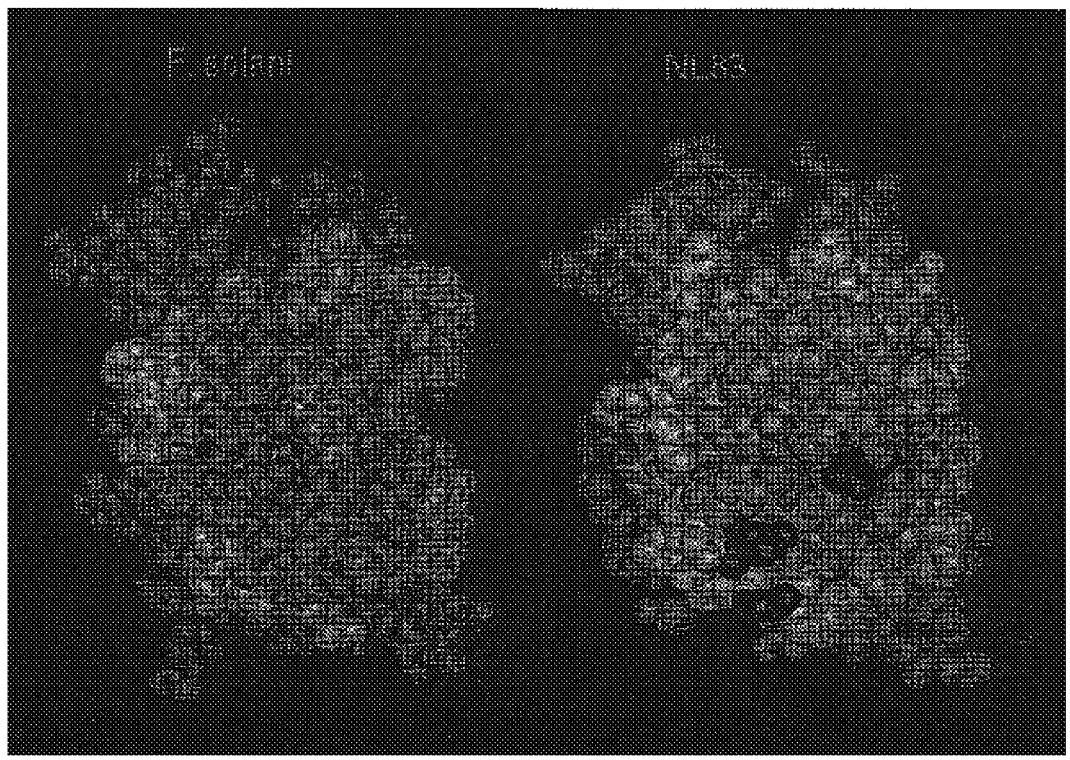
FIG. 2 is a computer model showing the three-dimensional structures of the cutinases from *F.solani pisi* (left) and *H. insolens* (right). Different colors have been used to identify the N-terminal amino acid and zones of 12 Å and 17 Å diameter around this.

The structure of the cutinase of *F. solani pisi* is described in Martinez et al. (1992) Nature 356, 615–618. The 3D structures of the cutinases of *F. solani pisi* and *H. insolens* are compared as a computer model in FIG. 2.

It should be noted that the overall three-dimensional structures of fungal cutinases are very similar and have been shown by X-ray crystallography to be highly homologous. The similarities between the cutinases from *F. solani pisi* and *H. insolens* are clearly apparent from the computer model in FIG. 2. Therefore, modifications of the type indicated for one fungal cutinase will also be functional for other fungal cutinases.

Substitution Near N-terminal

The variant of the invention has one or more amino acid substitutions in the vicinity of the N-terminal. The substitution is within a distance of 17 Å (e.g. within 12 Å) and/or within 20 positions (e.g. within 15 positions) of the N-terminal. The distance from the N-terminal is to be calculated between the Cα atom of the amino acids, and is calculated from an amino acid in a crystal structure (i.e. visible in the X-ray structure).

In the cutinase of *H. insolens* strain DSM 1800, the two N-terminal amino acids (Q1 and L2. i.e. Gln and Leu at positions 1 and 2) are not visible in the X-ray structure, so the distance is to be calculated from amino acid G3. Amino acids within 17 Å include positions 3–12, 18, 20–60, 62–64, 82, 85–86, 100–108, 110–111, 130–132, 174, 176–182, 184–185, 188, and 192. Those within 12 Å include positions 3–8, 22–27, 30–47, 53–59, 102, 177, and 180–181.

In the cutinase of *F. solani pisi*, the N-terminal amino acid G17 is visible in the X-ray structure. Amino acids within 17 Å include positions 17–26, 34–75, 77–79, 101, 115, 117–119, 147, 191–197, 199–200, and 203. Those within 12 Å include positions 17–22, 38, 40, 45–58, 60, 65, and 70–72.

The variants of the invention have improved thermostability compared to the parent enzyme. The thermostability may be determined from the denaturation temperature by DSC (differential scanning calorimetry), e.g. as described in an example, e.g. at pH 8.5 with a scan rate of 90 K/hr. The variants may have a denaturation temperature which is at least 5° C. higher than the parent enzyme.

The total number of substitutions in the above regions is typically 1–10, e.g. 1–5 substitutions in the above regions. In addition, the cutinase variant of the invention may optionally include other modifications of the parent enzyme, typically 10 or fewer, e.g. 5 or fewer alterations (substitutions, deletions or insertions) outside of the above regions. Thus, the total amino acid sequence of the variant typically 1–20, e.g. 1–10 alterations compared to the parent cutinase.

Solvent Accessible Surface

One or more of the substitutions may be made at an exposed amino acid residue, i.e. an amino acid residue having a solvent accessible surface. This can be calculated by the "dssp" program (version October 1988) described in W. Kabsch and C. Sander, Biopolymers, 22 (1983) pp. 2577–2637.

In the cutinase of *H. insolens* strain DSM 1800, the following amino acids lie within 17 Å of G3 at the N-terminal and have a solvent accessible surface greater than 0: 3–12, 18, 26–33, 36–38, 40–45, 47–56, 59–60, 62–64, 82, 85–86, 104–105, 174, 176–179, 181–182, 192.

Specific Substitutions

The substitution near the N-terminal may specifically be one that increases the electrical charge, i.e. a substitution of a negatively charged amino acid with a neutral or positively charged amino acid or substitution of a neutral amino acid with a positively charged amino acid. Thus, a negative amino acid residue at a position corresponding to position E6, E10, E30, E47 D63, E82 and/or E179 in the cutinase of *Humicola insolens* strain DSM 1800 may be substituted by a neutral or positive amino acid, e.g. R, K, Y, H, Q or N. Some specific substitutions are those corresponding to E6Q/N, E10Q/N, E47K/R or E179Q/N. Also, a neutral amino acid residue at a position corresponding to N7, S11, N44 or N52 in the *H. insolens* cutinase may be substituted by a positive amino acid (R, K or H).

Another example of a substitution near the N-terminal is substitution with a Pro residue, e.g. a substitution corresponding to A14P or R51P in the cutinase of *Humicola insolens* strain DSM 1800.

Specific Variants

The following are some examples of variants in the *H. insolens* cutinase. Corresponding variants may be made on the basis of other parent cutinases.

R51P
E6N/Q+L138I
A14P+E47K
E47K
E179N/Q
E6N/Q+E47K+R51P
A14P+E47K+E179N/Q
E47K+E179N/Q
E47K+D63N
E6N/Q+E10N/Q+A14P+E47K+R51P+E179N/Q
E6N/Q+A14P+E47K+R51P+E179N/Q
Q1P+L2V+S11C+N15T+F24Y+L46I+E47K

Use of Cutinase Variant

The cutinase variant of the invention may be used, e.g., for the enzymatic hydrolysis of cyclic oligomers of poly (ethylene terephthalate), such as cyclic tri(ethylene terephthalate), abbreviated as c3ET.

In particular, this may be used to remove such cyclic oligomers from polyester containing fabric or yarn by treating the fabric or yarn with the cutinase variant, optionally followed by rinsing the fabric or yarn with an aqueous solution having a pH in the range of from about pH 7 to about pH 11. The treatment of polyester is conveniently carried out above the glass transition temperature of c3ET (about 55° C.) and below the glass transition temperature of polyester (about 70° C.). Thus, the treatment may suitably be carried out at 50–80° C., e.g. at 60–75° C. The process may be carried out in analogy with WO 97/27237.

The cutinase variant may be used to treat polyester-containing textile. e.g. PET (polymer of ethyleneglycol and terephthalic acid), P3GT (polymer of 1,3-propanediol and terephthalic acid) or a polyester/cotton blend. The treatment may provide benefits to the polyester textile such as improved wear and comfort, increased water permeability, reduced antistatic behavior, improve handle and softness, changed redeposition characteristics and/or color clarification.

The cutinase variant may be used to improve the functional finish of a PET-containing yarn or fabric by a treatment with the cutinase variant, followed by a treatment with a finishing agent such as a softener, an anti-crease resin, an anti-static agent, an anti-soiling agent or agents to impair wrinkle-free, permanent press or fire resistance effects. The treatment with the cutinase variant may increase the number of functional groups in the surface, and this can be used to attach the functional finish. Examples of finishing agents are described in "SENSHOKU SIAGEKAKO BENRAN" published 1998-10-15 by Nihon Seni Sentaa K K.

The cutinase variant of the invention is also useful in detergents, where it may be incorporated to improve the removal of fatty soiling, as described in WO 94/03578 and WO 94/14964. The addition of the cutinase variant to laundry detergent may reduce malodor from cloth which is accumulated during several wash/wear-cycles.

The cutinase variant may also be used for degradation and recycling of polyester such as polycaprolactone (PCL), poly-ethyleneglycol-terephthalate (PET), polylactic acid, polybutylenesuccinate, and poly(hydroxybutiric acid)-co-(hydroxyvaleric acid), e.g. film and bottles, e.g. as described in JP-A 5-344897.

The cutinase variant may also be used for other known applications of lipases and cutinases, for example, in the baking industry (e.g. as described in WO 94/04035 and EP 585988), in the papermaking industry (e.g. for pitch removal, see EP 374700), and in the leather, wool and related industries (e.g. for degreasing of animal hides, sheepskin or wool), and for other applications involving degreasing/defatting. It may be used in immobilized form in the fat and oil industry, as a catalyst in organic synthesis (e.g. esterification, transesterification or ester hydrolysis reactions).

Dyeing Polyester

The invention provides a process for dyeing polyester fabric or yarn. In this process, the fabric or yarn is first treated with a cutinase, e.g. 12–48 hours at 50–70° C. or 65–70° C., pH 7–10, followed by dyeing with dye, e.g. a reactive dye, a disperse dye or a cationic dye. The reactive dye may be one that reacts with OH or COOH groups, e.g. having the structure Chromophore-NHPh—$SO_2CH_2CH_2OSO_3Na$. The dyeing may be conducted at 40–80° C., e.g. for 20–60 minutes.

The cutinase may be a thermostable cutinase having a thermal denaturation temperature, $T_d$, at pH 8.5 which is at least 5° higher than the parent cutinase, e.g. 7–10° higher, e.g. a value of 65° C. or higher. The measurement may be made by DSC as described in an Example of this specification.

Surfactant

In the treatment of fabric or yarn, a conventional wetting agent and/or a dispersing agent may be used to improve the contact with the enzyme. The wetting agent may be a nonionic surfactant, e.g. an ethoxylated fatty alcohol. A very useful wetting agent is an ethoxylated and propoxylated fatty acid ester such as Berol 087 (product of Akzo Nobel, Sweden).

The dispersing agent may suitably be selected from nonionic, anionic, cationic, ampholytic or zwitterionic surfactants. More specifically, the dispersing agent may be selected from carboxymethylcellulose, hydroxypropylcellulose, alkyl aryl sulfonates, long-chain alcohol sulfates (primary and secondary alkyl sulfates), sulfonated olefins, sulfated monoglycerides, sulfated ethers, sulfosuccinates, sulfonated methyl ethers, alkane sulfonates, phosphate esters, alkyl isothionates, acylsarcosides, alkyltaurides, fluorosurfactants, fatty alcohol and alkylphenol condensates, fatty acid condensates, condensates of ethylene oxide with an amine, condensates of ethylene oxide with an amide, sucrose esters, sorbitan esters, alkyloamides, fatty amine oxides, ethoxylated monoamines, ethoxylated diamines, alcohol ethoxylate and mixtures thereof. A very useful dispersing agent is an alcohol ethoxylate such as Berol 08 (product of Akzo Nobel, Sweden).

Methods for Preparing Cutinase Variants

The cutinase variant of the invention can be prepared by methods known in the art, e.g. as described in WO 94/14963 or WO 94/14964 (Unilever). The following describes methods for the cloning of cutinase-encoding DNA sequences, followed by methods for generating mutations at specific sites within the cutinase-encoding sequence.

Cloning a DNA Sequence Encoding a Cutinase

The DNA sequence encoding a parent cutinase may be isolated from any cell or microorganism producing the cutinase in question, using various methods well known in the art. First, a genomic DNA and/or cDNA library should be constructed using chromosomal DNA or messenger RNA from the organism that produces the cutinase to be studied. Then, if the amino acid sequence of the cutinase is known, labeled oligonucleotide probes may be synthesized and used to identify cutinase-encoding clones from a genomic library prepared from the organism in question. Alternatively, a labeled oligonucleotide probe containing sequences homologous to another known cutinase gene could be used as a probe to identify cutinase-encoding clones, using hybridization and washing conditions of lower stringency.

Yet another method for identifying cutinase-encoding clones would involve inserting fragments of genomic DNA into an expression vector, such as a plasmid, transforming cutinase-negative bacteria with the resulting genomic DNA library, and then plating the transformed bacteria onto agar containing a substrate for cutinase (i.e. maltose), thereby allowing clones expressing the cutinase to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859–1869, or the method described by Matthes et al., (1984), EMBO J. 3, p. 801–805. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K Saiki et al., (1988), Science 239, 1988, pp. 487–491.

Site-directed Mutagenesis

Once a cutinase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the cutinase-encoding sequence, is created in a vector carrying the cutinase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646–639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into cutinase-encoding DNA sequences is described in Nelson and Long, (1989), Analytical Biochemistry 180, p. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of Cutinase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a cutinase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a cutinase variant of the invention, especially in a bacterial host, are the promoter of the lac operon of *E.coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419–434, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and plJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a cutinase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Host Cells The cell of the invention, either comprising a DNA construct or an expression vector of the invention as defined above, is advantageously used as a host cell in the recombinant production of a cutinase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E.coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae.*

The host cell may also be a filamentous fungus e.g. a strain belonging to a species of *Aspergillus*, most preferably *Aspergillus oryzae* or *Aspergillus niger*, or a strain of *Fusarium*, such as a strain of *Fusarium oxysporium, Fusanrum graminearum* (in the perfect state named *Gribberella zeae,* previously *Sphaeria zeae*, synonym with *Gibberella roseum* and *Gibberella roseum* f. sp. *cerealis*), or *Fusarium sulphureum* (in the perfect state named *Gibberella puricaris*, synonym with *Fusarium trichothecioides, Fusarium bactridioides, Fusarium sambucium, Fusarium roseum,* and *Fusarium roseum* var. *graminearum*), *Fusarium cerealis* (synonym with *Fusarium crokkwellnse*), or *Fusarium venenatum.*

In a preferred embodiment of the invention the host cell is a protease deficient or protease minus strain.

This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of Aspergilus as a host micro-organism is described in EP 238 023 (Novo Nordisk A/S), the contents of which are hereby incorporated by reference.

Production of Cutinase Variant by Cultivation of Transformant

The invention relates, inter alia, to a method of producing a cutinase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the cutinase variant of the invention. Suitable media are available from commercial suppliers or may be prepared according to published recipes (e.g. as described in catalogues of the American Type Culture Collection).

The cutinase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Expression of Variant in Plants

The present invention also relates to a transgenic plant, plant part or plant cell which has been transformed with a DNA sequence encoding the variant of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism Arabidopsis thaliana.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the variant of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285–294). Organ-specific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–89 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promotter from a seed oil body protein (Chen et al., Plant and cell physiology vol. 39, No. 9 pp. 935–941 (1998), the storage protein napA promoter from *Brassica napus,* or any other seed specific promoter known in the art, eg as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, D W, Plant Molecular Biology Vol. 26, No. 1 pp. 85–93 (1994), or the aldP gene promoter from rice (Kagaya et al., Molecular and General Genetics Vol. 248, No. 6 pp. 668–474 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281;

Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well-known in the art.

Materials and Methods

Plasmids pJSO026

This is a S. cerevisiae expression plasmid described in WO 97/07205 and in J. S. Okkels, (1996) "A URA3-promoter deletion in a pYES vector increases the expression level of a fungal lipase in Saccharomyces cerevisiae. Recombinant DNA Biotechnology III: The Integration of Biological and Engineering Sciences, vol. 782 of the Annals of the New York Academy of Sciences).

pFuku83

This is a yeast and E. coli shuttle vector for expression of the H. insolens cutinase under the control of a TPI promoter, constructed from pJSO026.

Substrate

BETEB

Terephthalic acid bis(2-hydroxyethyl)ester dibenzoate is herein abbreviated as BETEB (benzoyl-ethylene-terephthalic-ethelene-benzoate). It was prepared from terephthalic acid bis (2-hydroxyethyl) ester and benzoic acid.

Lipase Activity (LU)

A substrate for lipase is prepared by emulsifying tributyrin (glycerin tributyrate) using gum Arabic as emulsifier. The hydrolysis of tributyrin at 30 ° C. at pH 7 is followed in a pH-stat titration experiment. One unit of lipase activity (1 LU) equals the amount of enzyme capable of releasing 1 μmol butyric acid/min at the standard conditions.

Differential Scanning Calorimetry (DSC)

Sample and reference solutions are carefully degassed immediately prior to loading of samples into the calorimeter (reference: buffer without enzyme). Sample and reference solutions (approx. 0.5 ml) are thermally pre-equillibrated for 20 minutes at 5° C. The DSC scan is performed from 5 C. to 95 C. at a scan rate of approx. 90 K/hr. Denaturation temperatures are determined at an accuracy of approx. +/−1 C. A VP-DSC from MicroCal Inc. is suitable for the experiments.

Methods

PCR Conditions step 1: 94° C., 120 sec.

step 2: 94° C., 60 sec step 3: 50° C., 60 sec step 4: 72° C., 150 sec.

Go to step 2, 35 cycles step 5: 72° C., 480 sec.

Step 6: 4° C., for ever

EXAMPLES

Example 1

Preparation of Cutinase Variants

A DNA sequence encoding H. insolens cutinase was obtained as described in U.S. Pat. No. 5,827,719 (Novo Nordisk) and was found to have the DNA sequence shown in SEQ ID NO: 1 therein.

Variants were prepared by localized random mutagenesis and selection of positive clones by incubation at 60° C. for 1 day on BETEB plates. The BETEB plates contained 200 ml/l of 500 mM glycine buffer (pH 8.5), 1.25 g/l of BETEB (dissolved in hot ethanol) and 20 g/l of agar.

Three positive variants were isolated, and their amino acid sequence was determined. They were found to have the following modifications, compared to the parent H. insolens cutinase:

A14P+E47K

E47K

E179Q

Example 2

Site Directed Mutation

A variant of the H. insolens cutinase having the substitutions E6Q+E47K+R51 P was prepared as follows:

A pair of PCR primers were designed so as to introduce amino acid substitutions, making use of the existed restriction enzyme sites nearby, as follows (an asterisk indicates an introduced mutation):

```
Upper primer: E6Q F
cgg cag ctg gga gcc atc c*ag aac (SEQ ID NO:1)
   Pvu II
```

PCR was run using these primers and pFukuNL83 as a template under the PCR condition described above.

The obtained PCR fragment was purified by Clontech Spincolumn and digested with Pvu II and BamH I.

The resultant fragment was gel-purified and ligated to pFukuNL83 which had been digested with the same restriction enzyme sites.

Example 3

Thermostability of Cutinase Variants

Variants

The thermostability was tested as described below for the H. insolens cutinase and the following variants thereof:

A14P+E47K

E47K

E179Q

E6Q+E47K+R51P

A14P+E47K+E179Q

E6Q+A14P+E47K+R51P+E179Q

E6Q+E10Q+A14P+E47K+R51P+E179Q

Differential Scanning Calorimetry (DSC)

Thermostability of cutinase variants was investigated by means of DSC at pH 4.5 (50 mM acetate buffer) and pH 8.5 (50 mM glycyl-glycine buffer). The thermal denaturation temperature, $T_d$, was taken as the top of denaturation peak (major endothermic peak) in thermograms (Cp vs. T) obtained after heating of enzyme solutions at a constant programmed heating rate.

The parent cutinase (Humicola insolens cutinase) was found to have $T_d$ of 61° C. at pH 4.5. Five of the above variants were found to have $T_d$ of 64–66° C., i.e. an improvement of 3–5°.

The parent cutinase was found to have $T_d$ of 61° C. at pH 4.5. Five of the above variants were found to have $T_d$ of 64–66° C., i.e. an improvement of 3–5°.

Hydrolysis of BETEB

The thermostability of the *H. insolens* cutinase and two of the above variants was measured by hydrolysis of BETEB at elevated temperature. For each cutinase, the following mixture was incubated for 17 hours at various temperatures in the range 55–70° C.:

0.1 ml 0.5 M glycyl-glycine buffer (pH 8.5)
0.1 ml 0.5% BETEB dissolved in ethanol
0.1 ml enzyme solution (approx. 25 LU/ml)
0.7 ml Milli Q water The degree of hydrolysis was measured after the incubation. The results are shown in the table below.

TABLE 1

|  | Variant (E47K) 27 LU/ml | Variant (E179Q) 25 LU/ml | Parent 24 LU/ml |
| --- | --- | --- | --- |
| 55° C. | 98% | 99% | 72% |
| 60° C. | 91% | 83% | 33% |
| 65° C. | 66% | 13% | 7% |

These results clearly show that the variants have improved thermostability compared to the parent cutinase.

Hydrolysis of BETEB

The thermostability of the *H. insolens* cutinase and three of the above variants was measured by hydrolysis of BETEB at 60° C. for 2 hours. The hydrolysis was carried out at the above conditions, except that the temperature was fixed at 60° C. and the cutinase dosage was varied. The results below are shown in the table below.

TABLE 2

| LU/ml | Variant (E6Q, A14P, E47K, R51P, E179Q) | Variant (E6Q, E10Q, A14P, E47K, R51P, E179Q) | Variant (A14P, E47K) | Parent |
| --- | --- | --- | --- | --- |
| 0 | 0% | 0% | 0% | 0% |
| 10 | 97% | 99% | 9% | 6% |
| 20 | 98% | 99% | 74% |  |
| 50 | 98% | 94% | 93% | 15% |
| 100 | 88% | 69% | 92% | 34% |
| 300 |  |  |  | 41% |
| 600 |  |  |  | 63% |
| 1200 |  |  |  | 82% |

The results show a much faster hydrolysis at 60° C. with the variants than with the parent cutinase.

Example 4

Hydrolysis of c3ET

The *H. insolens* cutinase and five of the above variants were tested in hydrolysis of c3ET at elevated temperature. For each cutinase, the following mixture was incubated for 2 hours at various temperatures.

0.115 mg c3ET (0.1 ml of 2 mM c3ET dissolved in HFIP was taken in reaction vessel. Solvent was removed under vacuum, then dried up at 70° C. over night)
0.1 ml 0.5 M glycyl-glycine buffer (pH8.5)
0.1 ml enzyme solution (approx. 600 LU/ml)
0.8 ml Milli Q water After the incubation, 2 ml of 1,1,1,3,3,3-Hexafluoro-2-propanol (HFIP) was added to each reaction mixture, then hydrolysis ratio was measured by HPLC.

Figure 3:
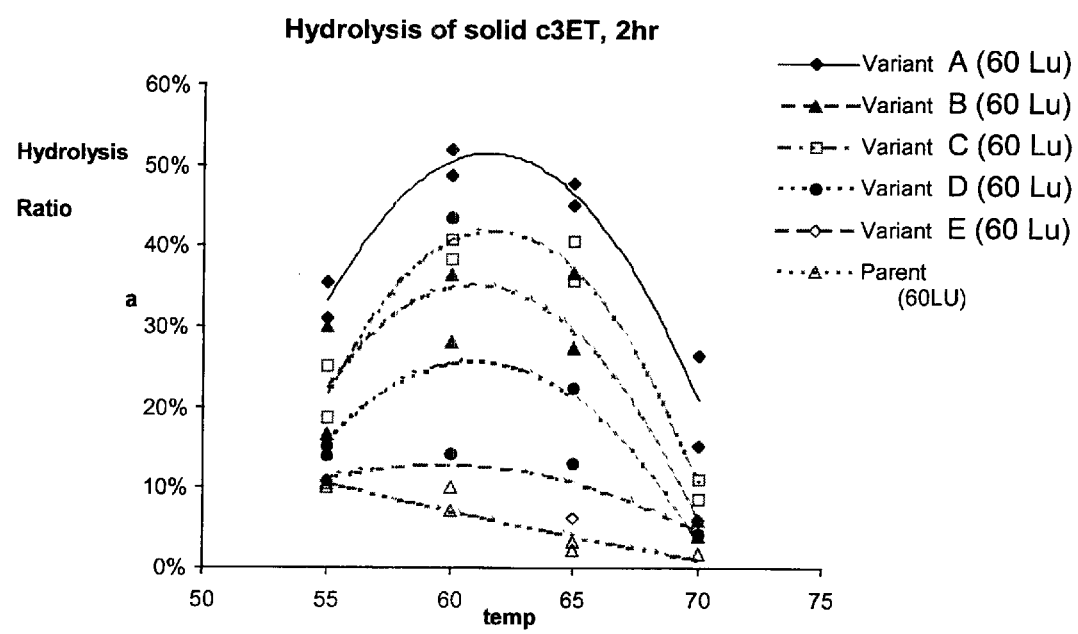
FIGS. 3–6 illustrate the hydrolysis of c3ET. Details are given in the Examples.

The variants tested were as follows:
Variant A: E6Q, E10Q, A14P, E47K, R51P, E179Q
Variant B: E6Q, A14P, E47K, R51P, E179Q
Variant C: A14P, E47K, E179Q
Variant D: E6Q, E47K, R51P
Variant E: E47K The results shown in FIG. 3 clearly indicate that the variants have improved thermostability, in particular, Variant A (E6Q, E10Q, A14P, E47K, R51P, E179Q, compared to the parent cutinase.

Example 5

Hydrolysis of c3ET on Yarn

The thermostability of the *H. insolens* cutinase five of the above variants was tested using polyester yarn containing c3ET as by product. The following substrate mixture was preincubated at 60 or 65° C.:

0.1 g polyester yarn
0.2 ml 0.5M glycyl-glycine buffer (pH8.5)
1.7 ml Milli Q water After preincubation, 0.1 ml enzyme solution (approx. 1000 LU/ml) was added to each reaction vessel and incubated for 17 hours. Then 2 ml HFIP was added and left for 30 minutes to extract and hydrolyze c3ET sitting on the surface of the polyester yarn; then the hydrolysis ratio was measured.

Figure 4:
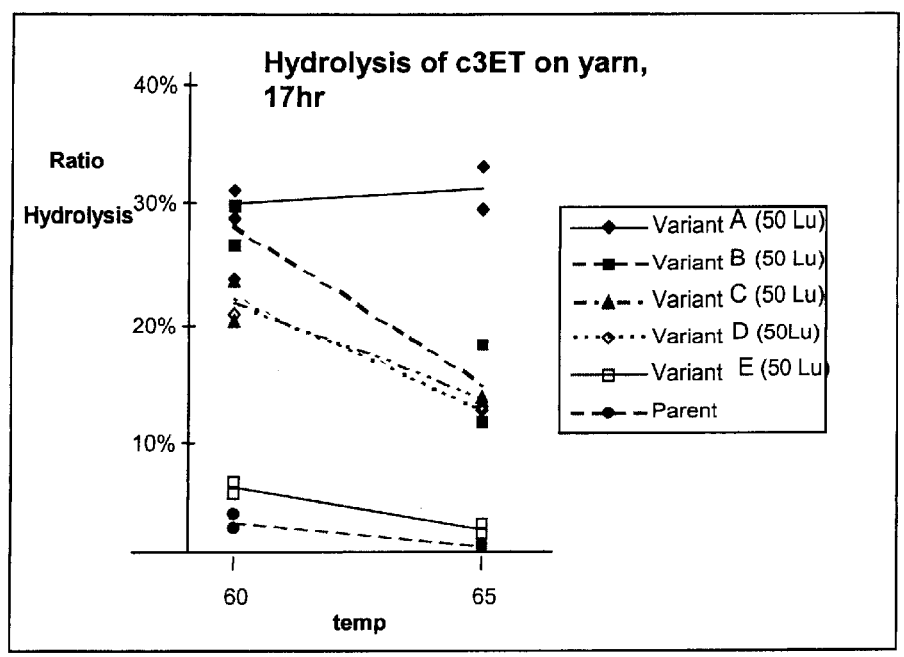

The variants tested were as follows:
Variant A: E6Q, E10Q, A14P, E47K, R51P, E179Q
Variant B: E6Q, A14P, E47K, R51P, E179Q
Variant C: A14P, E47K, E179Q
Variant D: E6Q, E47K, R51P
Variant E: E47K The results are shown in FIG. 4.

It is seen that the variants are more effective than the parent cutinase for hydrolyzing c3ET on polyester yarn, in particular, Variant A (E6Q, E10Q, A14P, E47K, R51P, E179Q). One variant (Variant A: E6Q, E10Q, A14P, E47K, R51P, E179Q) gives higher hydrolysis ratio at 65° C. than at 60° C.

Example 6

Treatment of Yarn with Cutinase Variant

Figure 5:
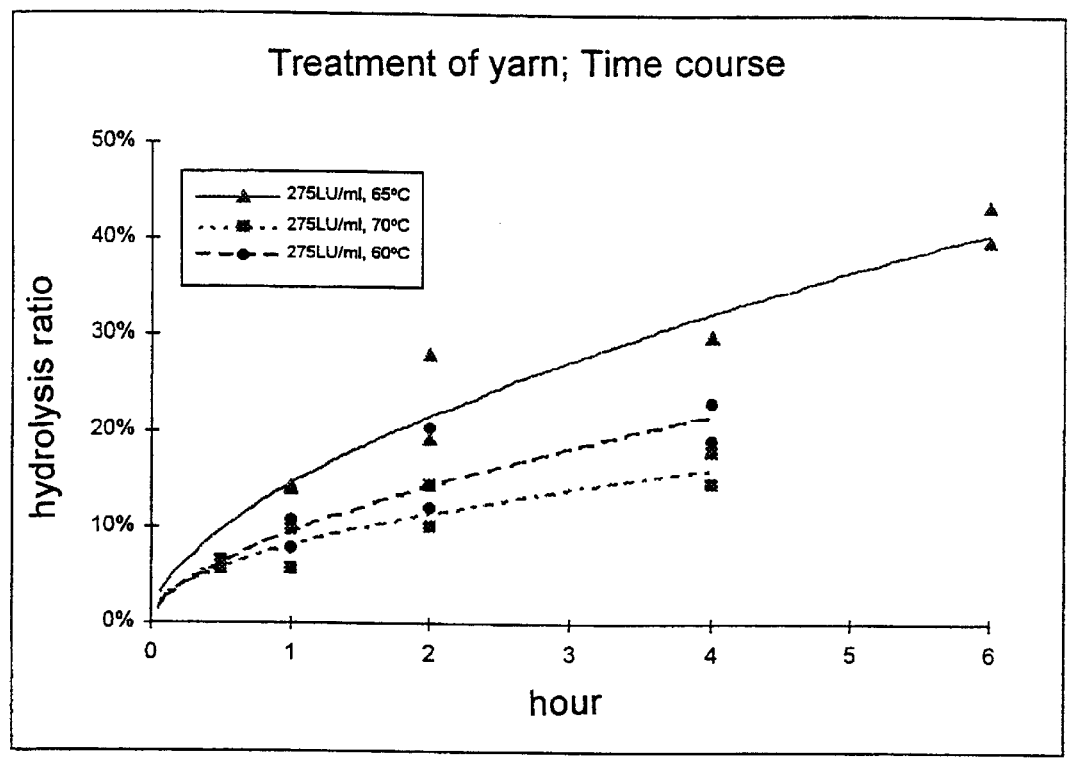
Figure 6:
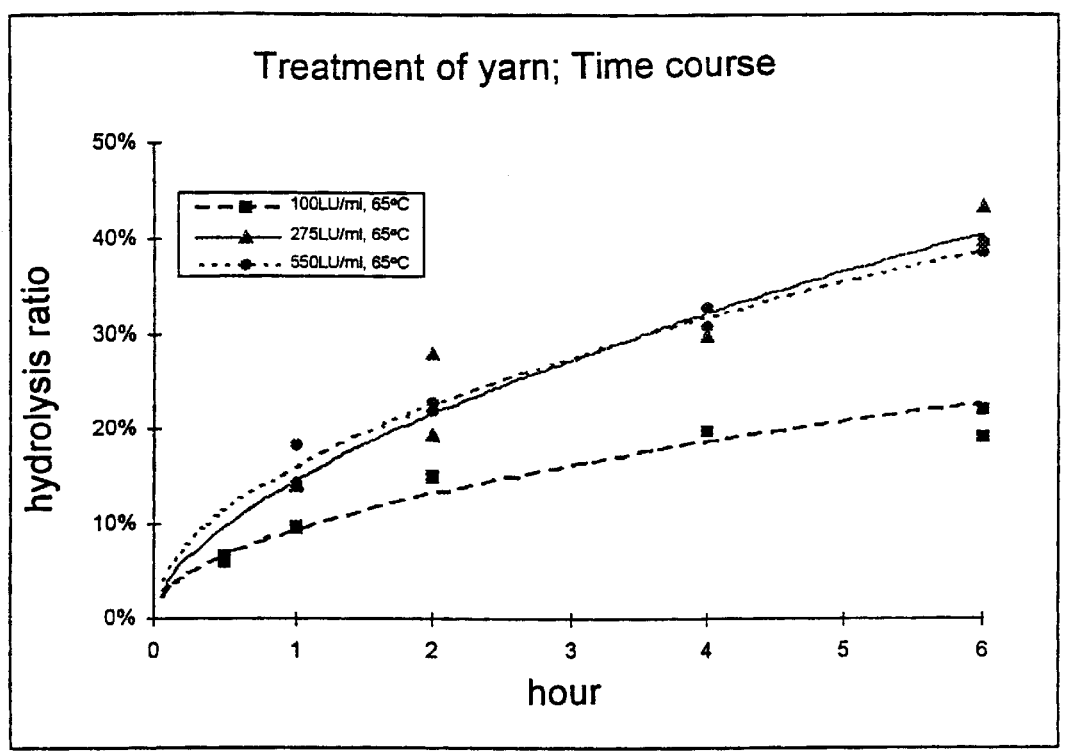

Time courses of c3ET hydrolysis on polyester yarn at different temperature or dosage were examined. Time course at different temperatures is shown in FIG. 5. It is seen that the optimum temperature is 65° C. for Variant E6Q, E10Q, A14P, E47K, R51P, E179Q. At 70° C. there is still about half of the activity left. Time course with increased enzyme dosage is shown in FIG. 6. The curves at dosage 275 and 550 LU/ml are seen to be the same, indicating that the hydrolysis ratio reached to plateau between dosage of 100 to 275 LU/ml. Presumably 200 LU/ml is enough.

Example 7

Dyeing Polyester with Reactive Dye

The following polyester fabrics were treated:
woven fabric; ca. 2×2 cm, 34 mg
knitted fabric; ca. 1.5×1.5 cm, 50 mg Each fabric was soaked in 0.9 ml, 50 mM GlyGly (glycyl-glycine) buffer (pH 8.5) and 0. 1 ml solution of a variant of the *H. insolens* cutinase (Variant E6Q, E10Q, A14P, E47K, R51 P, E179Q) (1100 LU/ml), and incubated at 65 or 70° C. After one day, another 0.1 ml enzyme solution was added, incubation was continued for two more days, the fabrics were then taken out and rinsed in water. A comparative experiment was made with the parent cutinase, and a blank was treated in the same manner without enzyme.

The fabrics were stirred in a mixture of 9 g 120 g $Na_2SO_4$ and 60 g $Na_2CO_3$ in 3 liter deionized water at 60° C. for 30 min, and then rinsed with running warm water. The reactive dye was Celmazol Brilliant Blue B (product of Mitsui Chemical Co., Japan), which has the structure Chromophore-NHPh—$SO_2CH_2CH_2OSO_3Na$.

In all four experiments, (woven and knitted, 65 and 70° C.), the fabrics were uniformly dyed.

Example 8

Solubilization of Polyester Fragments from Knitted Textile

A 1×1 cm sample of knitted polyester textile (PET, polymer of ethyleneglycol and terephthalic acid) was incubated for 1 hour in 1 ml of buffer at pH 10, 60° C. with 0.01 mg of a variant of *H. insolens* cutinase. The reaction mixture was separated, and the release of terephthalic acid was found by measuring OD at 250 nm (expressed as $OD_{250}$/mg PET). Comparative experiments were made without enzyme or with the parent cutinase. Results:

TABLE 3

| | Enzyme | $OD_{250}$ |
|---|---|---|
| Invention | Cutinase variant (E6Q, E10Q, A14P, E47K, R51P, E179Q) | 4.5 |
| Reference | Parent cutinase | 0.3 |
| | None | 0.1 |

The results show that the variant is effective in solubilizing polyester.

In another experiment, the cutinase variant was tested for 2 hours at 65° C. with and without the addition of a non-ionic surfactant (alcohol ethoxylate, product name Softanol 50), using various amounts of the variant from 0.5 to 200 LU/ml. The results showed more solubilization in the presence of non-ionic surfactant.

Example 9

Hydrolysis of Polycaprolactone and Polyester Film

About 0.1 g of polycaprolactone or polyester film were put in tubes. They were soaked in 5 ml of 50 mM GlyGly buffer (pH 8.5) with or without a variant of *H. insolens* cutinase (450 LU). They were incubated at 70° C. for 5 hours. After the reaction we observed a thin layer of hydrolysate on the surface of the tubes with enzyme, both with polycaprolactone and with polyester film. On the other hand no change was observed in controls without enzyme. In the case of polycaprolactone there was 10% of weight loss. We see no weight change of polyester.

Example 10 cPET Hydrolysis

The performance of a cutinase variant was compared with the parent enzyme (*H. insolens* cutinase). The trials were done as follows:

An oligomer-stained swatch of (black) PET-fabric (app. 4 cm×13 cm) is subjected to the enzyme-treatment at relatively low agitation in a so-called minitergitometer apparatus. The PET-fabric is mounted onto a cylindrical, perforated holder (radius ca.2 cm, height ca 6 cm), that rotates around its axis, and with the oligomer stained side of the PET fabric facing the exterior of the cylinder.

The fabric is immersed in a 150 ml glassbeaker containing 100 ml of the treatment solution at a given temperature (here 65° C.). After a given treatment time (here 90 minutes) the PET swatch is removed from the bath and rinsed in deionized water and air dried.

After conditioning the swatches are visually ranked (with respect to oligomer stain removal) on the side having the oligomer-staining. The rating being as follows:
- −2: Sample significantly worse than blank (no enzyme)
- −1: Sample slightly worse than blank (no enzyme)
- 0: Sample can not be distinguished from blank
- 1: Sample slightly improved vs blank
- 2: Sample significantly improved over blank Also, the swatches are read spectrofotometrically (apparatus: Hunterlab Reflectometer) to quantify the color strength (K/S-value at 600 nm).

The table below summarizes the test-conditions for a trial comparing the performance the enzymes under similar conditions:
- Temperature: 65° C.
- Buffer/pH: 50 mM glycine buffer, pH 10.3
- Treatment time (min) 90
- Dosage of Enzyme (LU/g) 30000

Results from the trial are summarized below

TABLE 4

| Enzyme | Visual rating (avg.) | K/S Difference @ 600 nm |
|---|---|---|
| None | 0 (defined) | 2.33 |
| Parent cutinase | 0 | 2.38 |
| Cutinase variant | 1.5–2.0 | 2.89 |

From this set of experiments it thus appears that the parent enzyme provides no or only very limited effect at the given test conditions (probably because the temperature is too high for the enzyme to retain activity), while the cutinase variant provides a substantial removal of the oligomer staining from the PET-fabric.

Example 11:

cPET Hydrolysis

The pH and temperature profile of a variant of *H. insolens* cutinase was tested in a model disperse dyeing experiment. The trials were performed as follows:

An oligomer-stained swatch of (black) PET-fabric is subjected to the conditions of a typical disperse dyeing sequence in a Werner Mathis Labomat. In over-view of the process, the swatch is added to a buffer solution, heated to 130° C., cooled down to the treatment temperature. Enzyme or buffer is added and then held at the desired temperature for 30 minutes. The solution is cooled down to room temperature and turbidity in the wash liquor is measured. The reduction in turbidity is a direct measure of the cutinase activity, corresponding to hydrolyzed cPET oligomers.

Detailed Description of the Experiment

A black PET (app. 4 cm×13 cm) swatch is added 140 ml 100 mM Britton-Robinson buffer containing 0.2 g/l Lutensol AT11 (BASF) and loaded in the Labomat (32 rotation per minute).

The Labomat is heated to 130° C. at a gradient of 9° C./minute, and held for 10 minutes.

The beakers are cooled to run temperature (according to table below) at a gradient of 9° C./minute, and held for 1 minute.

10 mL enzyme solution (100 LU/ml of the variant) or buffer solution (0 LU/ml) at appropriate pH is injected to the beakers.

The Labomat is re-heated to temperature at a gradient of 2° C./minute, and held for 30 minutes.

The swatches are removed, and the wash liquor is cooled down to room temperature.

Turbidity of the wash liquors are measured.

Evaluation: Turbidity is measured on Hach 18900 Ratio Turbidimeter (standardized with 1.8, 18, and 180 NTU Turbidity Standards). Enzyme performance is calculated relative to a blank as the difference between turbidity of blank liquor (no enzyme) and turbidity of enzyme treated liquor.

The relative performance (reduction in turbidity) of the cutinase variant is calculated, and the results are shown in the following table. When a negative number is obtained, then the result is given as "negative". A negative number is assumed to be an artifact, caused by the variation of the set up.

TABLE 5

| Temperature | pH 7 | pH 8 | pH 9 | pH 10 |
|---|---|---|---|---|
| 60° C. | 39 | 57 | 37 | 14 |
| 65° C. | 39 | 16 | 60 | 30 |
| 70° C. | 25 | 12 | 54 | 33 |
| 75° C. | 22 | 50 | 114 | 58 |
| 85° C. | negative | negative | 15 | negative |

The results show that the cutinase variant is active over a broad pH and temperature range, with optimum oligomer removal in the current set up around pH 9 and 75° C. Inactivation seems to occur at or above 85° C.

Example 12 cPET Hydrolysis

The effect of treatment time was investigated for a variant of *H. insolens* cutinase in a model disperse dyeing experiment. The trials were performed as follows:

An oligomer-stained swatch of (black) PET-fabric is subjected to the conditions of a typical disperse dyeing sequence in a Werner Mathis Labomat. In over-view of the process, the swatch is added to a buffer solution, heated to 130° C., cooled down to the treatment temperature. Enzyme or buffer (100 mM Britton-Robinson pH 9) is added, and then held at 75° C. for 0–40 minutes. The solution is cooled down to room temperature and turbidity in the wash liquor is measured. The reduction in turbidity is a direct measure of the cutinase activity, corresponding to hydrolyzed cPET oligomers.

Detailed Description of the Experiment

A black PET (app. 4 cm×13 cm) swatch is added to 140 ml 100 mM Britton-Robinson buffer containing 0.2 g/l Lutensol AT11 (BASF) and loaded in the Labomat (32 rotation per minute).

The Labomat is heated to 130° C. at a gradient of 9° C./minute, and the temperature is held for 10 minutes.

The beakers are cooled to 75° C. at a gradient of 9° C./minute, and held for 1 minute.

10mL enzyme solution (100 LU/ml of variant) or 100 mM Britton-Robinson buffer pH 9.0 (0 LU/ml) is injected into the beakers.

The Labomat is re-heated to 75° C. at a gradient of 2° C./minute, and held for the appropriate number of minutes (0–40 minutes, see table below).

The swatches are removed, and the wash liquor is cooled down to room temperature.

Turbidity of the wash liquors are measured.

Evaluation: Turbidity is measured on Hach 18900 Ratio Turbidimeter (standardized with 1.8, 18, and 180 NTU Turbidity Standards). Enzyme performance is calculated relative to a blank at time equal to zero: Turbidity of blank liquor at time zero (no enzyme) subtracted turbidity of enzyme treated liquor (at a given time).

The relative performance (reduction in turbidity) of the cutinase variant was calculated, and the results are shown in the following table.

TABLE 6

| Time (minutes) | Relative performance (Reduction in turbidity) |
|---|---|
| 0 | 0 |
| 5 | 42 |
| 10 | 48 |
| 15 | 62 |
| 20 | 69 |
| 25 | 85 |
| 30 | 72 |
| 40 | 78 |

The results show that the effect of the enzyme is increased over time. At the current enzyme dose and oligomer concentration, it seems to level off above approx. 20 minutes.

Example 13

Fiber Modification

The effect on wetting characteristics of a disperse dyed polyester fabric was investigated by treating the fabric with a variant of *H. insolens* cutinase prior to dyeing. The experiment therefore consisted of two phases, the actual fiber modification and the disperse dyeing procedure.

Phase 1—Fiber Modification

Equipment:: Atlas Launder-O-meter LP2

Fabric: knit 100% scoured polyester from Test fabrics pH: 50 mM potassium phosphate buffer, pH 7

Abrasives: 5 big steel balls

Beaker Vol.: 120 mL

Treatment: 2 hours 65° C. then ramped up to 90° C. and held for 1 hour

Swatch Prep: Cut 3*1.5 g swatch of fabric, 3 per beaker= 4.5 g

Rinse: Rinse in deionized water.

Phase 2—Dyeing—disperse dye

Dye Solution:

Add together with deionized water to make liquor ratio 1:20–0.4% Dianix Red (DyStar) SE-CB (owf)

pH to 4.5–5

Dyeing Procedure
1. One swatch per treatment from the fiber modification is used for the dyeing (1.5 g/swatch is used for the liquor ratio calculation).
2. Make dye bath according to the recipe above. Add the cold dye solution is to the Labomat beakers and heat to 55° C. at a gradient of 3.5° C./minute. Run for 5 minutes once temperature has been reached.
3. Add the fabric to the beaker.
4. Raise temperature to 130° C. at a gradient of 1.5° C./minute. Dye for 30 minutes.
5. Cool to 70° C. at a gradient of 5° C./minute. Drop bath, but collect, and rinse fabric hot (60° C.) for 10 minutes. Follow the hot rinse with a room temperature overflow rinse until all bleeding had stopped.
6. Let air dry overnight.

Tests/Analysis
AATCC Test Method 61—Colorfastness to washing
Percent Dyebath Exhaustion—Spectrophotometer
K/S and L*—Reflectometer
AATCC TM-79 Drop Test Results The results from the fiber modification are shown in the following table.

TABLE 7

| Variant dosage | Staining (AATCC TM-61) | Color Change (K/S @ 530 before and after TM-61) | Drop Test (AATCC TM-79) |
|---|---|---|---|
| Blank | 4.5 | 5 | 53 sec. |
| 50 LU/mL | 4.5 | 5 | 18 sec. |
| 100 LU/mL | 4.5 | 5 | 15 sec. |

The results show that the treatment of polyester with the variant increases the wetting substantially. No adverse effects are noticed on the dyeability with the disperse dye in the current set-up.

Example 14

Malodor Reduction in Textiles Soiled with Human Sweat/sebum by Use of a Cutinase Variant in Laundry The performance of cutinase, with respect to malodor reduction, can be tested in a one-cycle washing trial carried out in a Terg-O-tometer.

Experimental Conditions

Washing liquor: 1000 ml per beaker

Swatches: 100% polyester (interlock knitted, previously cleaned by Soxhlet extraction). 24 swatches (3.3×3.5 cm) per beaker.

Soil: Human male axillary sweat and sebum applied by wiping the armpits after exercise.

Detergent: 5 g/L of a standard color detergent. No pH adjustment.

Water hardness: 3.2 mM $Ca^{2+}/Mg^{2+}$ (in a ratio of 5:1)

Wash Temperature: 30° C.

Wash time: 30 min

Rinse: 15 minutes in running tap water

Evaluation

After wash the wet swatches are placed in closed, tinted 200 ml glasses. A trained sensory panel (9–11 judges) evaluates the odor by sniffing the headspace over the wet samples and evaluates the total odor intensity. The odor intensity is noted by placing a mark on an unstructured line scale measuring 15 cm, with word anchors at each end ('nothing' at the beginning of the scale and 'very strong' at the end). All evaluations are performed twice. The swatches are evaluated on day 1, 2 and 3 after wash (swatches are kept in the glasses at all times).

What is claimed is:

1. A variant of a parent *Humicola insolens* DSM 1800 cutinase which variant:
   (a) has 1–20 alterations within the amino acid sequence of the parent;
   (b) comprises substitution of one or more amino acid residues at a position which is located (i) within 17 Å from the location of the N-terminal amino acid (as calculated from amino acid residues in a crystal structure), and/or (ii) within 20 positions from the N-terminal amino acid; and
   (c) is more thermostable than the parent cutinase.

2. The variant of claim 1, which comprises substitution of one or more amino acid residues at a position which is located (i) within 12 Å from the location of the N-terminal amino acid (as calculated from amino acid residues in a crystal structure) and/or (ii) within 15 positions from the N-terminal amino acid.

3. The variant of claim 1, which comprises substitution of one or more amino acids having a solvent accessible surface.

4. The variant of claim 1, wherein one or more substitutions is substitution of a negatively charged amino acid with a neutral or positively charged amino acid or substitution of a neutral amino acid with a positively charged amino acid.

5. The variant of claim 4, wherein one or more substitutions is at a position corresponding to position E6, E10, E30, E47, D63, E82 and/or E179 in the cutinase of *Humicola insolens* strain DSM 1800.

6. The variant of claim 5, wherein one or more substitutions is with R/K/Y/H/Q/N.

7. The variant of claim 6, wherein one or more substitutions is E6N/Q, E10N/Q, E47K/R and/or E179N/Q.

8. The variant of claim 1, wherein one or more substitutions is substitution with a Pro residue.

9. The variant of claim 1, which has one, two, three, four, five or six of said substitutions.

10. The variant of claim 1, which has substitutions corresponding to one of the following in the cutinase of *Humicola insolens* strain DSM 1800:
    (a) R51P
    (b) E6N/Q+L138I
    (c) A14P+E47K
    (d) E47K
    (e) E179N/Q
    (f) E6N/Q+E47K+R51P
    (g) A14P+E47K+E179N/Q
    (h) E47K+E179N/Q
    (i) E47K+D63N
    (j) E6N/Q+A14P+E47K+R51P+E179N/Q
    (k) E6N/Q+E10N/Q+A14P+E47K+R51P+E179N/Q, or
    (l) Q1P+L2V+S11C+N15T+F24Y+L46I+E47K.

11. The variant of claim 1, which has hydrolytic activity towards terephthalic acid esters.

12. The variant of claim 1, which has a denaturation temperature which is at least 5° higher than the parent cutinase, measured at pH 8.5.

13. A DNA sequence encoding the variant of claim 1.

14. A vector comprising the DNA sequence of claim 12.

15. A transformed host cell harboring the DNA sequence of claim 13.

16. A process for enzymatic hydrolysis of a cyclic oligomer of poly(ethylene terephthalate), which process comprises treating the cyclic oligomer with the fungal cutinase variant of claim 1.

17. The process of claim 16, in which the cyclic oligomer is cyclic tri(ethylene terephthalate).

18. The process of claim 16, wherein the treatment is done at 60–80° C.

19. The process of claim 16, wherein the cyclic oligomer is present in and on the fibers of a polyester containing fabric or yarn.

20. The process of claim 16, which further comprises subsequently rinsing the fabric or yarn.

21. A detergent composition comprising a surfactant and the variant of claim 1.

22. The variant of claim 1, wherein one or more substitutions is substitution with a Pro at a position corresponding to position A14 and/or R51 of the amino acid sequence of the cutinase from *Humicola insolens* strain DSM 1800.

23. A variant of a parent *Humicola insolens* DSM 1800 cutinase wherein said variant is more thermostable than the parent cutinase and wherein said variant has 1–20 alterations within the amino acid sequence of the parent which variant comprises a substitution selected from the following substitutions:
    (a) a substitution of an amino acid position E6, E10, E30, E47, D63 and/or E82 in the amino acid sequence of the cutinase of *Humicola insolens* strain DSM 1800 with a neutral amino acid;
    (b) a substitution of an amino acid at position E179 in the amino acid sequence of the cutinase of *Humicola insolens* strain DSM 1800 with a neutral amino acid;
    (c) a substitution of an amino acid at position N7, S11, N44 and/or N52 in the amino acid sequence of the cutinase of *Humicola insolens* strain DSM 1800 with a positive amino acid; and
    (d) a substitution of an amino acid position A14 and/or R51 in the amino acid sequence of the cutinase of *Humicola insolens* strain DSM 1800 with Pro.

24. The variant of claim 23, comprising a substitution of an amino acid position position E6, E10, E30, E47, D63 and/or E82 in the amino acid sequence of the cutinase of *Humicola insolens* strain DSM 1800 with a neutral or positive amino acid.

25. The variant of claim 23, comprising a substitution of an amino acid position position E179 in the amino acid sequence of the cutinase of *Humicola insolens* strain DSM 1800 with a neutral amino acid.

26. The variant of claim 23, comprising a substitution of an amino acid position position N7, S11, N44 and/or N52 in the amino acid sequence of the cutinase of *Humicola insolens* strain DSM 1800 with a positive amino acid.

27. The variant of claim 23, comprising a substitution of an amino acid position position A14 and/or R51 in the amino acid sequence of the cutinase of *Humicola insolens* strain DSM 1800 with Pro.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Primer

<400> SEQUENCE: 1
cggcagctgg gagccatcca gaac             24

<210> SEQ ID NO 2
<211> LENGTH: 39
<212> TYPE: DNA
<213> ORGANISM: Primer

<400> SEQUENCE: 2
cgccctggat ccagatgttc gggatgtggg acttaaggc             39